(12) United States Patent
Balasubramanian et al.

(10) Patent No.: US 10,590,282 B2
(45) Date of Patent: *Mar. 17, 2020

(54) IDENTIFICATION AND CHARACTERIZATION OF NOVEL CORROSION INHIBITOR MOLECULES

(71) Applicant: Ecolab USA Inc., Saint Paul, MN (US)

(72) Inventors: Ramakrishnan Balasubramanian, Sugarland, TX (US); Brian Epps, Monument, CO (US); Jeremy Moloney, Katy, TX (US); Ethan Moloney, Katy, TX (US)

(73) Assignee: Ecolab USA Inc., Saint Paul, MN (US)

( * ) Notice: Subject to any disclaimer, the term of this patent is extended or adjusted under 35 U.S.C. 154(b) by 79 days.

This patent is subject to a terminal disclaimer.

(21) Appl. No.: 15/349,536

(22) Filed: Nov. 11, 2016

(65) Prior Publication Data

US 2017/0137634 A1 May 18, 2017

Related U.S. Application Data

(60) Provisional application No. 62/254,293, filed on Nov. 12, 2015.

(51) Int. Cl.
*C09D 5/08* (2006.01)
*C23F 11/173* (2006.01)
(Continued)

(52) U.S. Cl.
CPC ............... *C09D 5/08* (2013.01); *A01N 37/16* (2013.01); *C09D 5/086* (2013.01); *C09D 5/14* (2013.01);
(Continued)

(58) Field of Classification Search
None
See application file for complete search history.

(56) References Cited

U.S. PATENT DOCUMENTS 4,248,642 A * 2/1981 Kiyasu .................... B08B 3/08
134/10
4,637,899 A 1/1987 Kennedy, Jr.
(Continued)

FOREIGN PATENT DOCUMENTS

| CA | 2475361 A1 | 8/2003 |
| EP | 0231632 A2 | 8/1987 |

(Continued)

OTHER PUBLICATIONS

Kelland, Malcolm A. "Production Chemicals for the Oil and Gas Industry" Second Edition, CRC Press, pp. 331-336. Dec. 31, 2014.
(Continued)

*Primary Examiner* — Joseph D Anthony
(74) *Attorney, Agent, or Firm* — McKee, Voorhees & Sease, PLC

(57) ABSTRACT

Methods of employing corrosion inhibitors with oxidizing and/or non-oxidizing biocides, such as peroxycarboxylic acids, to provide corrosion protected compositions are disclosed. Various corrosion inhibitors further provide biocidal efficacy in addition to the corrosion protection providing further benefits for application of use. Methods of employing corrosion protected biocide compositions, such as peroxycarboxylic acid compositions, for corrosion protection are particularly well suited for treating fluids intended to flow through pipes, namely in the energy industry, water and paper industries, etc. Methods providing suitable corrosion protection in comparison to untreated systems and corrosion protected systems using conventional corrosion inhibitors, such as quaternary amines and imidazolines commonly used in the industry, are disclosed.

12 Claims, 23 Drawing Sheets

(51) Int. Cl.
*A01N 37/16* (2006.01)
*C23F 11/04* (2006.01)
*C23F 11/14* (2006.01)
*C23F 11/12* (2006.01)
*C23F 11/16* (2006.01)
*C23F 11/10* (2006.01)
*C09K 8/54* (2006.01)
*C09K 8/60* (2006.01)
*C09D 5/14* (2006.01)
*C09D 5/16* (2006.01)
*C09K 8/52* (2006.01)

(52) U.S. Cl.
CPC ............ *C09D 5/1625* (2013.01); *C09K 8/54* (2013.01); *C09K 8/605* (2013.01); *C23F 11/04* (2013.01); *C23F 11/10* (2013.01); *C23F 11/128* (2013.01); *C23F 11/144* (2013.01); *C23F 11/149* (2013.01); *C23F 11/164* (2013.01); *C23F 11/173* (2013.01); *C09K 8/52* (2013.01)

(56) References Cited

U.S. PATENT DOCUMENTS

| | | | |
|---|---|---|---|
| 5,616,335 A | 4/1997 | Nicolle et al. | |
| 5,616,616 A * | 4/1997 | Hall, II | A01N 37/16 422/12 |
| 5,635,195 A | 6/1997 | Hall, II et al. | |
| 5,840,343 A * | 11/1998 | Hall, II | A01N 37/16 424/616 |
| 6,043,203 A | 3/2000 | Urfer et al. | |
| 6,211,237 B1 * | 4/2001 | Huss | C02F 1/50 514/557 |
| 6,284,719 B1 | 9/2001 | Simms | |
| 6,432,895 B1 | 8/2002 | Bigorra et al. | |
| 7,087,569 B2 | 8/2006 | Lentsch et al. | |
| 7,135,448 B2 | 11/2006 | Lentsch et al. | |
| 7,196,045 B2 | 3/2007 | Lentsch et al. | |
| 7,524,803 B2 | 4/2009 | Lentsch et al. | |
| 7,759,299 B2 | 7/2010 | Smith et al. | |
| 7,858,574 B2 | 12/2010 | Smith et al. | |
| 8,021,493 B2 | 9/2011 | Smith et al. | |
| 8,802,061 B2 | 8/2014 | Tichy et al. | |
| 8,822,719 B1 | 9/2014 | Li et al. | |
| 8,828,910 B2 | 9/2014 | Aksela et al. | |
| 8,877,354 B2 | 11/2014 | Horiuchi et al. | |
| 9,044,403 B2 | 6/2015 | Shultz | |
| 9,192,909 B2 | 11/2015 | Kraus et al. | |
| 9,845,290 B2 * | 12/2017 | Balasubramanian | A01N 37/16 |
| 2003/0161808 A1 | 8/2003 | Bigorra Llosas et al. | |
| 2003/0200997 A1 | 10/2003 | Gill et al. | |
| 2004/0180028 A1 | 9/2004 | Prat Queralt et al. | |
| 2006/0177518 A1 | 8/2006 | Stevenson et al. | |
| 2007/0178811 A1 * | 8/2007 | Sundaram | B24C 1/003 451/39 |
| 2007/0249712 A1 | 10/2007 | Dee et al. | |
| 2012/0039821 A1 * | 2/2012 | Smigel | A61C 3/005 424/53 |
| 2013/0203849 A1 | 8/2013 | Ben Yehuda | |
| 2015/0018319 A1 | 1/2015 | Larson et al. | |
| 2015/0152329 A1 * | 6/2015 | Seetharaman | C09K 8/54 422/16 |
| 2015/0240365 A1 | 8/2015 | Monk | |
| 2015/0265666 A1 * | 9/2015 | Modak | A01N 65/00 424/616 |
| 2016/0176814 A1 * | 6/2016 | Balasubramanian | A01N 37/16 514/714 |
| 2017/0064949 A1 * | 3/2017 | Kraus | A01N 37/36 |
| 2018/0093948 A1 * | 4/2018 | Balasubramanian | A01N 37/16 |
| 2018/0168150 A1 * | 6/2018 | Li | A01N 37/16 |

FOREIGN PATENT DOCUMENTS

| | | |
|---|---|---|
| EP | 0395296 A2 | 10/1990 |
| EP | 1022946 B1 | 8/2000 |
| EP | 1125497 A2 | 6/2003 |
| EP | 1131016 B1 | 2/2005 |
| WO | 001828 A1 | 4/2000 |
| WO | 2000045639 A1 | 8/2000 |
| WO | 2008088873 A1 | 7/2008 |
| WO | 2015100031 A1 | 7/2015 |
| WO | 2016100700 A1 | 6/2016 |

OTHER PUBLICATIONS

Ecolab USA Inc., PCT/US2016/061468 filed Nov. 11, 2016, "Written Opinion of the International Searching Authority" dated Feb. 23, 2017, 8 pages.

U.S. Patent Application filed Feb. 27, 2014, Inventor Keith A. Monk, "Quaternary Fatty Acid Esters as Corrosion Inhibitors" 32 pages.

European Patent Office, extended European Search Report of Application 16865057.0, 12 pages, dated Apr. 18, 2019.

* cited by examiner

IDENTIFICATION AND CHARACTERIZATION OF NOVEL CORROSION INHIBITOR MOLECULES

CROSS-REFERENCE TO RELATED APPLICATIONS

This application claims priority under 35 U.S.C. § 119 to U.S. Provisional Application Ser. No. 62/254,293 filed Nov. 12, 2015 titled "Identification and Characterization of Novel Corrosion Inhibitor Molecules," the entire contents of which is hereby expressly incorporated herein by reference including, without limitation, the specification, claims, and abstract, as well as any figures, tables, or drawings thereof.

FIELD OF THE INVENTION

The invention relates to corrosion control including prevention of corrosion in systems using an oxidizing or a non-oxidizing biocide, such as for example peroxycarboxylic acid compositions, quaternary phosphonium salts including tetrakis(hydroxymethyl)phosphonium sulfate (THPS), and/or aldehydes including gluteraldehyde compositions. In particular, the corrosion protection properties of novel corrosion inhibitors prevent any microbial induced corrosion from the biocidal compositions, including percarboxylic acids of varying chain lengths. In some embodiments, the corrosion inhibitors provide biocidal efficacy in addition to the corrosion protection provide further benefits for application of use. Methods of employing the corrosion inhibitors with the biocidal compositions, including peroxycarboxylic acid compositions, are particularly well suited for treating fluids intended to flow through pipes, namely in the energy industry, water and paper industries, etc. The methods provide suitable corrosion protection in comparison to untreated systems and corrosion protection achieved from known corrosion inhibitors, such as quaternary amines and imidazolines commonly used in the industry.

BACKGROUND OF THE INVENTION

Among various biocides known, peroxycarboxylic acids are increasingly used in many applications, owing to their high efficacy against a broad spectrum of microorganisms, color safe property, low residues and nontoxic nature of their decomposition products. The use of peroxycarboxylic biocides are particularly useful in promoting water reuse in conventional and unconventional oil and gas exploration. However, various limitations of employing peroxycarboxylic biocides in the oil and gas industry, along with other industries, are known including corrosive effects resulting from use of peroxycarboxylic biocides for protection against microbial induced corrosion (MIC) which limits its applications of use.

Corrosion prevents significant difficulties in oil and gas wells which are typically subjected to numerous chemical treatments during their production life to enhance operation and protect the integrity of the surfaces. Corrosion of metal surfaces in aqueous media has long been a problem for the oil and gas industry. It is well-known that during the production of oil and gas several other corrosive components are present, such as brines, organic acids, carbon dioxide, hydrogen sulfide, and microorganisms. These aggressive constituents can cause severe corrosion as demonstrated by surface pitting, embrittlement, and loss of metal.

Corrosion issues are even more troublesome in deep-sea operations where replacement of corroded equipment is difficult and costly. Therefore, it is common practice to employ corrosion inhibitors during the production, transportation, storage, and separation of crude oil and natural gas. Corrosion inhibitors are usually surface-active compounds that form protective coatings on the surface of metals and suppress corrosion by preventing or reducing contact of the corrosive species to the pipeline surface. Common corrosion inhibitors are composed of amines, condensation products of fatty acids with polyamines, imidazolines, and/or quaternary ammonium compounds. Among the most frequently used corrosion inhibitors in crude oil and natural gas extraction are imidazoline derivatives and benzyldimethylalkylammonium chlorides.

There is a need for development of new, high-performance actives that meet the needs for corrosion control in various applications including those treated with biocides causing corrosion.

Accordingly, it is an objective of the invention to develop corrosion-inhibiting water treatments for use in systems for use in oil and gas and other operations.

A further object of the invention is to provide a method of reducing or elimination corrosion in a treated water using an oxidizing or a non-oxidizing biocide, such as peroxycarboxylic acids, and a novel corrosion inhibitor molecule.

Other objects, advantages and features of the present invention will become apparent from the following specification taken in conjunction with the accompanying drawings.

BRIEF SUMMARY OF THE INVENTION

The present invention relates generally to the use of peroxycarboxylic acids and other non-oxidizing biocides and corrosion inhibitor molecules for inhibiting, reducing and/or eliminating corrosion in a water source and/or treated system. The present invention further relates to the uses of corrosion inhibited biocides for treating a target water source, e.g., water used in connection with oil- and gas-field operations for anti-corrosion benefits.

In an additional aspect, the invention relates to corrosion inhibited aqueous compositions including from about 0.5 ppm to about 50,000 ppm of an oxidizing or non-oxidizing biocide, and from about 1 ppm to about 10,000 ppm of a corrosion inhibitor. In an aspect the corrosion inhibited aqueous composition is a peroxyformic acid composition. In an aspect, the corrosion inhibitors include alkyl pyridinium salts, cetyl pyridinium salts, polyesteramides, dimethicones, imidazole derivatives, sulphonamides and combinations thereof. In an aspect pH of the compositions is below 12.0. In an aspect, the corrosion inhibited aqueous composition provides a treated surface or system with a corrosion rate of less than about 4 mils per year (MPY).

In an additional aspect, the invention relates to a peroxyformic acid pre-mix composition for generating a corrosion inhibited biocide composition comprising: a first premix composition comprising formic acid and a corrosion inhibitor selected from the group consisting of alkyl pyridinium salts, cetyl pyridinium salts, polyesteramides, dimethicones, imidazole derivatives, sulphonamides and combinations thereof; and a second composition comprising a hydrogen peroxide source, wherein the combination of the first premix composition and the second composition generate peroxyformic acid in situ. In an aspect, the premix composition is stable for an extended period of time.

In an additional aspect, the invention relates to a corrosion inhibited non-oxidizing biocide composition comprising a non-oxidizing biocide and a corrosion inhibitor selected from the group consisting of alkyl pyridinium salts, cetyl pyridinium salts, polyesteramides, dimethicones, imidazole derivatives, sulphonamides and combinations thereof. In an aspect, the premix composition is stable for an extended period of time.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
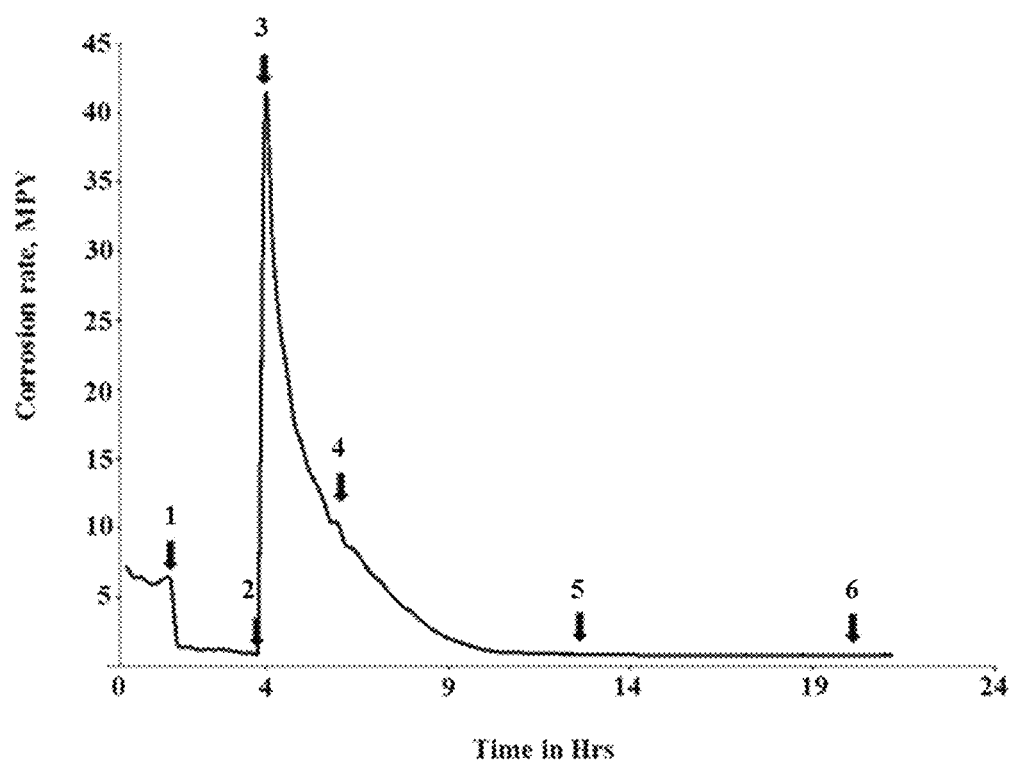
FIG. 1 shows a typical corrosion profile obtained from bubble cell experiments.

Various embodiments of the present invention will be described in detail with reference to the drawings, wherein like reference numerals represent like parts throughout the several views. Reference to various embodiments does not limit the scope of the invention. Figures represented herein are not limitations to the various embodiments according to the invention and are presented for exemplary illustration of the invention.

DETAILED DESCRIPTION OF THE PREFERRED EMBODIMENT

The embodiments of this invention are not limited to particular compositions and/or methods of corrosion inhibition, which can vary and are understood by skilled artisans. For clarity of disclosure, and not by way of limitation, the detailed description of the invention is divided into the subsections that follow. It is further to be understood that all terminology used herein is for the purpose of describing particular embodiments only, and is not intended to be limiting in any manner or scope. For example, as used in this specification and the appended claims, the singular forms "a," "an" and "the" can include plural referents unless the content clearly indicates otherwise. Further, all units, prefixes, and symbols may be denoted in its SI accepted form.

Definitions

Unless defined otherwise, all technical and scientific terms used herein have the same meaning as is commonly understood by one of ordinary skill in the art to which this invention belongs. All patents, applications, published applications and other publications referred to herein are incorporated by reference in their entireties. If a definition set forth in this section is contrary to or otherwise inconsistent with a definition set forth in the patents, applications, published applications and other publications that are herein incorporated by reference, the definition set forth in this section prevails over the definition that is incorporated herein by reference.

So that the present invention may be more readily understood, certain terms are first defined. Unless defined otherwise, all technical and scientific terms used herein have the same meaning as commonly understood by one of ordinary skill in the art to which embodiments of the invention pertain. Many methods and materials similar, modified, or equivalent to those described herein can be used in the practice of the embodiments of the present invention without undue experimentation, the preferred materials and methods are described herein. In describing and claiming the embodiments of the present invention, the following terminology will be used in accordance with the definitions set out below.

Throughout this disclosure, various aspects of this invention are presented in a range format. It should be understood that the description in range format is merely for convenience and brevity and should not be construed as an inflexible limitation on the scope of the invention. Accordingly, numeric ranges recited within the specification are inclusive of the numbers within the defined range. The description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

The term "about," as used herein, refers to variation in the numerical quantity that can occur, for example, through typical measuring and liquid handling procedures used for making concentrates or use solutions in the real world; through inadvertent error in these procedures; through differences in the manufacture, source, or purity of the ingredients used to make the compositions or carry out the methods; and the like. The term "about" also encompasses amounts that differ due to different equilibrium conditions for a composition resulting from a particular initial mixture. Whether or not modified by the term "about", the claims include equivalents to the quantities.

The term "actives" or "percent actives" or "percent by weight actives" or "actives concentration" are used interchangeably herein and refers to the concentration of those ingredients involved in cleaning expressed as a percentage minus inert ingredients such as water or salts.

As used herein, the term "cleaning" refers to a method used to facilitate or aid in soil removal, bleaching, microbial population reduction, and any combination thereof. For the purpose of this patent application, successful microbial reduction is achieved when the microbial populations are reduced by at least about 50%, or by significantly more than is achieved by a wash with water. Larger reductions in microbial population provide greater levels of protection.

"Corrosion" means a chemical process which takes place on the surface of the solid material in contact with a fluidic medium, the process causes a loss of material from the surface to the medium, it may be the result of an anodic-cathodic type reaction caused between iron and water, it excludes erosion type processes. Biocorrosion means corrosion resulting from the presence and activities of microorganisms which induce, accelerate, and/or maintain a corrosion reaction in a solid surface (such as metal)-fluid interface, typically conditioned by a biofilm, its rate and effects are influenced by the type/composition of the solid surface and/or fluid, the arrangement of the microorganisms on the solid surface, and/or the metabolic activity of the microorganisms.

As used herein, the term "disinfectant" refers to an agent that kills all vegetative cells including most recognized pathogenic microorganisms, using the procedure described in *A.O.A.C. Use Dilution Methods*, Official Methods of Analysis of the Association of Official Analytical Chemists, paragraph 955.14 and applicable sections, 15th Edition, 1990 (EPA Guideline 91-2). As used herein, the term "high level disinfection" or "high level disinfectant" refers to a compound or composition that kills substantially all organisms, except high levels of bacterial spores, and is effected with a chemical germicide cleared for marketing as a sterilant by the Food and Drug Administration. As used herein, the term "intermediate-level disinfection" or "intermediate level disinfectant" refers to a compound or composition that kills mycobacteria, most viruses, and bacteria with a chemical germicide registered as a tuberculocide by the Environmental Protection Agency (EPA). As used herein, the term "low-level disinfection" or "low level disinfectant" refers to a compound or composition that kills some viruses and bacteria with a chemical germicide registered as a hospital disinfectant by the EPA.

As used herein, the term "free," "no," "substantially no" or "substantially free" refers to a composition, mixture, or ingredient that does not contain a particular compound or to which a particular compound or a particular compound-containing compound has not been added. Should the particular compound be present through contamination and/or use in a minimal amount of a composition, mixture, or ingredients, the amount of the compound shall be less than about 3 wt-%. More preferably, the amount of the compound is less than 2 wt-%, less than 1 wt-%, and most preferably the amount of the compound is less than 0.5 wt-%.

As used herein, the term "microorganism" refers to any noncellular or unicellular (including colonial) organism. Microorganisms include all prokaryotes. Microorganisms include bacteria (including cyanobacteria), spores, lichens, fungi, protozoa, virinos, viroids, viruses, phages, and some algae. As used herein, the term "microbe" is synonymous with microorganism.

As used herein, the terms "mixed" or "mixture" when used relating to "percarboxylic acid composition," "percarboxylic acids," "peroxycarboxylic acid composition" or "peroxycarboxylic acids" refer to a composition or mixture including more than one percarboxylic acid or peroxycarboxylic acid.

As used herein, the term "sanitizer" refers to an agent that reduces the number of bacterial contaminants to safe levels as judged by public health requirements. In an embodiment, sanitizers for use in this invention will provide at least a 3 log reduction and more preferably a 5-log order reduction. These reductions can be evaluated using a procedure set out in *Germicidal and Detergent Sanitizing Action of Disinfectants*, Official Methods of Analysis of the Association of Official Analytical Chemists, paragraph 960.09 and applicable sections, 15th Edition, 1990 (EPA Guideline 91-2). According to this reference a sanitizer should provide a 99.999% reduction (5-log order reduction) within 30 seconds at room temperature, 25±2° C., against several test organisms.

Differentiation of antimicrobial "-cidal" or "-static" activity, the definitions which describe the degree of efficacy, and the official laboratory protocols for measuring this efficacy are considerations for understanding the relevance of antimicrobial agents and compositions. Antimicrobial compositions can affect two kinds of microbial cell damage. The first is a lethal, irreversible action resulting in complete microbial cell destruction or incapacitation. The second type of cell damage is reversible, such that if the organism is rendered free of the agent, it can again multiply. The former is termed microbiocidal and the later, microbistatic. A sanitizer and a disinfectant are, by definition, agents which provide antimicrobial or microbiocidal activity. In contrast, a preservative is generally described as an inhibitor or microbistatic composition The term "substantially similar performance" refers generally to achievement by a substitute anti-corrosion product or substitute anti-corrosion system of generally the same degree (or at least not a significantly lesser degree) of corrosion inhibition.

As used herein, the term "sulfoperoxycarboxylic acid," "sulfonated peracid," or "sulfonated peroxycarboxylic acid" refers to the peroxycarboxylic acid form of a sulfonated carboxylic acid. In some embodiments, the sulfonated peracids of the present invention are mid-chain sulfonated peracids. As used herein, the term "mid-chain sulfonated peracid" refers to a peracid compound that includes a sulfonate group attached to a carbon that is at least one carbon (e.g., the three position or further) from the carbon of the percarboxylic acid group in the carbon backbone of the percarboxylic acid chain, wherein the at least one carbon is not in the terminal position. As used herein, the term "terminal position," refers to the carbon on the carbon backbone chain of a percarboxylic acid that is furthest from the percarboxyl group.

As used herein, the term "water" for treatment according to the invention includes a variety of sources, such as freshwater, pond water, sea water, salt water or brine source, brackish water, recycled water, or the like. Waters are also understood to optionally include both fresh and recycled water sources (e.g. "produced waters"), as well as any combination of waters for treatment according to the invention. In some embodiments, produced water (or reuse water) refers to a mixture of water that comprises both water recycled from previous or concurrent oil- and gas-field operations, e.g., fracking, and water that has not been used in oil- and gas-field operations, e.g., fresh water, pond water, sea water, etc.

The term "weight percent," "wt-%," "percent by weight," "% by weight," and variations thereof, as used herein, refer to the concentration of a substance as the weight of that substance divided by the total weight of the composition and multiplied by 100. It is understood that, as used here, "percent," "%," and the like are intended to be synonymous with "weight percent," "wt-%," etc.

The methods, systems, and compositions of the present invention may comprise, consist essentially of, or consist of the components and ingredients of the present invention as well as other ingredients described herein. As used herein, "consisting essentially of" means that the methods, systems, and compositions may include additional steps, components or ingredients, but only if the additional steps, components or ingredients do not materially alter the basic and novel characteristics of the claimed methods, systems, and compositions.

Corrosion Protected Peroxycarboxylic Acids and/or Biocidal Compositions

In an aspect of the invention, an oxidizing or a non-oxidizing biocide composition is employed for biocidal properties and in need of corrosion protection. The oxidizing or non-oxidizing biocide is used in combination with a corrosion inhibitor composition. In an aspect, the corrosion inhibitors are combined with the oxidizing or non-oxidizing biocide at a point of use for corrosion inhibited biocidal activity. In an alternative aspect, the biocide and corrosion inhibitor can be formulated into a combined composition.

Corrosion Inhibitors

The compositions and methods employing the compositions according to the invention are suitable for inhibiting and/or preventing corrosion from a target caused by general and biocide-induced corrosion. In an aspect, the compositions comprise, consist of and/or consist essentially of a corrosion inhibitor. Corrosion inhibitors suitable for use include alkyl pyridinium salts, cetyl pyridinium salts, polyesteramides, dimethicones, propionates and cocoacyl derivatives (which more broadly includes imidazole derivatives), and sulphonamides. While sections of the present disclosure may refer to a "corrosion inhibitor," it is to be understood, unless specified to the contrary, that a "corrosion inhibitor" or "corrosion inhibitor composition" may comprise a single corrosion inhibiting compound or may comprise a mixture of two or more corrosion inhibiting compounds Corrosion inhibitors suitable for use according to the invention for preventing general and namely biocide-induced corrosion include alkyl pyridinium salts, including cetyl pyridinium and its salts. Examples of suitable cetyl pyridinium salts include cetyl pyridinium bromide and cetyl pyridinium chloride. Cetyl pyridinium and its salt corrosion inhibitors may be provided at a percent actives of about 20%, such as commercially-available from Sigma-Aldrich or other commercial chemical suppliers.

Additional corrosion inhibitors suitable for use according to the invention for preventing general and namely biocide-induced corrosion include polyesteramides. An example of a suitable polyesteramide is the hyperbranched polyesteramide, 2,5-Furandione, dihydro-, Polymer with 1,1'-iminobis[2-propanol]) (CAS no: 362603-93-8). In some aspects the polyesteramides have anhydride building blocks, such as the hyperbranched polyesteramide and dodecenyl succinic anhydride. Accordingly, in an aspect, the corrosion inhibitors include anhydride compounds. Anhydride compounds may be provided at a percent actives of about 50%, such as the hyperbranched polyesteramide commercially-available from Sigma-Aldrich or other similar commercial chemical suppliers, or the dodecenyl succinic anhydride commercially-available from Sigma-Aldrich or other similar commercial chemical suppliers.

Additional corrosion inhibitors suitable for use according to the invention for preventing general and namely biocide-induced corrosion include dimethicone compounds. Exemplary dimethicone compounds include polydimethylsiloxanes or polymeric organosilicone compounds. A general formula for polydimethylsiloxanes is $CH_3[Si(CH_3)_2O]_nSi(CH_3)_3$, where n is the number of repeating monomer $[SiO(CH_3)_2]$ units. Examples of suitable dimethicone include cocoglucoside dimethicone and silicone quaternized alkylamido dimethylamine. Such dimethicones are commercially available at percent active ranges of 17.5% and 28.5%, respectively, such as commercially-available from Sigma-Aldrich or other similar commercial chemical suppliers.

Still further corrosion inhibitors suitable for use according to the invention for preventing general and namely biocide-induced corrosion include imidazole derivatives, namely propionates and cocoacyl derivatives. Exemplary imidazole derivatives include long chain imidazole derivatives having the general formula:

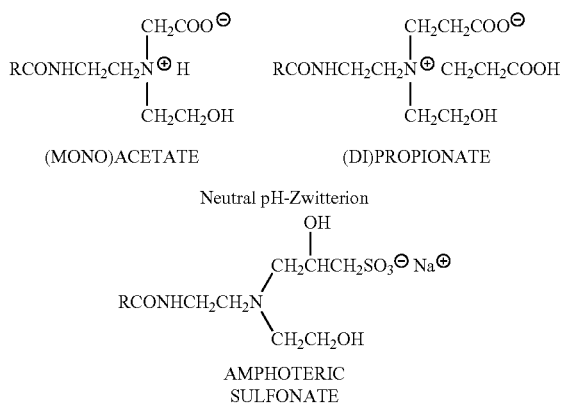

wherein R is an acyclic hydrophobic group containing from about 8 to 18 carbon atoms and M is a cation to neutralize the charge of the anion, generally sodium. In a preferred aspect, the corrosion inhibitor is a propionate and/or cocoacyl derivative. Commercially available imidazoline derivatives include for example: Cocoamphopropionate and its salts thereof, cocoamphodipropionate and its salts thereof, such as cocoamphodiproprionate sodium salt (COCOAP). Other exemplary imidazole derivatives include cocoamphocarboxy-propionate, cocoamphoglycinate, cocoamphocarboxy-glycinate, cocoamphopropyl-sulfonate, and cocoamphocarboxy-propionic acid.

Still further corrosion inhibitors suitable for use according to the invention for preventing general and namely biocide-induced corrosion include sulphonamides. A general formula for a sulphonamide functional group is $-S(=O)_2-NH_2$ where a sulfonyl group is connected to an amine. Exemplary sulphonamides include 2-hydroxylethyl-N-methylbutane-1-sulphonamide. Such sulphonamide is commercially available at percent active ranges of about 24-25%, such as commercially-available from Sigma-Aldrich or other similar commercial chemical suppliers.

The corrosion inhibitor can be used at any suitable concentration. In some embodiments, the corrosion inhibitor has a concentration from about 1 wt-% to about 100 wt-% in a composition or a aqueous system in need of corrosion inhibition. In other embodiments, the corrosion inhibitor has a concentration from about 1 wt-% to about 90 wt-%, or about 10 wt-% to about 90 wt-%. In still other embodiments, the corrosion inhibitor has a concentration at about 10 wt-% to about 90 wt-%, about 20 wt-% to about 90 wt-%, about 30 wt-% to about 90 wt-%, about 40 wt-% to about 90 wt-%, about 50 wt-% to about 90 wt-%, about 60 wt-% to about 90 wt-%, about 70 wt-% to about 90 wt-%, about 80 wt-% to about 90 wt-%, or about 90 wt-%. In still other embodiments, the corrosion inhibitor has a concentration at about 50 wt-% to about 100 wt-% of a corrosion inhibitor composition, at about 50 wt-% to about 90 wt-% of a corrosion inhibitor composition, or at about 70 wt-% to about 90 wt-% of a corrosion inhibitor composition.

In still other aspects, the corrosion inhibitor can be used at any suitable concentration in a aqueous source, such as a water source, in need of corrosion protection caused by general and biocide-induced corrosion. In an aspect, the corrosion inhibitor can be used at a concentration in a aqueous source from about 1 ppm to about 10,000 ppm, preferably from about 1 ppm to about 1,000 ppm, from about 1 ppm to about 500 ppm, from about 1 ppm to about 200 ppm, from about 1 ppm to about 100 ppm, from about 5 ppm to about 100 ppm, or from about 10 ppm to about 100 ppm. For example, the corrosion inhibitor can comprise from about 1 to about 10 ppm, about 10 to about 20 ppm, about 20 to about 30 ppm, about 30 to about 40 ppm, about 40 to about 50 ppm, about 50 to about 60 ppm, about 60 to about 70 ppm, about 70 to about 80 ppm, about 80 to about 90 ppm, about 90 to about 100 ppm, about 100 to about 110 ppm, about 110 to about 120 ppm, about 120 to about 130 ppm, about 130 to about 140 ppm, about 140 to about 150 ppm, about 100 to about 150 ppm, about 150 to about 200 ppm, about 200 to about 250 ppm, about 250 to about 300 ppm, about 300 to about 350 ppm, about 350 to about 400 ppm, about 400 to about 450 ppm, about 450 to about 500 ppm, about 500 to about 550 ppm, about 550 to about 600 ppm, about 600 to about 650 ppm, about 650 to about 700 ppm, about 700 to about 750 ppm, about 750 to about 800 ppm, about 800 to about 850 ppm, about 850 to about 900 ppm, about 900 to about 950 ppm, about 950 to about 1,000 ppm, about 1,000 to about 1,500 ppm, about 1,500 to about 2,000 ppm, about 2,000 to about 2,500 ppm, about 2,500 to about 3,000 ppm, about 3,000 to about 3,500 ppm, about 3,500 to about 4,000 ppm, about 4,000 to about 4,500 ppm, about 4,500 to about 5,000 ppm, about 5,000 to about 5,500 ppm, about 5,500 to about 6,000 ppm, about 6,000 to about 6,500 ppm, about 6,500 to about 7,000 ppm, about 7,000 to about 7,500 ppm, about 7,500 to about 8,000 ppm, about 8,000 to about 8,500 ppm, about 8,500 to about 9,000 ppm, about 9,000 to about 10,000 ppm.

In some embodiments, the ratio between the level of the biocide, such as a peroxycarboxylic acid (w/v) and the level of the corrosion inhibitor (w/v) used in the present method can be from about 0.01 to about 100, e.g., about 0.01 to about 0.05, about 0.05 to about 0.1, about 0.1 to about 0.5, about 0.5 to about 1, about 1 to about 2, about 2 to about 3, about 3 to about 4, about 4 to about 5, about 5 to about 6, about 6 to about 7, about 7 to about 8, about 8 to about 9, about 9 to about 10, about 10 to about 15, about 15 to about 20, about 20 to about 25, about 25 to about 30, about 30 to about 35, about 35 to about 40, about 40 to about 45, about 45 to about 50, about 50 to about 60, about 60 to about 70, about 70 to about 80, about 80 to about 90, about 90 to about 100. In still other embodiments, the corrosion inhibitor can be used at a level that has a synergistic effect with the biocide, namely a peroxycarboxylic acid, to stabilize or reduce microbial population in and/or on the target or the treated target composition. In yet other embodiments, the corrosion inhibitor can be used at a level that reduces acid corrosion in and/or on the target or the treated target composition. In yet other embodiments, the corrosion inhibitor can be used at a level that has a synergistic effect with the biocide, such as a peroxycarboxylic acid, to stabilize or reduce microbial population in and/or on the target or the treated target composition and reduces acid corrosion in and/or on the target or the treated target composition.

Biocide

The compositions and methods employing the compositions according to the invention are suitable for inhibiting and/or preventing corrosion from a target caused by general and biocide-induced corrosion. Biocides suitable for use according to the present invention include both oxidizing and non-oxidizing biocides. Biocides are often classified as oxidizing or non-oxidizing, depending on their chemical composition and mode of action. In an aspect, the compositions comprise, consist of and/or consist essentially of an oxidizing biocide in combination with a corrosion inhibitor. In an alternative aspect, the compositions comprise, consist of and/or consist essentially of a non-oxidizing biocide in combination with a corrosion inhibitor. In an aspect, the biocide is selected from the group consisting of a peroxycarboxylic acid, quaternary phosphonium salts including tetrakis(hydroxymethyl)phosphonium sulfate (THPS), aldehydes including gluteraldehyde compositions, or combinations thereof.

Non-Oxidizing Biocides

In an aspect, the compositions comprise, consist of and/or consist essentially of a non-oxidizing biocide in combination with a corrosion inhibitor. Non-oxidizing biocide useful in the invention include, but are not limited to, aldehydes, formaldehyde releasing compounds, phenolics, amides, halogenated amides, carbamates, heterocyclic compounds containing nitrogen and sulfur atoms in the ring structure, electrophilic active substances having an activated halogen group in the alpha-position and/or in the vinyl position to an electronegative group, nucleophilic active substance having an alkyl group and at least one leaving group, and surface active agents. The aldehyde containing compounds can be linear, branched or aromatic. An example of aldehyde useful in the invention, but is not limited to, glutaraldehyde. The formaldehyde releasing compounds are preferably halogenated, methylated nitro-hydrocarbons. The quaternary phosphonium salts preferably include tetrakis(hydroxymethyl) phosphonium sulfate (THPS).

Oxidizing Biocides

In an aspect, the compositions comprise, consist of and/or consist essentially of an oxidizing biocide in combination with a corrosion inhibitor. Typically when oxidizing biocides are used in microbiological control programs in other process systems they are applied in such a manner as to apply quantities sufficient to maintain a free oxidizer residual in the process. Conventionally, excess of oxidizing biocide are known to corrode the mild steel pipeline making the treatment pointless. The present invention employing a corrosion inhibitor suitable for use with oxidizing biocides overcomes this conventional limitation. A particularly suitable example of an oxidizing biocide is a peroxycarboxylic acid composition or forming composition.

Peroxycarboxylic Acid Compositions

In an aspect, the compositions comprise, consist of and/or consist essentially of a peroxycarboxylic acid composition. In an aspect, the compositions comprise, consist of and/or consist essentially of a peroxycarboxylic acid, carboxylic acid and hydrogen peroxide. Without being limited to a particular mechanism of action the peroxycarboxylic acids suitable for use for the methods of the invention are limited to a particular formula. According to the invention, corrosion inhibition is provided by peroxycarboxylic acids of varying sizes and formulas due to the R—(COOOH) functionality. In an aspect, a molar equivalent of percarboxylic acid, including those of varying chain lengths, is required for corrosion inhibition according to the invention.

Carboxylic Acid

The peroxycarboxylic acid compositions employed according to the invention include a carboxylic acid. A carboxylic acid includes any compound of the formula R—(COOH)n in which R can be hydrogen, alkyl, alkenyl, alkyne, acylic, alicyclic group, aryl, heteroaryl, or heterocylic group, and n is 1, 2, or 3. Preferably R includes hydrogen, alkyl, or alkenyl. The terms "alkyl," "alkenyl," "alkyne," "acylic," "alicyclic group," "aryl," "heteroaryl," and "heterocyclic group" are as defined below with respect to percarboxylic acids.

Examples of suitable carboxylic acids according to the equilibrium systems of the invention include a variety monocarboxylic acids, dicarboxylic acids, and tricarboxylic acids. Monocarboxylic acids include, for example, formic acid, acetic acid, propanoic acid, butanoic acid, pentanoic acid, hexanoic acid, heptanoic acid, octanoic acid, nonanoic acid, decanoic acid, undecanoic acid, dodecanoic acid, glycolic acid, lactic acid, salicylic acid, acetylsalicylic acid, mandelic acid, etc. Dicarboxylic acids include, for example, adipic acid, fumaric acid, glutaric acid, maleic acid, succinic acid, malic acid, tartaric acid, etc. Tricarboxylic acids include, for example, citric acid, trimellitic acid, isocitric acid, agaicic acid, etc.

In an aspect of the invention, a particularly well suited carboxylic acid is water soluble such as formic acid, acetic acid, propionic acid, butanoic acid, lactic acid, glycolic acid, citric acid, mandelic acid, glutaric acid, maleic acid, malic acid, adipic acid, succinic acid, tartaric acid, etc. Preferably a composition of the invention includes acetic acid, octanoic acid, or propionic acid, lactic acid, heptanoic acid, octanoic acid, or nonanoic acid. Additional examples of suitable carboxylic acids are employed in sulfoperoxycarboxylic acid or sulfonated peracid systems, which are disclosed in U.S. Pat. Nos. 8,344,026, 8,809,392, and U.S. Publication No. 2012/0052134, each of which are herein incorporated by reference in their entireties.

Any suitable $C_1$-$C_{22}$ carboxylic acid can be used in the present compositions. In some embodiments, the $C_1$-$C_{22}$ carboxylic acid is a $C_2$-$C_{20}$ carboxylic acid. In other embodiments, the $C_1$-$C_{22}$ carboxylic acid is a $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, or $C_{22}$ carboxylic acid. In still other embodiments, the $C_1$-$C_{22}$ carboxylic acid comprises formic acid, acetic acid, octanoic acid and/or sulfonated oleic acid.

The $C_1$-$C_{22}$ carboxylic acid can be used at any suitable concentration. In some embodiments, the $C_1$-$C_{22}$ carboxylic acid has a concentration from about 10 wt-% to about 90 wt-%. In other embodiments, the $C_1$-$C_{22}$ carboxylic acid has a concentration from about 20 wt-% to about 80 wt-%. In still other embodiments, the $C_1$-$C_{22}$ carboxylic acid has a concentration at about 10 wt-% to about 90 wt-%, at about 20 wt-% to about 90 wt-%, at about 30 wt-% to about 90 wt-%, at about 40 wt-% to about 90 wt-%, at about 50 wt-% to about 90 wt-%, at about 60 wt-% to about 90 wt-%, at about 70 wt-% to about 90 wt-%, at about 80 wt-% to about 90 wt-%, or at about 90 wt-%.

Percarboxylic Acid

The peroxycarboxylic acid compositions employed according to the invention include a percarboxylic acid. A peracid includes any compound of the formula R—(COOOH)n in which R can be hydrogen, alkyl, alkenyl, alkyne, acylic, alicyclic group, aryl, heteroaryl, or heterocyclic group, and n is 1, 2, or 3, and named by prefixing the parent acid with peroxy. Preferably R includes hydrogen, alkyl, or alkenyl. The terms "alkyl," "alkenyl," "alkyne," "acylic," "alicyclic group," "aryl," "heteroaryl," and "heterocyclic group" are as defined herein.

As used herein, the term "alkyl" or "alkyl groups" refers to saturated hydrocarbons having one or more carbon atoms, including straight-chain alkyl groups (e.g., methyl, ethyl, propyl, butyl, pentyl, hexyl, heptyl, octyl, nonyl, decyl, etc.), cyclic alkyl groups (or "cycloalkyl" or "alicyclic" or "carbocyclic" groups) (e.g., cyclopropyl, cyclopentyl, cyclohexyl, cycloheptyl, cyclooctyl, etc.), branched-chain alkyl groups (e.g., isopropyl, tert-butyl, sec-butyl, isobutyl, etc.), and alkyl-substituted alkyl groups (e.g., alkyl-substituted cycloalkyl groups and cycloalkyl-substituted alkyl groups). Unless otherwise specified, the term "alkyl" includes both "unsubstituted alkyls" and "substituted alkyls." As used herein, the term "substituted alkyls" refers to alkyl groups having substituents replacing one or more hydrogens on one or more carbons of the hydrocarbon backbone. Such substituents may include, for example, alkenyl, alkynyl, halogeno, hydroxyl, alkylcarbonyloxy, arylcarbonyloxy, alkoxycarbonyloxy, aryloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), imino, sulfhydryl, alkylthio, arylthio, thiocarboxylate, sulfates, alkylsulfinyl, sulfonates, sulfamoyl, sulfonamido, nitro, trifluoromethyl, cyano, azido, heterocyclic, alkylaryl, or aromatic (including heteroaromatic) groups. In some embodiments, substituted alkyls can include a heterocyclic group. As used herein, the term "heterocyclic group" includes closed ring structures analogous to carbocyclic groups in which one or more of the carbon atoms in the ring is an element other than carbon, for example, nitrogen, sulfur or oxygen. Heterocyclic groups may be saturated or unsaturated. Exemplary heterocyclic groups include, but are not limited to, aziridine, ethylene oxide (epoxides, oxiranes), thiirane (episulfides), dioxirane, azetidine, oxetane, thietane, dioxetane, dithietane, dithiete, azolidine, pyrrolidine, pyrroline, oxolane, dihydrofuran, and furan.

The term "alkenyl" includes an unsaturated aliphatic hydrocarbon chain having from 2 to 12 carbon atoms, such as, for example, ethenyl, 1-propenyl, 2-propenyl, 1-butenyl, 2-methyl-1-propenyl, and the like. The alkyl or alkenyl can be terminally substituted with a heteroatom, such as, for example, a nitrogen, sulfur, or oxygen atom, forming an aminoalkyl, oxyalkyl, or thioalkyl, for example, aminomethyl, thioethyl, oxypropyl, and the like. Similarly, the above alkyl or alkenyl can be interrupted in the chain by a heteroatom forming an alkylaminoalkyl, alkylthioalkyl, or alkoxyalkyl, for example, methylaminoethyl, ethylthiopropyl, methoxymethyl, and the like.

Further, as used herein the term "alicyclic" includes any cyclic hydrocarbyl containing from 3 to 8 carbon atoms. Examples of suitable alicyclic groups include cyclopropanyl, cyclobutanyl, cyclopentanyl, etc. The term "heterocyclic" includes any closed ring structures analogous to carbocyclic groups in which one or more of the carbon atoms in the ring is an element other than carbon (heteroatom), for example, a nitrogen, sulfur, or oxygen atom. Heterocyclic groups may be saturated or unsaturated. Examples of suitable heterocyclic groups include for example, aziridine, ethylene oxide (epoxides, oxiranes), thiirane (episulfides), dioxirane, azetidine, oxetane, thietane, dioxetane, dithietane, dithiete, azolidine, pyrrolidine, pyrroline, oxolane, dihydrofuran, and furan. Additional examples of suitable heterocyclic groups include groups derived from tetrahydrofurans, furans, thiophenes, pyrrolidines, piperidines, pyridines, pyrrols, picoline, coumaline, etc.

In some embodiments, alkyl, alkenyl, alicyclic groups, and heterocyclic groups can be unsubstituted or substituted by, for example, aryl, heteroaryl, $C_{1-4}$ alkyl, $C_{1-4}$ alkenyl, $C_{1-4}$ alkoxy, amino, carboxy, halo, nitro, cyano, —$SO_3H$, phosphono, or hydroxy. When alkyl, alkenyl, alicyclic group, or heterocyclic group is substituted, preferably the substitution is $C_{1-4}$ alkyl, halo, nitro, amido, hydroxy, carboxy, sulpho, or phosphono. In one embodiment, R includes alkyl substituted with hydroxy. The term "aryl" includes aromatic hydrocarbyl, including fused aromatic rings, such as, for example, phenyl and naphthyl. The term "heteroaryl" includes heterocyclic aromatic derivatives having at least one heteroatom such as, for example, nitrogen, oxygen, phosphorus, or sulfur, and includes, for example, furyl, pyrrolyl, thienyl, oxazolyl, pyridyl, imidazolyl, thiazolyl, isoxazolyl, pyrazolyl, isothiazolyl, etc. The term "heteroaryl" also includes fused rings in which at least one ring is aromatic, such as, for example, indolyl, purinyl, benzofuryl, etc.

In some embodiments, aryl and heteroaryl groups can be unsubstituted or substituted on the ring by, for example, aryl, heteroaryl, alkyl, alkenyl, alkoxy, amino, carboxy, halo, nitro, cyano, —$SO_3H$, phosphono, or hydroxy. When aryl, aralkyl, or heteroaryl is substituted, preferably the substitution is $C_{1-4}$ alkyl, halo, nitro, amido, hydroxy, carboxy, sulpho, or phosphono. In one embodiment, R includes aryl substituted with $C_{1-4}$ alkyl.

The peroxycarboxylic acid compositions suitable for use according to the invention can include any C1-C22 peroxycarboxylic acid, including mixtures of peroxycarboxylic acids, including for example, peroxyformic acid, peroxyacetic acid, peroxyoctanoic acid and/or peroxysulfonated oleic acid. As used herein, the term "peracid" may also be referred to as a "percarboxylic acid," "peroxycarboxylic acid" or "peroxyacid."

Sulfoperoxycarboxylic acids, sulfonated peracids and sulfonated peroxycarboxylic acids are also included within the terms "peroxycarboxylic acid" and "peracid" as used herein. The terms "sulfoperoxycarboxylic acid," "sulfonated peracid," or "sulfonated peroxycarboxylic acid" refers to the peroxycarboxylic acid form of a sulfonated carboxylic acid as disclosed in U.S. Pat. Nos. 8,344,026 and 8,809,392, and U.S. Patent Publication No. 2012/0052134, each of which are incorporated herein by reference in their entirety. As one of skill in the art appreciates, a peracid refers to an acid having the hydrogen of the hydroxyl group in carboxylic acid replaced by a hydroxy group. Oxidizing peracids may also be referred to herein as peroxycarboxylic acids.

In some embodiments, a peroxycarboxylic acid includes at least one water-soluble peroxycarboxylic acid in which R includes alkyl of 1-22 carbon atoms. For example, in one embodiment, a peroxycarboxylic acid includes peroxyformic acid and/or peroxyacetic acid. In another embodiment, a peroxycarboxylic acid has R that is an alkyl of 1-22 carbon atoms substituted with hydroxy.

In some embodiments, a peroxycarboxylic acid is a sulfoperoxycarboxylic acid and has the following formula:

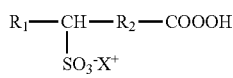

wherein $R_1$ is hydrogen, or a substituted or unsubstituted alkyl group; $R_2$ is a substituted or unsubstituted alkylene group; X is hydrogen, a cationic group, or an ester forming moiety; or salts or esters thereof.

In some embodiments, a sulfoperoxycarboxylic acid is combined with a single or mixed peroxycarboxylic acid composition, such as a sulfoperoxycarboxylic acid with peroxyacetic acid and peroxyoctanoic acid.

In some embodiments, a mixed peracid is employed, such as a peroxycarboxylic acid including at least one peroxycarboxylic acid of limited water solubility in which R includes alkyl of 5-22 carbon atoms and at least one water-soluble peroxycarboxylic acid in which R includes alkyl of 1-4 carbon atoms. For example, in one embodiment, a peroxycarboxylic acid includes peroxyacetic acid and at least one other peroxycarboxylic acid such as those named above. Preferably a composition of the invention includes peroxyformic acid, peroxyacetic acid and/or peroxyoctanoic acid. Other combinations of mixed peracids are well suited for use in the current invention.

In some embodiments, a mixture of peroxyformic acid, and peracetic acid or peroctanoic acid is used to treat a water source, such as disclosed in U.S. Pat. No. 5,314,687 which is herein incorporated by reference in its entirety. In an aspect, the peracid mixture is a hydrophilic peroxyformic acid or peracetic acid and a hydrophobic peroctanoic acid. In some aspects, a synergistic combination of a mixed peracid system allows the use of lower dosages of the peracids according to methods of the invention.

In some embodiments, a tertiary peracid mixture composition, such as peroxysulfonated oleic acid, peroxyformic acid and peroctanoic acid are used to treat a water source, such as disclosed in U.S. Patent Publication No. 2010/00021557 which is incorporated herein by reference in its entirety. In some aspects, a synergistic combination of a mixed peracid system allows the use of lower dosages of the peracids according to methods of the invention.

Various commercial formulations of peracids are available, including for example, peracetic acid (15%) available as EnviroSan (Ecolab Inc., St. Paul Minn.). Most commercial peracid solutions state a specific percarboxylic acid concentration without reference to the other chemical components in a use solution. However, it should be understood that commercial products, such as peracetic acid, will also contain the corresponding carboxylic acid (e.g. acetic acid), hydrogen peroxide and water.

Any suitable $C_1$-$C_{22}$ percarboxylic acid can be used in the present compositions. In some embodiments, the $C_1$-$C_{22}$ percarboxylic acid is a $C_2$-$C_{20}$ percarboxylic acid. In other embodiments, the $C_1$-$C_{22}$ percarboxylic is a $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, or $C_{22}$ percarboxylic acid. In still other embodiments, the $C_1$-$C_{22}$ percarboxylic acid comprises peroxyformic acid, peroxyacetic acid, peroxyoctanoic acid and/or peroxysulfonated oleic acid.

The $C_1$-$C_{22}$ percarboxylic acid can be used at any suitable concentration. In some embodiments, the $C_1$-$C_{22}$ percarboxylic acid has a concentration from about 1 wt-% to about 40 wt-%. In other embodiments, the $C_1$-$C_{22}$ percarboxylic acid has a concentration from about 1 wt-% to about 20 wt-%. In still other embodiments, the $C_1$-$C_{22}$ percarboxylic acid has a concentration at about 1 wt-% to about 20 wt-%, about 2 wt-% to about 20 wt-%, about 5 wt-% to about 20 wt-%, about 10 wt-% to about 20 wt-%, about 15 wt-% to about 20 wt-%, about 15 wt-% to about 40 wt-%, about 20 wt-% to about 40 wt-%, about 25 wt-% to about 40 wt-%, about 30 wt-% to about 40 wt-%, or about 35 wt-% to about 40 wt-%. In still other embodiments, the $C_1$-$C_{22}$ percarboxylic acid has a concentration at about 1 wt-%, 2 wt-%, 3 wt-%, 4 wt-%, 5 wt-%, 6 wt-%, 7 wt-%, 8 wt-%, 9 wt-%, 10 wt-%, 11 wt-%, 12 wt-%, 13 wt-%, 14 wt-%, 15 wt-%, 16 wt-%, 17 wt-%, 18 wt-%, 19 wt-%, 20 wt-%, 25 wt-%, 30 wt-%, 35 wt-%, or 40 wt-%. In yet other embodiments, the $C_1$-$C_{22}$ percarboxylic acid has a concentration from about 0.1 ppm to about 10,000 ppm or greater, up to about 50,000 ppm, e.g., about 0.1 to about 1 ppm, about 1 to about 10 ppm, about 10 to about 20 ppm, about 20 to about 30 ppm, about 30 to about 40 ppm, about 40 to about 50 ppm, about 50 to about 60 ppm, about 60 to about 70 ppm, about 70 to about 80 ppm, about 80 to about 90 ppm, about 90 to about 100 ppm, about 100 to about 150 ppm, about 150 to about 200 ppm, about 200 to about 250 ppm, about 250 to about 300 ppm, about 300 to about 350 ppm, about 350 to about 400 ppm, about 400 to about 450 ppm, about 450 to about 500 ppm, about 500 to about 550 ppm, about 550 to about 600 ppm, about 600 to about 650 ppm, about 650 to about 700 ppm, about 700 to about 750 ppm, about 750 to about 800 ppm, about 800 to about 850 ppm, about 850 to about 900 ppm, about 900 to about 950 ppm, about 950 to about 1,000 ppm, about 1,000 to about 1,500 ppm, about 1,500 to about 2,000 ppm, about 2,000 to about 2,500 ppm, about 2,500 to about 3,000 ppm, about 3,000 to about 3,500 ppm, about 3,500 to about 4,000 ppm, about 4,000 to about 4,500 ppm, or about 4,500 to about 5,000 ppm, about 5,000 to about 5,500 ppm, about 5,500 to about 6,000 ppm, about 6,000 to about 6,500 ppm, about 6,500 to about 7,000 ppm, about 7,000 to about 7,500 ppm, about 7,500 to about 8,000 ppm, about 8,000 to about 8,500 ppm, about 8,500 to about 9,000 ppm, about 9,000 to about 9,500 ppm, or about 9,500 to about 10,000 ppm.

Hydrogen Peroxide

The peroxycarboxylic acid compositions employed according to the invention include hydrogen peroxide. Hydrogen peroxide, $H_2O_2$, provides the advantages of having a high ratio of active oxygen because of its low molecular weight (34.014 g/mole) and being compatible with numerous substances that can be treated by methods of the invention because it is a weakly acidic, clear, and colorless liquid. Another advantage of hydrogen peroxide is that it decomposes into water and oxygen. It is advantageous to have these decomposition products because they are generally compatible with substances being treated. For example, the decomposition products are generally compatible with metallic substance (e.g., substantially noncorrosive) and are generally innocuous to incidental contact and are environmentally friendly.

In one aspect of the invention, hydrogen peroxide is initially in a peracid composition in an amount effective for maintaining an equilibrium between a carboxylic acid, hydrogen peroxide, a solvent such as water, and a peracid. The amount of hydrogen peroxide should not exceed an amount that would adversely affect the antimicrobial or other (e.g. corrosion inhibiting) activity of a composition of the invention. In further aspects of the invention, hydrogen peroxide concentration is significantly reduced within a peracid composition, preferably containing hydrogen peroxide at or below concentration 1.5 times lower than the concentration of percarboxylic acid in solution. That is, the concentration of hydrogen peroxide is minimized, such as through the use of a selected catalase or peroxidase enzymes as disclosed in U.S. Patent Publication No. 2014/0097144, which is herein incorporated by reference in its entirety. In further aspects, the concentration of hydrogen peroxide is reduced and/or eliminated as a result of distilled equilibrium peracid compositions, other catalysts for hydrogen peroxide decomposition (e.g. biomimetic complexes) and/or the use of anionic perhydrolysis of esters (e.g. triacetin) to obtain peracids with very low hydrogen peroxide.

The hydrogen peroxide can be used at any suitable concentration. In some embodiments, the hydrogen peroxide has a concentration from about 0.5 wt-% to about 25 wt-%, or about 0.5 wt-% to about 15 wt-%, or about 0.5 wt-% to about 10 wt-%. In other embodiments, the hydrogen peroxide has a concentration from about 1 wt-% to about 2 wt-%. In still other embodiments, the hydrogen peroxide has a concentration at about 0.5 wt-%, about 1 wt-%, about 2 wt-%, about 3 wt-%, about 4 wt-%, about 5 wt-%, about 6 wt-%, about 7 wt-%, about 8 wt-%, about 9 wt-%, or about 10 wt-%. In yet other embodiments, the hydrogen peroxide has a concentration at about 1 wt-%, about 1.1 wt-%, about 1.2 wt-%, about 1.3 wt-%, about 1.4 wt-%, about 1.5 wt-%, about 1.6 wt-%, about 1.7 wt-%, about 1.8 wt-%, about 1.9 wt-%, about 2 wt-%, about 2.1 wt-%, about 2.2 wt-%, about 2.3 wt-%, about 2.4 wt-%, about 2.5 wt-%, about 2.6 wt-%, about 2.7 wt-%, about 2.8 wt-%, about 2.9 wt-%, about 3 wt-%, about 3.1 wt-%, about 3.2 wt-%, about 3.3 wt-%, 3.4 wt-%, about 3.5 wt-%, about 3.6 wt-%, about 3.7 wt-%, about 3.8 wt-%, about 3.9 wt-%, or about 4 wt-%.

Peroxycarboxylic Acid Forming Compositions

The compositions and methods employing the compositions according to the invention are suitable for inhibiting corrosion from a target, often within a water source, caused by general and biocide-induced corrosion. In an aspect, the compositions comprise, consist of and/or consist essentially of a peroxycarboxylic acid forming composition. In one aspect, the present invention is directed to a peroxycarboxylic acid forming composition comprising: a first reagent that comprises an ester of a polyhydric alcohol and a carboxylic acid, and a second reagent that comprises hydrogen peroxide or that comprises a substance that generates hydrogen peroxide when in contact with a liquid. In a further aspect, the first reagent and second reagent are kept separately prior to use and combined when it is time to generate the peroxycarboxylic acid.

In a still further aspect, the first reagent and second reagent are configured to be contacted with each other to form a liquid that comprises a peroxycarboxylic acid and has a pH ranging from about 0 to about 11, and pH of the formed liquid becomes about 8 or lower within about 1 minute after the contact between said first reagent and said second reagent. In an alternative aspect, the second reagent comprises a substance that generates hydrogen peroxide when in contact with a liquid, the first reagent and second reagent are comprised in a solid composition, and when it is time to generate the peroxycarboxylic acid, the solid composition is configured to be contacted with a liquid to form a liquid that comprises the peroxycarboxylic acid and has a pH ranging from about 0 to about 11, and pH of the formed liquid becomes about 8 or lower within about 1 minute after the contact between said solid composition and said liquid.

Esters of polyhydric alcohols and a $C_1$-$C_{22}$ carboxylic acid are included in the first reagent. A polyhydric alcohol refers to an molecule with two or more hydroxyl (—OH) groups. An ester of a polyhydric alcohol and a carboxylic acid refers to an ester formed between a polyhydric alcohol and the carboxylic acid. A variety of carboxylic acids can be included. Carboxylic acids generally have the formula R(COOH)n, where, for example, R is an alkyl, aryl alkyl, cycloalkyl, aromatic, or heterocyclic group, and n is one, two, or three.

In an embodiment the polyhydric alcohol may include a sugar alcohol. In an embodiment where the peroxycarboxylic acid is peroxyformic, the first reagent may comprise glycerol formates, pentaerythritol formates, mannitol formates, propylene glycol formates, sorbitol formates and sugar formates. In such an exemplary embodiment, any suitable sugar formats may be employed, e.g., sucrose formates, dextrin formates, maltodextrin formates, or starch formates.

The compositions can also include more than one or a mixture of esters of a polyhydric alcohol and a carboxylic acid. For example, in some embodiments, the compositions include two, three or four esters. When more than one ester is present, the esters can be different. For example, in some embodiments, the compositions can include a first ester of a polyhydric alcohol and a C1 to C4 carboxylic acid, and a second ester of a polyhydric alcohol and a C5 to C11 carboxylic acid. For further example, in some embodiments, the compositions can include a first ester of a polyhydric alcohol and a C1 to C18 carboxylic acid in a mono, di or tri-formation, and a second ester of a polyhydric alcohol and a C1 to C18 carboxylic acid in a mono, di or tri-formation. One skilled in the art will appreciate the various combinations of esters that can be used for the compositions according to the invention.

The use of various forms of an ester (e.g. mono, di and/or tri-formations) to comprise a mixture of esters will impact the peracid yield of a particular composition according to the invention. For example, the various forms of the ester will have different kinetics in generating the peracids according to the methods of the invention. For example, in one aspect, a monooctanoate glycerol ester is faster in generating peracid than the di- or trioctanoate glycerol esters. In addition, the selection of the various forms of an ester will be further impacted by the water solubility of the compositions and whether any additional ingredients are combined to affect solubility (e.g. solvents) that would favor the use of less soluble ester forms (e.g. tri-formations). Accordingly, one skilled in the art of reaction kinetics will ascertain the benefits of using various combinations or mixtures of esters according to the compositions and methods of the invention.

Examples of suitable carboxylic acids include, but are not limited to, formic, acetic, propionic, butanoic, pentanoic, hexanoic, heptanoic, octanoic, nonanoic, decanoic, undecanoic, dodecanoic, as well as their branched isomers, lactic, maleic, ascorbic, citric, hydroxyacetic, neopentanoic, neoheptanoic, neodecanoic, oxalic, malonic, succinic, glutaric, adipic, pimelic subric acid, and mixtures thereof.

The peroxycarboxylic acid forming compositions can comprise any suitable level of an ester of a polyhydric alcohol and carboxylic acid (including either liquid or solid reagents). For example, the first reagent of the peroxycarboxylic acid forming composition can comprise any suitable level of an ester of a polyhydric alcohol and carboxylic acid. In some embodiments, the first reagent can comprise from about 10 ppm to about 500,000 ppm of an ester of a polyhydric alcohol and carboxylic acid. For example, the first reagent can comprise from about 10 to about 20 ppm, about 20 to about 30 ppm, about 30 to about 40 ppm, about 40 to about 50 ppm, about 50 to about 60 ppm, about 60 to about 70 ppm, about 70 to about 80 ppm, about 80 to about 90 ppm, about 90 to about 100 ppm, about 100 to about 150 ppm, about 150 to about 200 ppm, about 200 to about 250 ppm, about 250 to about 300 ppm, about 300 to about 350 ppm, about 350 to about 400 ppm, about 400 to about 450 ppm, about 450 to about 500 ppm, about 500 to about 550 ppm, about 550 to about 600 ppm, about 600 to about 650 ppm, about 650 to about 700 ppm, about 700 to about 750 ppm, about 750 to about 800 ppm, about 800 to about 850 ppm, about 850 to about 900 ppm, about 900 to about 950 ppm, about 950 to about 1,000 ppm, about 1,000 to about 1,500 ppm, about 1,500 to about 2,000 ppm, about 2,000 to about 2,500 ppm, about 2,500 to about 3,000 ppm, about 3,000 to about 3,500 ppm, about 3,500 to about 4,000 ppm, about 4,000 to about 4,500 ppm, or about 4,500 to about 5,000 ppm, about 5,000 to about 5,500 ppm, about 5,500 to about 6,000 ppm, about 6,000 to about 6,500 ppm, about 6,500 to about 7,000 ppm, about 7,000 to about 7,500 ppm, about 7,500 to about 8,000 ppm, about 8,000 to about 8,500 ppm, about 8,500 to about 9,000 ppm, about 9,000 to about 9,500 ppm, about 9,500 to about 10,000 ppm, about 10,000 to about 20,000 ppm, about 20,000 to about 30,000 ppm, about 30,000 to about 40,000 ppm, about 40,000 to about 50,000 ppm, about 50,000 to about 60,000 ppm, about 60,000 to about 70,000 ppm, about 70,000 to about 80,000 ppm, about 80,000 to about 90,000 ppm, about 90,000 to about 100,000 ppm, about 100,000 to about 150,000 ppm, about 150,000 to about 200,000 ppm, about 200,000 to about 250,000 ppm, about 250,000 to about 300,000 ppm, about 300,000 to about 350,000 ppm, about 350,000 to about 400,000 ppm, about 400,000 to about 450,000 ppm, or about 450,000 to about 500,000 ppm. In other embodiments, the first reagent can comprise from about 50 ppm to about 40,000 ppm of an ester of a polyhydric alcohol and carboxylic acid, e.g., about 50 to about 100, about 50 to about 500, about 50 to about 1,000, about 50 to about 1,500, about 50 to about 2,000, about 50 to about 2,500, about 50 to about 3,000, about 50 to about 3,500, about 50 to about 4,000, about 50 to about 4,500, about 50 to about 5,000, about 50 to about 10,000, about 50 to about 20,000, about 50 to about 30,000, or about 50 to about 40,000 ppm of an ester of a polyhydric alcohol and carboxylic acid.

Hydrogen peroxide is employed in the second reagent. The peroxycarboxylic acid forming compositions can comprise any suitable level of hydrogen peroxide or a substance that generates hydrogen peroxide upon contact with a liquid. For example, the second reagent of the peroxycarboxylic acid forming composition can comprise any suitable level of hydrogen peroxide. In some embodiments, the second reagent can comprise about 1 ppm to about 300,000 ppm of hydrogen peroxide. For example, the second reagent can comprise from about 1 to about 10 ppm, 10 to about 20 ppm, 20 to about 30 ppm, 30 to about 40 ppm, 40 to about 50 ppm, 50 to about 60 ppm, 60 to about 70 ppm, 70 to about 80 ppm, 80 to about 90 ppm, 90 to about 100 ppm, 100 to about 150 ppm, 150 to about 200 ppm, 200 to about 250 ppm, 250 to about 300 ppm, 300 to about 350 ppm, 350 to about 400 ppm, 400 to about 450 ppm, 450 to about 500 ppm, 500 to about 550 ppm, 550 to about 600 ppm, 600 to about 650 ppm, 650 to about 700 ppm, 700 to about 750 ppm, 750 to about 800 ppm, 800 to about 850 ppm, 850 to about 900 ppm, 900 to about 950 ppm, 950 to about 1,000 ppm, 1,000 to about 1,500 ppm, 1,500 to about 2,000 ppm, 2,000 to about 2,500 ppm, 2,500 to about 3,000 ppm, 3,000 to about 3,500 ppm, 3,500 to about 4,000 ppm, 4,000 to about 4,500 ppm, 4,500 to about 5,000 ppm, 5,000 to about 5,500 ppm, 5,500 to about 6,000 ppm, 6,000 to about 6,500 ppm, 6,500 to about 7,000 ppm, 7,000 to about 7,500 ppm, 7,500 to about 8,000 ppm, 8,000 to about 8,500 ppm, 8,500 to about 9,000 ppm, 9,000 to about 10,000 ppm, 10,000 to about 20,000 ppm, 20,000 to about 30,000 ppm, 30,000 to about 40,000 ppm, 40,000 to about 50,000 ppm, 50,000 to about 60,000 ppm, 60,000 to about 70,000 ppm, 70,000 to about 80,000 ppm, 80,000 to about 90,000 ppm, or 90,000 to about 100,000 ppm, 100,000 to about 150,000 ppm, 150,000 to about 200,000 ppm, 200,000 to about 250,000 ppm, or 250,000 to about 300,000 ppm hydrogen peroxide. In other embodiments, the second reagent comprises from about 150 ppm to about 50,000 ppm of hydrogen peroxide, e.g., about 150 to about 200, 150 to about 300, 150 to about 400, 150 to about 500, 150 to about 600, 150 to about 700, 150 to about 800, 150 to about 900, 150 to about 1,000, 150 to about 1,500, 150 to about 2,000, 150 to about 2,500, 150 to about 3,000, 150 to about 3,500, 150 to about 4,000, 150 to about 4,500, 150 to about 5,000, 150 to about 10,000, 50 to about 20,000, 50 to about 30,000, 50 to about 40,000 or 50 to about 50,000 ppm of hydrogen peroxide.

In a further aspect, a substance that generates hydrogen peroxide when in contact with a liquid may be used for the second reagent instead of hydrogen peroxide. In an aspect employing a substance to generate hydrogen peroxide, the solid composition can comprise a substance at an amount that generates from about 1 ppm to about 100,000 ppm of hydrogen peroxide upon contact with a liquid. For example, the solid composition can comprise a substance at an amount that generates from about 1 to about 10 ppm, 10 to about 20 ppm, 20 to about 30 ppm, 30 to about 40 ppm, 40 to about 50 ppm, 50 to about 60 ppm, 60 to about 70 ppm, 70 to about 80 ppm, 80 to about 90 ppm, 90 to about 100 ppm, 100 to about 150 ppm, 150 to about 200 ppm, 200 to about 250 ppm, 250 to about 300 ppm, 300 to about 350 ppm, 350 to about 400 ppm, 400 to about 450 ppm, 450 to about 500 ppm, 500 to about 550 ppm, 550 to about 600 ppm, 600 to about 650 ppm, 650 to about 700 ppm, 700 to about 750 ppm, 750 to about 800 ppm, 800 to about 850 ppm, 850 to about 900 ppm, 900 to about 950 ppm, 950 to about 1,000 ppm, 1,000 to about 1,500 ppm, 1,500 to about 2,000 ppm, 2,000 to about 2,500 ppm, 2,500 to about 3,000 ppm, 3,000 to about 3,500 ppm, 3,500 to about 4,000 ppm, 4,000 to about 4,500 ppm, 4,500 to about 5,000 ppm, 5,000 to about 5,500 ppm, 5,500 to about 6,000 ppm, 6,000 to about 6,500 ppm, 6,500 to about 7,000 ppm, 7,000 to about 7,500 ppm, 7,500 to about 8,000 ppm, 8,000 to about 8,500 ppm, 8,500 to about 9,000 ppm, 9,000 to about 10,000 ppm, 10,000 to about 20,000 ppm, 20,000 to about 30,000 ppm, 30,000 to about 40,000 ppm, 40,000 to about 50,000 ppm, 50,000 to about 60,000 ppm, 60,000 to about 70,000 ppm, 70,000 to about 80,000 ppm, 80,000 to about 90,000 ppm, or 90,000 to about 100,000 ppm hydrogen peroxide.

The first or second reagent and the generated liquid peroxycarboxylic acid composition can have any suitable pH range. For example, the first or second reagent and the generated liquid peroxycarboxylic acid composition can have a pH ranging from about 0 to about 11, e.g., about 0 to about 1, 0 to about 2, 0 to about 3, 0 to about 4, 0 to about 5, 0 to about 6, 0 to about 7, 0 to about 8, 0 to about 9, 0 to about 10, 0 to about 11, 1 to about 2, 1 to about 3, 1 to about 4, 1 to about 5, 1 to about 6, 1 to about 7, 1 to about 8, 1 to about 9, 1 to about 10, 1 to about 11, 2 to about 3, 2 to about 4, 2 to about 5, 2 to about 6, 2 to about 7, 2 to about 8, 2 to about 9, 2 to about 10, 2 to about 11, 3 to about 4, 3 to about 5, 3 to about 6, 3 to about 7, 3 to about 8, 3 to about 9, 3 to about 10, 3 to about 11, 4 to about 5, 4 to about 6, 4 to about 7, 4 to about 8, 4 to about 9, 4 to about 10, 4 to about 11, 5 to about 6, 5 to about 7, 5 to about 8, 5 to about 9, 5 to about 10, 5 to about 11, 6 to about 7, 6 to about 8, 6 to about 9, 6 to about 10, 6 to about 11, 6 to about 7, 7 to about 8, 7 to about 9, 7 to about 10, 7 to about 11, 8 to about 9, 8 to about 10, 8 to about 11, 9 to about 10, 9 to about 11, 10 to about 11, or at about 0, 1, 2, 3, 4, 5, 6, 7, 8, 9, 10 or 11. In some embodiments, the first or second reagent and the generated liquid peroxycarboxylic acid composition has a pH ranging from about 5 to about 10, e.g., about 5 to about 6, 5 to about 7, 5 to about 8, 5 to about 9, 5 to about 10, 6 to about 7, 6 to about 8, 6 to about 9, 6 to about 10, 7 to about 8, 7 to about 9, 7 to about 10, 8 to about 9, 8 to about 10, or 9 to about 10. In other embodiments, the first or second reagent has a pH at about 9. In other embodiments, the first reagent and the second reagent are configured to be contacted with each other to form a liquid peroxycarboxylic acid and has a pH at about 9.

The first reagent and the second reagent can be configured to be contacted with each other to form a liquid peroxycarboxylic acid under any suitable conditions or temperature. In some embodiments, the first reagent and the second reagent are configured to be contacted with each other under ambient conditions. In other embodiments, the first reagent and the second reagent are configured to be contacted with each at a temperature ranging from about 4° C. to about 60° C., e.g., about 4° C. to about 5° C., 5° C. to about 10° C., 10° C. to about 15° C., 15° C. to about 20° C., 20° C. to about 25° C., 25° C. to about 30° C., 30° C. to about 35° C., 35° C. to about 40° C., 40° C. to about 45° C., 45° C. to about 50° C., 50° C. to about 55° C., or 55° C. to about 60° C. In still other embodiments, the first reagent and the second reagent are configured to be contacted with each other to form a liquid peroxycarboxylic acid at a temperature at about 4° C. or lower than 4° C., e.g., at about 3° C., 2° C., 1° C., 0° C., or lower than 0° C.

The peroxycarboxylic acid forming compositions can be configured to form a liquid, e.g., a solution, that comprises any suitable level of the peroxycarboxylic acid. For example, the first reagent and the second reagent in the peroxycarboxylic acid forming compositions can be configured to be contacted with each other to form a liquid and/or solid, e.g., a solution, that comprises any suitable level of the peroxycarboxylic acid. In some embodiments, the first reagent and the second reagent can be configured to be contacted with each other to form a liquid, e.g., a solution, that comprises from about 0.1 ppm to about 5,000 ppm of peroxycarboxylic acid, e.g., about 0.1 to about 1 ppm, 1 to about 10 ppm, 10 to about 20 ppm, 20 to about 30 ppm, 30 to about 40 ppm, 40 to about 50 ppm, 50 to about 60 ppm, 60 to about 70 ppm, 70 to about 80 ppm, 80 to about 90 ppm, 90 to about 100 ppm, 100 to about 150 ppm, 150 to about 200 ppm, 200 to about 250 ppm, 250 to about 300 ppm, 300 to about 350 ppm, 350 to about 400 ppm, 400 to about 450 ppm, 450 to about 500 ppm, 500 to about 550 ppm, 550 to about 600 ppm, 600 to about 650 ppm, 650 to about 700 ppm, 700 to about 750 ppm, 750 to about 800 ppm, 800 to about 850 ppm, 850 to about 900 ppm, 900 to about 950 ppm, 950 to about 1,000 ppm, 1,000 to about 1,500 ppm, 1,500 to about 2,000 ppm, 2,000 to about 2,500 ppm, 2,500 to about 3,000 ppm, 3,000 to about 3,500 ppm, 3,500 to about 4,000 ppm, 4,000 to about 4,500 ppm, or 4,500 to about 5,000 ppm of peroxycarboxylic acid. In other embodiments, the first reagent and the second reagent can be configured to be contacted with each other to form a liquid, e.g., a solution, that comprises from about 1 ppm to about 500 ppm of peroxycarboxylic acid, e.g., about 0.1 to about 1 ppm, 0.1 to about 10 ppm, 0.1 to about 20 ppm, 0.1 to about 30 ppm, 0.1 to about 40 ppm, 0.1 to about 50 ppm, 0.1 to about 60 ppm, 0.1 to about 70 ppm, 0.1 to about 80 ppm, 0.1 to about 90 ppm, 0.1 to about 100 ppm, 0.1 to about 150 ppm, 0.1 to about 200 ppm, 0.1 to about 250 ppm, 0.1 to about 300 ppm, 0.1 to about 350 ppm, 0.1 to about 400 ppm, 0.1 to about 450 ppm, 0.1 to about 500 ppm of peroxycarboxylic acid. In still other embodiments, the first reagent and the second reagent can be configured to be contacted with each other to form a liquid, e.g., a solution, that comprises from about 50 ppm to about 100 ppm of peroxycarboxylic acid, e.g., about 50 to about 60 ppm, 60 to about 70 ppm, 70 to about 80 ppm, 80 to about 90 ppm or 90 to about 100 ppm of peroxycarboxylic acid.

In another example, the solid composition can be configured to be contacted with a liquid to form a solution that comprises from about 0.1 ppm to about 5,000 ppm of peroxycarboxylic acid. In some embodiments, the solid composition can be configured to be contacted with a liquid to form a liquid, e.g., a solution, that comprises from about 0.1 ppm to about 5,000 ppm of peroxycarboxylic acid, e.g., about 0.1 to about 1 ppm, 1 to about 10 ppm, 10 to about 20 ppm, 20 to about 30 ppm, 30 to about 40 ppm, 40 to about 50 ppm, 50 to about 60 ppm, 60 to about 70 ppm, 70 to about 80 ppm, 80 to about 90 ppm, 90 to about 100 ppm, 100 to about 150 ppm, 150 to about 200 ppm, 200 to about 250 ppm, 250 to about 300 ppm, 300 to about 350 ppm, 350 to about 400 ppm, 400 to about 450 ppm, 450 to about 500 ppm, 500 to about 550 ppm, 550 to about 600 ppm, 600 to about 650 ppm, 650 to about 700 ppm, 700 to about 750 ppm, 750 to about 800 ppm, 800 to about 850 ppm, 850 to about 900 ppm, 900 to about 950 ppm, 950 to about 1,000 ppm, 1,000 to about 1,500 ppm, 1,500 to about 2,000 ppm, 2,000 to about 2,500 ppm, 2,500 to about 3,000 ppm, 3,000 to about 3,500 ppm, 3,500 to about 4,000 ppm, 4,000 to about 4,500 ppm, or 4,500 to about 5,000 ppm of peroxycarboxylic acid.

The peroxycarboxylic acid forming compositions (liquids or solids) can be configured to form the resultant compositions comprising any suitable level of peroxycarboxylic acid within any suitable time. In some embodiments, the first reagent and the second reagent can be configured to be contacted with each other to form the peroxycarboxylic acid composition that comprises at least about 1 ppm peroxycarboxylic acid within 1 minute of the contact time, e.g., at least about 1 ppm, 2 ppm, 3 ppm, 4 ppm, 5 ppm, 6 ppm, 7 ppm, 8 ppm, 9 ppm, 10 ppm, 15 ppm, 20 ppm, 25 ppm, 30 ppm, 35 ppm, 40 ppm, 45 ppm, 50 ppm, 55 ppm, 60 ppm, 65 ppm, 70 ppm, 75 ppm, 80 ppm, 85 ppm, 90 ppm, 95 ppm, 100 ppm, 200 ppm, 300 ppm, 400 ppm, 500 ppm, 600 ppm, 700 ppm, 800 ppm, 900 ppm, 1,000 ppm, 2,000 ppm, 3,000 ppm, 4,000 ppm, or 5,000 ppm of peroxycarboxylic acid within 1 minute, within 5 minutes, within 10 minutes, or greater of the contact time.

The peroxycarboxylic acid forming compositions can include any C1-C22 peroxycarboxylic acid, including mixtures of peroxycarboxylic acids, including for example, peroxyformic acid, peroxyacetic acid, peroxyoctanoic acid and/or peroxysulfonated oleic acid.

Oxidizing biocide compositions including peroxycarboxylic acid composition can include various formulations, such as set forth in the Table 1A below.

TABLE 1A

| | First Exemplary Embodiment (wt-%) | Second Exemplary Embodiment (wt-%) | Third Exemplary Embodiment (wt-%) |
|---|---|---|---|
| $C_1$-$C_{22}$ Percarboxylic acid | 1-60 | 1-40 | 1-20 |
| $C_1$-$C_{22}$ Carboxylic acid | 10-90 | 20-80 | 30-70 |
| Hydrogen Peroxide | 0.5-25 | 0.5-10 | 0.5-2 |
| Additional Functional Ingredients | 0-25 | 0.01-10 | 0.5-10 |

Oxidizing biocide compositions including peroxycarboxylic acid forming composition can include various formulations, such as set forth in the Table 1B below.

TABLE 1B

| | First Exemplary Embodiment (wt-%) | Second Exemplary Embodiment (wt-%) | Third Exemplary Embodiment (wt-%) |
|---|---|---|---|
| Ester of Polyhydric Alcohol and $C_1$-$C_{22}$ Carboxylic Acid | 50-99 | 70-95 | 75-90 |
| Hydrogen Peroxide | 0.1-50 | 1-50 | 1-10 |
| Additional Functional Ingredients | 0-25 | 0.01-10 | 0.5-10 |

Additional Functional Ingredients

In an aspect of the invention, the corrosion inhibitor compositions and the biocides (oxidizing and/or non-oxidizing) employed for corrosion inhibitors may further include a variety of additional functional components. In some embodiments, the corrosion inhibitor compositions and the biocides (oxidizing and/or non-oxidizing) make up a large amount, or even substantially all of the total weight of the compositions. For example, in some embodiments few or no additional functional ingredients are disposed therein. In an embodiment, no additional functional ingredients are employed.

In other embodiments, additional functional ingredients may be included in the compositions, including any of the corrosion inhibitor compositions and the biocides (oxidizing and/or non-oxidizing). The functional ingredients provide desired properties and functionalities to the compositions. For the purpose of this application, the term "functional ingredient" includes a material that when dispersed or dissolved in a use and/or concentrate solution, such as an aqueous solution, provides a beneficial property in a particular use. Some particular examples of functional materials are discussed in more detail below, although the particular materials discussed are given by way of example only, and that a broad variety of other functional ingredients may be used.

In embodiments employing an additional functional ingredient, the compositions may include for example, a catalyst (e.g. enzyme), stabilizing agents, pH buffering agents, acidulant, friction reducers, viscosity enhancers, defoaming agents, anti-redeposition agents, additional biocides, bleaching agents, solubility modifiers, dispersants, rinse aids, metal protecting agents, additional corrosion inhibitors, emulsion breakers, emulsion stabilizers, scale inhibitors, including conventional scale inhibitors and/or iron dissolvers, sequestrants and/or chelating agents, peracid stabilizers, acids, surfactants and/or antimicrobial agents, additional carboxylic acids, fragrances and/or dyes, rheology modifiers or thickeners, hydrotropes or couplers, buffers, solvents and the like. In an aspect, an additional functional ingredient may further include a synergist in the form of a strongly reducing compound in nature to enhance performance, such as for example mercaptoethanol and/or TGA.

Friction Reducers

In an aspect, the corrosion inhibitor compositions, the peroxycarboxylic acid compositions and/or peroxycarboxylic acid forming compositions can further comprise friction reducers. Friction reducers are used in water or other water-based fluids used in hydraulic fracturing treatments for subterranean well formations in order to improve permeability of the desired gas and/or oil being recovered from the fluid-conductive cracks or pathways created through the fracking process. The friction reducers allow the water to be pumped into the formations more quickly. Various polymer additives have been widely used as friction reducers to enhance or modify the characteristics of the aqueous fluids used in well drilling, recovery and production applications.

Examples of commonly used friction reducers include polyacrylamide polymers and copolymers. In an aspect, additional suitable friction reducers may include acrylamide-derived polymers and copolymers, such as polyacrylamide (sometime abbreviated as PAM), acrylamide-acrylate (acrylic acid) copolymers, acrylic acid-methacrylamide copolymers, partially hydrolyzed polyacrylamide copolymers (PHPA), partially hydrolyzed polymethacrylamide, acrylamide-methyl-propane sulfonate copolymers (AMPS) and the like. Various derivatives of such polymers and copolymers, e.g., quaternary amine salts, hydrolyzed versions, and the like, should be understood to be included with the polymers and copolymers described herein.

Friction reducers are combined with water and/or other aqueous fluids, which in combination are often referred to as "slick water" fluids. Slick water fluids have reduced frictional drag and beneficial flow characteristics which enable the pumping of the aqueous fluids into various gas- and/or oil-producing areas, including for example for fracturing.

In an aspect of the invention, a friction reducer is present in a use solution in an amount between about 100 ppm to 1,000 ppm. In a further aspect, a friction reducer is present in a use solution in an amount of at least about 0.01 wt-% to about 10 wt-%, preferably at least about 0.01 wt-% to about 5 wt-%, preferably at least about 0.01 wt-% to about 1 wt-%, more preferably at least about 0.01 wt-% to about 0.5 wt-%, and still more preferably at least about 0.01 wt-% to about 0.1 wt-%. Beneficially, the compositions and methods of the invention do not negatively interfere with friction reducers included in an aqueous solution.

Viscosity Enhancers

In an aspect, the corrosion inhibitor compositions and the biocides (oxidizing and/or non-oxidizing) further comprise viscosity enhancers. Viscosity enhancers are additional polymers used in water or other water-based fluids used in hydraulic fracturing treatments to provide viscosity enhancement. Natural and/or synthetic viscosity-increasing polymers may be employed in compositions and methods according to the invention. Viscosity enhancers may also be referred to as gelling agents and examples include guar, xanthan, cellulose derivatives and polyacrylamide and polyacrylate polymers and copolymers, and the like.

In an aspect of the invention, a viscosity enhancer is present in a use solution in an amount between about 100 ppm to 1,000 ppm. In a further aspect, a viscosity enhancer is present in a use solution in an amount of at least about 0.01 wt-% to about 10 wt-%, preferably at least about 0.01 wt-% to about 5 wt-%, preferably at least about 0.01 wt-% to about 1 wt-%, at least about 0.01 wt-% to about 2 wt-%, preferably at least about 0.01 wt-% to about 1 wt-%, preferably at least about 0.01 wt-% to about 0.5 wt-%. Beneficially, the compositions and methods of the invention do not negatively interfere with viscosity enhancer included in an aqueous solution.

Additional Corrosion Inhibitors

In an aspect, the corrosion inhibitor compositions and the biocides (oxidizing and/or non-oxidizing) further comprise additional conventional corrosion inhibitors. Corrosion inhibitors are additional molecules used in oil and gas recovery operations.

Corrosion inhibitors that may be employed in the present disclosure further include the exemplary corrosion inhibitors disclosed in U.S. Pat. No. 5,965,785, U.S. Patent Publication No. 2010/0108566, GB Pat. No. 1,198,734, WO/03/006581, WO04/044266, and WO08/005058, each incorporated herein by reference in their entireties. In an embodiment, the corrosion inhibitors include cationic surfactant comprising an ammonium halide. The ammonium halide may include any suitable types of ammonium halides. In embodiments, the ammonium halides include alkyl ammonium halides, polyalkyl ammonium halides, or any combinations thereof. In embodiments, the cationic surfactant includes any combination or at least one of an alkyl trimethyl ammonium halide, an alkyl dimethyl benzyl ammonium halide, and one or more imidazolinium halides.

In an aspect of the invention, an additional corrosion inhibitor is present in a use solution in an amount between about 1 ppm to 1,000 ppm. In a further aspect, a corrosion inhibitor is present in a use solution in an amount of at least about 0.0001 wt-% to about 10 wt-%, preferably at least about 0.0001 wt-% to about 5 wt-%, preferably at least about 0.0001 wt-% to about 1 wt-%, preferably at least about 0.0001 wt-% to about 0.1 wt-%, and still more preferably at least about 0.0001 wt-% to about 0.05 wt-%. Beneficially, the compositions and methods of the invention do not negatively interfere with corrosion inhibitor included in an aqueous solution.

Scale Inhibitors

In an aspect, the corrosion inhibitor compositions and the biocides (oxidizing and/or non-oxidizing) further comprise scale inhibitors. Scale inhibitors are additional molecules used in oil and gas recovery operations. Common scale inhibitors that may be employed in these types of applications include polymers and co-polymers, phosphates, phosphate esters and the like.

In an aspect of the invention, a scale inhibitor is present in a use solution in an amount between about 100 ppm to 1,000 ppm. In a further aspect, a scale inhibitor is present in a use solution in an amount of at least about 0.0001 wt-% to about 10 wt-%, at least about 0.0001 wt-% to about 1 wt-%, preferably at least about 0.0001 wt-% to about 0.1 wt-%, preferably at least about 0.0001 wt-% to about 0.05 wt-%. Beneficially, the compositions and methods of the invention do not negatively interfere with scale inhibitor included in an aqueous solution.

Additional Antimicrobial Agents

In an aspect, the corrosion inhibitor compositions and the biocides (oxidizing and/or non-oxidizing) further comprise additional microbial agents. Additional antimicrobial agents may be included in the compositions and/or methods of the invention for enhanced antimicrobial efficacy. In addition to the use of peracid compositions, additional antimicrobial agents and biocides may be employed. Additional biocides may include, for example, a quaternary ammonium compound as disclosed in U.S. Pat. No. 6,627,657, which is incorporated herein by reference in its entirety. In another embodiment, the additional biocide may include an oxidizer compatible phosphonium biocide, such as tributyl tetradecyl phosphonium chloride. The phosphonium biocide provides similar antimicrobial advantages as the quaternary ammonium compound in combination with the peracids. In addition, the phosphonium biocide is compatible with the anionic polymeric chemicals commonly used in the oil field applications, such as the methods of the fracking disclosed according to the invention.

Additional antimicrobial and biocide agents may be employed in amounts sufficient to provide antimicrobial efficacy, as may vary depending upon the water source in need of treatment and the contaminants therein. Such agents may be present in a use solution in an amount of at least about 0.1 wt-% to about 50 wt-%, preferably at least about 0.1 wt-% to about 20 wt-%, more preferably from about 0.1 wt-% to about 10 wt-%.

Acidulant

In an aspect, the corrosion inhibitor compositions and the biocides (oxidizing and/or non-oxidizing) further comprise an acidulant. In an aspect, the acidulant is included in the second reagent with hydrogen peroxide. Any suitable acid can be included in the compositions as an acidulant. In an embodiment the acidulant is an acid or an aqueous acidic solution. In an embodiment, the acidulant includes an inorganic acid. In some embodiments, the acidulant is a strong mineral acid. Suitable inorganic acids include, but are not limited to, sulfuric acid, sodium bisulfate, phosphoric acid, nitric acid, hydrochloric acid. In some embodiments, the acidulant includes an organic acid. Suitable organic acids include, but are not limited to, methane sulfonic acid, ethane sulfonic acid, propane sulfonic acid, butane sulfonic acid, xylene sulfonic acid, cumene sulfonic acid, benzene sulfonic acid, formic acid, acetic acid, mono, di, or tri-halocarboxylic acids, picolinic acid, dipicolinic acid, and mixtures thereof.

In an aspect, a strong mineral acid such as nitric acid or sulfuric acid can be used to treat water sources, as disclosed in U.S. Pat. No. 4,587,264, which is incorporated herein by reference in its entirety. The combined use of a strong mineral acid with the peracid composition provides enhanced antimicrobial efficacy as a result of the acidity assisting in removing chemical contaminants within the water source (e.g. sulfite and sulfide species). In addition, some strong mineral acids, such as nitric acid, provide a further benefit of reducing the risk of corrosion toward metals contacted by the peracid compositions according to the invention. In some embodiments, the present composition does not comprise a mineral acid or a strong mineral acid.

In certain embodiments, the acidulant is present in amounts from about 0.001 to about 50 wt-% acidulant, about 0.001 to about 10 wt-%, about 0.01 to about 1 wt-% acidulant, or about 0.05 to about 0.5 wt-%.

Catalyst

In an aspect, the corrosion inhibitor composition and the biocides (oxidizing and/or non-oxidizing) further comprise a catalyst or an enzyme, such as for catalyzing formation of the peroxycarboxylic acid from the ester of a polyhydric alcohol and carboxylic acid, and hydrogen peroxide. Any suitable catalyst or enzyme can be included in the peroxycarboxylic acid forming composition, e.g., a perhydrolytic enzyme, lipase, coronase, termanyl or esperease. The catalyst or an enzyme can be comprised in any suitable part of the peroxycarboxylic acid forming compositions. In some embodiments, the first reagent comprises the catalyst or enzyme. In other embodiments, the second reagent comprises the catalyst or enzyme. In still other embodiments, the peroxycarboxylic acid forming compositions can further comprise a third reagent that comprises the catalyst or enzyme. In yet other embodiments, the solid composition comprises the catalyst or enzyme. In certain embodiments, the catalyst is present in amounts from about 0.0001 to about 50 wt-%, about 0.001 to about 25 wt-%, about 0.01 to about 10 wt-%, or about 0.01 to about 1 wt-%.

Buffering Agents

In an aspect, the corrosion inhibitor compositions and the biocides (oxidizing and/or non-oxidizing) further comprise a buffering agent. The present compositions can comprise any suitable pH buffering agent. The pH buffer reagent can include any reagent that is compatible with the ester(s) in the peroxycarboxylic acid forming compositions. Exemplary buffer agents suitable for using with a liquid ester can be an organic amine, such as triethanol amine, imidazole, etc. Exemplary buffer agents suitable for using with a solid form of ester include a broader range of buffers, such as a carbonate salt, a phosphate salt, etc. The pH buffer reagent can be comprised in any suitable part of the present peroxyformic acid forming compositions. In some embodiments, the first reagent comprises a pH buffering agent. In other embodiments, the peroxycarboxylic acid forming compositions can further comprise a third reagent that comprises a pH buffering agent. In still other embodiments, the solid composition comprises a pH buffering agent. In certain embodiments, the buffering agent is present in amounts from about 0.001 to about 25 wt-%, about 0.001 to about 15 wt-%, about 0.001 to about 10 wt-%, or about 0.01 to about 1 wt-%.

Alkalinity Source

In an aspect, the corrosion inhibitor compositions and biocide composition (oxidizing and/or non-oxidizing) further comprise an alkalinity source. The relationship between corrosion control and operating pH is straight forward: acidic pH conditions are more corrosive than alkaline conditions. The source of alkalinity can include, but is not limited to, an alkaline metal hydroxide, an alkaline earth metal hydroxide, an alkali metal silicate, an alkali metal carbonate, borates and mixtures thereof. Suitable alkaline metal hydroxides include, but are not limited to, sodium hydroxide, potassium hydroxide and mixtures thereof. Suitable alkaline earth metal hydroxides include, but are not limited to, magnesium hydroxide, calcium hydroxide and mixtures and derivatives thereof. Suitable alkali metal silicates include but are not limited to, sodium silicate and derivatives thereof. In other embodiments, an alkali metal carbonate can be used as a source of alkalinity. In a preferred aspect an alkaline metal hydroxide is employed. The source of alkalinity can be added to the self-indicating chemistry compositions to provide the desired pH. In some embodiments, the alkalinity source is added to achieve a pH of about 7 or greater. In certain embodiments, the alkalinity agent is present in amounts from about 0.001 to about 50 wt-%, about 0.001 to about 10 wt-%, or about 0.01 to about 1 wt-%.

Corrosion Inhibited Compositions

In some embodiments, the biocide and corrosion inhibitor are combined to form a corrosion inhibited aqueous composition. In an aspect, the aqueous composition comprises from about 0.5 ppm to about 50,000 ppm of an oxidizing or non-oxidizing biocide and from about 1 ppm to about 10,000 ppm of the corrosion inhibitor.

In an aspect, the corrosion inhibited aqueous composition comprises any suitable level of the oxidizing or a non-oxidizing biocide, including from about 0.5 ppm to about 50,000 ppm, from about 1 ppm to about 10,000 ppm, or from about 100 ppm to about 1,000 ppm of said oxidizing or a non-oxidizing biocide, such as for example a peroxycarboxylic acid, any suitable level of the corrosion inhibitor, including from about 1 ppm to about 10,000 ppm, from about 1 ppm to about 1,000 ppm, from about 1 ppm to about 500 ppm, or from about 100 ppm to about 200 ppm.

In an aspect, the corrosion inhibited aqueous composition comprises any suitable level of the corrosion inhibitor, including from about 1 ppm to about 10,000, 1 to about 10 ppm, 10 to about 20 ppm, 20 to about 30 ppm, 30 to about 40 ppm, 40 to about 50 ppm, 50 to about 60 ppm, 60 to about 70 ppm, 70 to about 80 ppm, 80 to about 90 ppm, 90 to about 100 ppm, 100 to about 110 ppm, 110 to about 120 ppm, 120 to about 130 ppm, 130 to about 140 ppm, 140 to about 150 ppm, 100 to about 150 ppm, 150 to about 200 ppm, 200 to about 250 ppm, 250 to about 300 ppm, 300 to about 350 ppm, 350 to about 400 ppm, 400 to about 450 ppm, 450 to about 500 ppm, 500 to about 550 ppm, 550 to about 600 ppm, 600 to about 650 ppm, 650 to about 700 ppm, 700 to about 750 ppm, 750 to about 800 ppm, 800 to about 850 ppm, 850 to about 900 ppm, 900 to about 950 ppm, 950 to about 1,000 ppm, 1,000 to about 1,500 ppm, 1,500 to about 2,000 ppm, 2,000 to about 2,500 ppm, 2,500 to about 3,000 ppm, 3,000 to about 3,500 ppm, 3,500 to about 4,000 ppm, 4,000 to about 4,500 ppm, 4,500 to about 5,000 ppm, 5,000 to about 5,500 ppm, 5,500 to about 6,000 ppm, 6,000 to about 6,500 ppm, 6,500 to about 7,000 ppm, 7,000 to about 7,500 ppm, 7,500 to about 8,000 ppm, 8,000 to about 8,500 ppm, 8,500 to about 9,000 ppm, or 9,000 to about 10,000 ppm of the corrosion inhibitor.

In an aspect, the aqueous composition comprises from about 0.5 ppm to about 50,000 ppm of a peroxyformic acid and from about 1 ppm to about 10,000 ppm of the corrosion inhibitor. In an aspect, the corrosion inhibited aqueous composition comprises any suitable level of the peroxyformic acid, including from about 0.5 ppm to about 50,000 ppm, from about 1 ppm to about 10,000 ppm, or from about 100 ppm to about 1,000 ppm. In an aspect, the corrosion inhibited aqueous composition comprises any suitable level of the corrosion inhibitor, including from about 1 ppm to about 10,000, 1 to about 10 ppm, 10 to about 20 ppm, 20 to about 30 ppm, 30 to about 40 ppm, 40 to about 50 ppm, 50 to about 60 ppm, 60 to about 70 ppm, 70-80 ppm, 80 to about 90 ppm, 90 to about 100 ppm, 100 to about 110 ppm, 110 to about 120 ppm, 120 to about 130 ppm, 130 to about 140 ppm, 140 to about 150 ppm, 100 to about 150 ppm, 150 to about 200 ppm, 200 to about 250 ppm, 250 to about 300 ppm, 300 to about 350 ppm, 350 to about 400 ppm, 400 to about 450 ppm, 450 to about 500 ppm, 500 to about 550 ppm, 550 to about 600 ppm, 600 to about 650 ppm, 650 to about 700 ppm, 700 to about 750 ppm, 750 to about 800 ppm, 800 to about 850 ppm, 850 to about 900 ppm, 900 to about 950 ppm, 950 to about 1,000 ppm, 1,000 to about 1,500 ppm, 1,500 to about 2,000 ppm, 2,000 to about 2,500 ppm, 2,500 to about 3,000 ppm, 3,000 to about 3,500 ppm, 3,500 to about 4,000 ppm, 4,000 to about 4,500 ppm, 4,500 to about 5,000 ppm, 5,000 to about 5,500 ppm, 5,500 to about 6,000 ppm, 6,000 to about 6,500 ppm, 6,500 to about 7,000 ppm, 7,000 to about 7,500 ppm, 7,500 to about 8,000 ppm, 8,000 to about 8,500 ppm, 8,500 to about 9,000 ppm, or 9,000 to about 10,000 ppm of the corrosion inhibitor.

In an aspect, the corrosion inhibited aqueous composition has a pH range of from 1 to about 12.0, preferably at a pH less than 12, preferably at a pH less than 11, preferably at a pH less than 10, less than 9, or less than 8.2 (pKa of peroxyacetic acid). Beneficially the compositions can be at acidic pH, neutral, and alkaline pHs.

Beneficially the corrosion inhibitor compositions provides a treated system with a corrosion rate of less than about 4 mils per year (MPY), from about 0 to about 4 MPT, from 0 to about 3, from 0 to about 2, or from 0 to about 1. In an aspect, the corrosion inhibited composition concentration is adjusted in a treated water source (or other target) to provide a corrosion rate of less than about 4 mils per year (MPY).

Corrosion Inhibited Peroxyformic Acid Forming Compositions

In some embodiments, an oxidizing peracid comprising peroxyformic acid can be formulated into a stable premix composition for use according to the invention. This unexpected benefit of providing a corrosion inhibitor into an oxidizing source, such as a carboxylic acid or peroxycarboxylic acid, overcomes substantial limitations of the art which are known to have negative impact on stability and performance when the oxidizing source is combined in a corrosion inhibitor.

In an embodiment, a peroxyformic acid corrosion inhibited composition comprises at least a two part system, comprising a first premix comprising formic acid and the corrosion inhibitor, and a second part comprising a source of hydrogen peroxide, wherein the two part composition is combined to generate the peroxyformic acid in situ.

Beneficially, the premix comprising the performic acid and the corrosion inhibitor is shelf-stable for a period of at least 1 month, at least 2 months, at least 3 months, at least 4 months, at least 5 months, at least 6 months, at least 7 months, at least 8 months, at least 9 months, at least 10 months, at least 11 months, at least 12 months, or greater.

According to embodiments of the invention the premix composition comprising formic acid and the corrosion inhibitor can include any suitable amount or ratio of the components. In an aspect, the premix composition comprises from about 1 to about 99 wt-% formic acid and from about 1 to about 99 wt-% corrosion inhibitor, from about 10 to about 90 wt-% formic acid and from about 10 to about 90 wt-% corrosion inhibitor, from about 20 to about 80 wt-% formic acid and from about 20 to about 80 wt-% corrosion inhibitor, or any amounts or ratios there between.

According to embodiments of the invention the premix and/or the second part to the system can further comprise additional functional ingredients as disclosed herein. Exemplary, additional functional ingredients include for example, catalyst, stabilizing agent, pH buffering agent, acidulant, friction reducer, viscosity enhancer, defoaming agent, anti-redeposition agent, bleaching agent, solubility modifier, dispersant, metal protecting agent, additional corrosion inhibitor, additional biocide, scale inhibitor, sequestrant and/or chelating agent, peracid stabilizer, surfactant and/or antimicrobial agent, additional carboxylic acid, emulsion breaker, emulsion stabilizer, fragrance and/or dye, rheology modifier or thickener, hydrotrope or coupler, buffer, solvent and/or combinations thereof.

Beneficially the corrosion inhibitor compositions provides a treated system with a corrosion rate of less than about 4 mils per year (MPY), from about 0 to about 4 MPT, from 0 to about 3, from 0 to about 2, or from 0 to about 1. In an aspect, the corrosion inhibited composition concentration is adjusted in a treated water source (or other target) to provide a corrosion rate of less than about 4 mils per year (MPY).

Corrosion Inhibited Non-Oxidizing Biocide Compositions

In some embodiments, a non-oxidizing biocide and a corrosion inhibitor can be formulated into a stable composition for use according to the invention providing an unexpected benefit according to the invention. In an embodiment, a non-oxidizing biocide corrosion inhibited composition comprises the biocide and the corrosion inhibitor. In such embodiments, the composition is shelf-stable for a period of at least 1 month, at least 2 months, at least 3 months, at least 4 months, at least 5 months, at least 6 months, at least 7 months, at least 8 months, at least 9 months, at least 10 months, at least 11 months, at least 12 months, or greater.

According to embodiments of the invention the composition comprising non-oxidizing biocide and the corrosion inhibitor can include any suitable amount or ratio of the components. In an aspect, the premix composition comprises from about 1 to about 99 wt-% non-oxidizing biocide and from about 1 to about 99 wt-% corrosion inhibitor, from about 10 to about 90 wt-% non-oxidizing biocide and from about 10 to about 90 wt-% corrosion inhibitor, from about 20 to about 80 wt-% non-oxidizing biocide and from about 20 to about 80 wt-% corrosion inhibitor, or any amounts or ratios there between.

According to embodiments of the invention the composition can further comprise additional functional ingredients as disclosed herein. Exemplary, additional functional ingredients include for example, catalyst, stabilizing agent, pH buffering agent, acidulant, friction reducer, viscosity enhancer, defoaming agent, anti-redeposition agent, bleaching agent, solubility modifier, dispersant, metal protecting agent, additional corrosion inhibitor, additional biocide, scale inhibitor, sequestrant and/or chelating agent, peracid stabilizer, surfactant and/or antimicrobial agent, additional carboxylic acid, emulsion breaker, emulsion stabilizer, fragrance and/or dye, rheology modifier or thickener, hydrotrope or coupler, buffer, solvent and/or combinations thereof.

Beneficially the corrosion inhibitor compositions provides a treated system with a corrosion rate of less than about 4 mils per year (MPY), from about 0 to about 4 MPT, from 0 to about 3, from 0 to about 2, or from 0 to about 1. In an aspect, the corrosion inhibited composition concentration is adjusted in a treated water source (or other target) to provide a corrosion rate of less than about 4 mils per year (MPY).

Methods of Inhibiting and Preventing Corrosion

In an embodiment, the present invention is directed to a method for preventing or treating corrosion on a target, which method comprises contacting a target with an effective amount of a corrosion protected biocide, including oxidizing or a non-oxidizing biocide, such as a peroxycarboxylic acid composition (or peroxycarboxylic acid forming composition or other biocide), to reduce or eliminate corrosion caused by the biocide. It is understood that reference to the peroxycarboxylic acid compositions shall further be understood to refer to and include as an additional suitable embodiment the peroxycarboxylic acid forming compositions. It is further understood that other non-oxidizing biocides are suitable for use in corrosion inhibition according to the methods of the invention.

In an aspect, the corrosion inhibitor compositions provides a treated system with a corrosion rate of less than about 4 mils per year (MPY), from about 0 to about 4 MPY, from 0 to about 3, from 0 to about 2, or from 0 to about 1. In an aspect, the corrosion inhibitor composition concentration is adjusted in a treated water source (or other target) to provide a corrosion rate of less than about 4 mils per year (MPY).

In an aspect, the methods for treating a target according to the invention are suitable for preventing general and/or biocide corrosion. The methods of the invention provide improved corrosion prevention in comparison to an untreated target (e.g. water source without any corrosion inhibitor) and/or in comparison to a conventional corrosion inhibitors. Conventional corrosion inhibitors include, for example, cationic surfactant comprising an ammonium halide, such as alkyl ammonium halides, polyalkyl ammonium halides, or any combinations thereof. In embodiments, the cationic surfactant includes any combination or at least one of an alkyl trimethyl ammonium halide, an alkyl dimethyl benzyl ammonium halide, and one or more imidazolinium halides.

The corrosion inhibitor composition reduces the amount of general or biocide to about induced corrosion by more than 1%, 2%, 3%, 4%, 5%, 6%, 7%, 8%, 9%, or 10% than if the composition were not added to the aqueous system (also referred to as an untreated composition or system). In an aspect, the corrosion rate of a system is lower by at least 1 to about 2% upon addition of the corrosion inhibitor composition. Beneficially within a period of up to 24 hours the corrosion rate of a system is lower by at least 1%, 2%, 3%, 4%, 5%, 6%, 7%, 8%, 9%, or 10%. The corrosion inhibitor composition reduces the amount of general or biocide-induced corrosion by more than 10%, more than 15%, more than 20%, more than 25%, or still more preferably more than 50%, than if the corrosion inhibitor composition were not added to the aqueous system.

The corrosion inhibitor composition reduces the amount of general or biocide-induced corrosion by more than 1%, 2%, 3%, 4%, 5%, 6%, 7%, 8%, 9%, or 10% than if the composition were treated with a conventional corrosion inhibitor. In an aspect, the corrosion rate of a system is lower by at least 1 to about 2% upon addition of the corrosion inhibitor composition. Beneficially within a period of up to 24 hours the corrosion rate of a system is lower by at least 1%, 2%, 3%, 4%, 5%, 6%, 7%, 8%, 9%, or 10%. The corrosion inhibitor composition reduces the amount of general or biocide-induced corrosion by more than 10%, more than 15%, more than 20%, more than 25%, or still more preferably more than 50%, than if a conventional corrosion inhibitor composition were added to the aqueous system.

The corrosion inhibitor composition may be used in conjunction with various additional functional ingredients. In some embodiments, the corrosion inhibitor composition may be used in conjunction with other production chemicals including, but not limited to, hydrate inhibitors, scale inhibitors, asphaltene inhibitors, paraffin inhibitors, $H_2S$ scavengers, $O_2$ scavengers, emulsion breakers, foamers and defoamers, and water clarifiers.

Targets for Corrosion Inhibition

The presently disclosed corrosion inhibitor compositions, methods of inhibiting or reducing corrosion, and corrosion control programs can be applied to any type of industrial system, such as water recirculating systems, cooling water systems, boiler water systems, pulp slurries, papermaking processes, ceramic slurries, mixed solid/liquid systems, and oil-field applications, such as those disclosed in the background section of the present application. In general, the presently disclosed corrosion inhibitors can effectively inhibit or reduce corrosion in any type of aqueous system comprising a metallic or glass surface.

In an aspect, the methods for treating a target comprise contacting the target with a oxidizing or a non-oxidizing biocide and a corrosion inhibitor according to the invention. In a preferred embodiment, the present methods can be used to treat a target that is contained within a water source, and the present methods can comprise providing an effective amount of oxidizing or a non-oxidizing biocide, such as for example a peroxycarboxylic acid composition, to a water source to prevent corrosion on surfaces in contact with the water source, such as metallic surfaces. In one aspect, the metallic surface comprises mild steel but in other aspects, the metallic surface may comprise a member selected from the group consisting of mild steel, galvanized steel, aluminum, aluminum alloys, copper, copper nickel alloys, copper zinc alloys, brass, chrome steels, ferritic alloy steels, austenitic stainless steels, precipitation-hardened stainless steels, high nickel content steels, and any combination thereof.

The aqueous medium in which the corrosion inhibitor and oxidizing or a non-oxidizing biocide are applied to may be in contact with many different types of surfaces that are capable of corrosion. Illustrative, non-limiting examples are those surfaces in an oil and gas pipeline and/or refinery, such as separation vessels, dehydration units, gas lines, and pipelines, in addition to cooling water systems. In general, the dosage may be dependent upon the corrosivity of the system and oftentimes the water cut realized in the application.

In a preferred embodiment, the target is an aqueous medium in which the corrosion inhibitor and oxidizing or a non-oxidizing biocide are applied to may be in contact with many different types of surfaces that are capable of corrosion. Illustrative, non-limiting examples are those surfaces in an oil and gas pipeline and/or refinery, such as separation vessels, dehydration units, gas lines, and pipelines, in addition to cooling water systems. In general, the dosage may be dependent upon the corrosivity of the system and oftentimes the water cut realized in the application.

In some aspects, the corrosion inhibitor and oxidizing or a non-oxidizing biocide may be injected down the annulus of a well and flushed with the appropriate solvent. In other aspects, it may be injected through suitable injection lines to areas where corrosion can occur through capillaries or umbilical lines (in many cases at the wellhead if suitable metallurgy is used downhole).

The present methods can be used to treat any suitable water source, including both buffered and non-buffered water systems. For example, a water source in need of treatment can be a source water (e.g. fresh water, pond water, lake water, municipal water, etc.), reuse water, sea or brine water, brackish water, recycled water, produced water, paper manufacturing water, tower water, such as cooling water, or a combination thereof of any such water sources. Suitable water sources include those used in oil and/or gas drilling operations, such as a water source used in an operation of induced hydraulic fracturing (hydrofracturing or fracking), which may further include water sources comprising a friction reducer or a viscosity enhancer. Such treated waters according to the invention can be used for both slick water fracturing (i.e. using frictions reducers) and/or gel fracturing (i.e. using viscosity enhancers), depending on the type of formation being fractured and the type of hydrocarbon expected to be produced.

In an aspect, where the water is a water source employed in well fluid operations. In such an aspect of the invention, recycled water sources (e.g. produced waters) are often employed to reduce the amount of a freshwater, pond water or seawater source required. Recycled or produced water are understood to include non-potable water sources. The use of such produced waters (in combination with freshwater, pond water or seawater) reduces certain economic and/or environmental constraints. In an aspect of the invention, thousands to millions of gallons of water may be employed and the combination of produced water with fresh water sources provides significant economic and environmental advantages. In an aspect of the invention, as much produced water as practical is employed. In an embodiment at least 1% produced water is employed, preferably at least 5% produced water is employed, preferably at least 10% produced water is employed, preferably at least 20% produced water is employed, or more preferably more than 20% produced water is employed. In some embodiments up to or about 100% of produced water is employed.

In yet other aspects, the methods for treating a target can include or be used on or in other industrial equipment and in other industrial process streams such as heaters, cooling towers, boilers, retort waters, rinse waters, aseptic packaging wash waters, and the like. The present methods may be used to inhibit and/or remove corrosion in recreational waters such as in pools, spas, recreational flumes and water slides, fountains, and the like.

In alternative aspects, the methods for treating a target can include a target that is water and/or at least a portion of a medium, a container, an equipment, a system or a facility for producing, holding, processing, packaging, storing, or transporting pulp. The present methods can be used to treat water and/or other target(s) to prevent corrosion. For example, the present methods can be used in papermaking, textiles, food, or pharmaceutical industry. In such embodiments, the methods can be used to treat a water source, alone or in combination with other target(s), to form a treated water source that comprises any suitable level of the corrosion inhibitor and oxidizing or a non-oxidizing biocide.

In alternative aspects, the methods for treating a target can include a target that is water and/or at least a portion of a medium, a surface, a container, an equipment, or a system in a health care facility, e.g., a physical office or a hospital. The present methods can be used to treat water and/or other target(s) to prevent corrosion. In such embodiments, the methods can be used to treat a water source, alone or in combination with other target(s), to form a treated water source that comprises any suitable level of corrosion inhibitor and oxidizing or a non-oxidizing biocide to prevent corrosion.

In alternative aspects, the methods for treating a target can include a target that is water and/or at least a portion of a container, an equipment, a system or a facility for holding, processing, packaging, storing, transporting, preparing, cooking or serving the food item or the plant item. The present methods can be used to treat water and/or other target(s) to prevent corrosion. In such embodiments, the methods can be used to treat a water source, alone or in combination with other target(s), to form a treated water source that comprises any suitable level of corrosion inhibitor and oxidizing or a non-oxidizing biocide to prevent corrosion.

In some embodiments, the target is at least a portion of a container, an equipment, a system or a facility for holding, processing, packaging, storing, transporting, preparing, cooking or serving a meat item, a fruit item, a vegetable item, or a grain item. In other embodiments, the target is at least a portion of a container, an equipment, a system or a facility for holding, processing, packaging, storing, or transporting an animal carcass. In still other embodiments, the target is at least a portion of a container, an equipment, a system or a facility used in food processing, food service or health care industry. In yet other embodiments, the target is at least a portion of a fixed in-place process facility. An exemplary fixed in-place process facility can comprise a milk line dairy, a continuous brewing system, a pumpable food system or a beverage processing line.

In particular aspects of the present disclosure, the corrosion inhibitors may be used in connection with warewashing compositions. Warewashing compositions may be used for protecting articles, such as glassware or silverware, from corrosion in a dishwashing or warewashing machine. However, it is to be understood that the warewashing compositions comprising the presently disclosed corrosion inhibitors can be available for cleaning environments other than inside a dishwashing or warewashing machine. In addition to the corrosion inhibitor, the warewashing composition and/or use solution may also include cleaning agents, alkaline sources, surfactants, chelating/sequestering agents, bleaching agents, detergent builders or fillers, hardening agents or solubility modifiers, defoamers, anti-redeposition agents, threshold agents, aesthetic enhancing agents (i.e., dye, perfume), and the like. Adjuvants and other additive ingredients will vary according to the type of composition being manufactured. It should be understood that these additives are optional and need not be included in the cleaning composition. When they are included, they can be included in an amount that provides for the effectiveness of the particular type of component.

Contacting the Targets for Inhibiting Corrosion

In an aspect, the contacting of the target with the corrosion inhibitor and oxidizing or a non-oxidizing biocide forms a treated target composition, wherein said treated target composition comprises any suitable level of the oxidizing or a non-oxidizing biocide, including from about 0.5 ppm to about 50,000 ppm, from about 1 ppm to about 10,000 ppm, or from about 100 ppm to about 1,000 ppm of said oxidizing or a non-oxidizing biocide, such as for example a peroxycarboxylic acid, any suitable level of the corrosion inhibitor, including from about 1 ppm to about 10,000 ppm, from about 1 ppm to about 1,000 ppm, from about 1 ppm to about 500 ppm, or from about 100 ppm to about 200 ppm, and preferably, said contacting lasts for sufficient time to prevent corrosion. As one skilled in the art will ascertain, the concentration of the corrosion inhibitor and the oxidizing or a non-oxidizing biocide for contacting the target will vary based upon factors including, for example, the particular application.

The target can be contacted with the corrosion inhibitor (either alone, in sequence with or parallel with the addition of the oxidizing or a non-oxidizing biocide) or in a combined composition with the oxidizing or a non-oxidizing biocide to form a treated target composition comprising any suitable level of said corrosion inhibitor, e.g., about 1 ppm to about 10,000, about 1 to about 10 ppm, about 10 to about 20 ppm, about 20 to about 30 ppm, about 30 to about 40 ppm, about 40 to about 50 ppm, about 50 to about 60 ppm, about 60 to about 70 ppm, about 70 to about 80 ppm, about 80 to about 90 ppm, about 90 to about 100 ppm, about 100 to about 150 ppm, about 150 to about 200 ppm, about 200 to about 250 ppm, about 250 to about 300 ppm, about 300 to about 350 ppm, about 350 to about 400 ppm, about 400 to about 450 ppm, about 450 to about 500 ppm, about 500 to about 550 ppm, about 550 to about 600 ppm, about 600 to about 650 ppm, about 650 to about 700 ppm, about 700 to about 750 ppm, about 750 to about 800 ppm, about 800 to about 850 ppm, about 850 to about 900 ppm, about 900 to about 950 ppm, about 950 to about 1,000 ppm, about 1,000 to about 1,500 ppm, about 1,500 to about 2,000 ppm, about 2,000 to about 2,500 ppm, about 2,500 to about 3,000 ppm, about 3,000 to about 3,500 ppm, about 3,500 to about 4,000 ppm, about 4,000 to about 4,500 ppm, or about 4,500 to about 5,000 ppm, about 5,000 to about 5,500 ppm, about 5,500 to about 6,000 ppm, about 6,000 to about 6,500 ppm, about 6,500 to about 7,000 ppm, about 7,000 to about 7,500 ppm, about 7,500 to about 8,000, about 8,000 to about 8,500 ppm, about 8,500 to about 9,000 ppm, about 9,000 to about 9,500 ppm, or about 9,500 to about 10,000 ppm of the corrosion inhibitor.

In an embodiment, the target can be contacted with the corrosion inhibitor on an ongoing or continuous dosing basis, wherein the oxidizing or a non-oxidizing biocide is dosed at a less frequent basis (either alone, in sequence with or parallel with the addition of the) to form a treated target composition comprising any suitable level of said corrosion inhibitor, e.g., about 1 ppm to about 10,000, about 1 to about 10 ppm, about 10 to about 20 ppm, about 20 to about 30 ppm, about 30 to about 40 ppm, about 40 to about 50 ppm, about 50 to about 60 ppm, about 60 to about 70 ppm, about 70 to about 80 ppm, about 80 to about 90 ppm, about 90 to about 100 ppm, about 100 to about 150 ppm, about 150 to about 200 ppm, about 200 to about 250 ppm, about 250 to about 300 ppm, about 300 to about 350 ppm, about 350 to about 400 ppm, about 400 to about 450 ppm, about 450 to about 500 ppm, about 500 to about 550 ppm, about 550 to about 600 ppm, about 600 to about 650 ppm, about 650 to about 700 ppm, about 700 to about 750 ppm, about 750 to about 800 ppm, about 800 to about 850 ppm, about 850 to about 900 ppm, about 900 to about 950 ppm, about 950 to about 1,000 ppm, about 1,000 to about 1,500 ppm, about 1,500 to about 2,000 ppm, about 2,000 to about 2,500 ppm, about 2,500 to about 3,000 ppm, about 3,000 to about 3,500 ppm, about 3,500 to about 4,000 ppm, about 4,000 to about 4,500 ppm, or about 4,500 to about 5,000 ppm, about 5,000 to about 5,500 ppm, about 5,500 to about 6,000 ppm, about 6,000 to about 6,500 ppm, about 6,500 to about 7,000 ppm, about 7,000 to about 7,500 ppm, about 7,500 to about 8,000, about 8,000 to about 8,500 ppm, about 8,500 to about 9,000 ppm, about 9,000 to about 9,500 ppm, or about 9,500 to about 10,000 ppm of the corrosion inhibitor.

The target can be contacted with the oxidizing or a non-oxidizing biocide, including for example a peroxycarboxylic acid, to form a treated target composition comprising any suitable level of said oxidizing or a non-oxidizing biocide, e.g., about 0.5 to about 10 ppm, about 10 to about 20 ppm, about 20 to about 30 ppm, about 30 to about 40 ppm, about 40 to about 50 ppm, about 50 to about 60 ppm, about 60 to about 70 ppm, about 70 to about 80 ppm, about 80 to about 90 ppm, about 90 to about 100 ppm, about 100 to about 150 ppm, about 150 to about 200 ppm, about 200 to about 250 ppm, about 250 to about 300 ppm, about 300 to about 350 ppm, about 350 to about 400 ppm, about 400 to about 450 ppm, about 450 to about 500 ppm, about 500 to about 550 ppm, about 550 to about 600 ppm, about 600 to about 650 ppm, about 650 to about 700 ppm, about 700 to about 750 ppm, about 750 to about 800 ppm, about 800 to about 850 ppm, about 850 to about 900 ppm, about 900 to about 950 ppm, about 950 to about 1,000 ppm, about 1,000 to about 1,500 ppm, about 1,500 to about 2,000 ppm, about 2,000 to about 2,500 ppm, about 2,500 to about 3,000 ppm, about 3,000 to about 3,500 ppm, about 3,500 to about 4,000 ppm, about 4,000 to about 4,500 ppm, or about 4,500 to about 5,000 ppm, about 5,000 to about 5,500 ppm, about 5,500 to about 6,000 ppm, about 6,000 to about 6,500 ppm, about 6,500 to about 7,000 ppm, about 7,000 to about 7,500 ppm, about 7,500 to about 8,000 ppm, about 8,000 to about 8,500 ppm, about 8,500 to about 9,000 ppm, about 9,000 to about 9,500 ppm, about 9,500 to about 10,000 ppm, about 10,000 to about 15,000 ppm, about 10,000 to about 20,000 ppm, about 20,000 to about 30,000 ppm, about 30,000 to about 40,000 ppm, about 40,000 to about 50,000 ppm of an oxidizing or a non-oxidizing biocide.

In some embodiments, the treated water source comprises from about 0.5 ppm to about 50,000 ppm of the oxidizing or a non-oxidizing biocide, e.g., about 0.5 to about 10 ppm, 10 to about 100 ppm, 10 to about 1,000 ppm, 100 to about 1,000 ppm, 200 to about 500 ppm, 500 to about 1,000 ppm, 500 to about 10,000 ppm, 1,000 to about 50,000 ppm oxidizing or a non-oxidizing biocide. In such embodiments, the treated water source further comprises from about 1 ppm to about 10,000 ppm of the corrosion inhibitor, e.g., about 1 to about 10 ppm, 10 to about 100 ppm, 10 to about 1,000 ppm, 100 to about 1,000 ppm, 100 to about 500 ppm, 200 to about 500 ppm, 500 to about 1,000 ppm, or 500 to about 10,000 ppm corrosion inhibitor.

The contacting step can last any suitable amount of time. In some embodiments, the contacting step can last for at least about 10 seconds. For example, the contacting step can last for at least about 10, 20, 30, 40, 50 seconds, 1 minute, 1 to about 2 minutes, 2 to about 3 minutes, 3 to about 4 minutes, 4 to about 5 minutes, 5 to about 6 minutes, 6 to about 7 minutes, 7 to about 8 minutes, 8 to about 9 minutes, or 9 to about 10 minutes, 10 to about 15 minutes, 15 to about 20 minutes, 20 to about 25 minutes, 25 to about 30 minutes, 30 to about 40 minutes, 40 to about 50 minutes, 50 to about 60 minutes, 1 to about 2 hours, 2 to about 3 hours, 3 to about 4 hours, 4 to about 5 hours, 5 to about 6 hours, 6 to about 7 hours, 7 to about 8 hours, 8 to about 9 hours, or 9 to about 10 hours, 16 hours, 1 day, 3 days, 1 week, or longer.

The contacting step can be conducted at suitable temperature range. For example, the contacting step can be conducted at a temperature ranging from about 0° C. to about 90° C., e.g., about 0° C. to about 1° C., 1° C. to about 2° C., 2° C. to about 3° C., 3° C. to about 4° C., 4° C. to about 5° C., 5° C. to about 10° C., 10° C. to about 15° C., 15° C. to about 20° C., 20° C. to about 25° C., 25° C. to about 30° C., 30° C. to about 35° C., 35° C. to about 40° C., 40° C. to about 45° C., 45° C. to about 50° C., 50° C. to about 55° C., 55° C. to about 60° C., 60° C. to about 65° C., or 65° C. to about 70° C., 70° C. to about 75° C., 75° C. to about 80° C., 80° C. to about 85° C., 85° C. to about 90° C. In other embodiments, the present methods can be conducted at a temperature at or lower than 0° C. In still other embodiments, the present methods can be conducted at ambient temperatures. In some embodiments, the present methods can be conducted at temperatures ranging from about 0° C. to about 130° C. in the course of the treatment operations such as oil and gas field operations, from between about 5° C. to about 100° C., more preferably between about 10° C. to about 80° C.

The contacting step can be conducted at suitable pH ranges. For example, the contacting step can be conducted at a pH range in the use solution or target system (e.g. water source or oxidizing or a non-oxidizing biocide containing source) of from 1 to about 12.0, preferably at a pH less than 12, preferably at a pH less than 11, preferably at a pH less than 10, less than 9, or less than 8.2 (pKa of peroxyacetic acid). Beneficially the methods of the invention provide corrosion inhibition at acidic pH, neutral, and alkaline pHs.

The contacting step can be conducted at suitable $CO_2$ and/or $O_2$ ranges. In an embodiment, the contacting step is conducted at a $CO_2$ range of 0 to about 15 psi. In an embodiment, the contacting step is conducted at a $O_2$ range at about 8.3 ppm.

The corrosion inhibitor and oxidizing or non-oxidizing biocide can be applied according to the methods of the invention in any suitable manner. The corrosion inhibitor and oxidizing or non-oxidizing biocide may be added at any location in the aqueous system. The addition of the corrosion inhibitor and/or oxidizing or non-oxidizing biocide may be manual or it may be automatic, for example, by using chemical injection pumps. In some aspects, the corrosion inhibitor and/or oxidizing or non-oxidizing biocide may be stored in a chemical storage tank and chemical injection pump associated therewith can pump the corrosion inhibitor and/or oxidizing or non-oxidizing biocide into the aqueous system. The chemical injection pump(s) can be automatically or manually controlled to inject any amount of the corrosion inhibitor and/or oxidizing or non-oxidizing biocide into the aqueous system.

In some embodiments, the corrosion inhibitor and oxidizing or non-oxidizing biocide (or as referred to herein as a corrosion inhibition composition) are applied or introduced into the target water in a continuous or intermittent manner and will depend on the type of water being treated. In some embodiments, the corrosion inhibitor and oxidizing or non-oxidizing biocide are introduced in a continuous manner to maintain a preferred ppm concentration of the corrosion inhibitor and oxidizing or non-oxidizing biocide. In some embodiments, the compositions are introduced into an aqueous fluid according to the methods disclosed in U.S. patent application Ser. No. 13/645,671, titled "New Method and Arrangement for Feeding Chemicals into a Hydrofracturing Process and Oil and Gas Applications", which is hereby incorporated by reference in its entirety. In additional embodiments, the compositions can be applied to a target by means of a spray, a fog, or a foam, or by dipping all or part of the target in the composition. In some embodiments, the composition is applied to the target by means of a spray, a fog, or a foam. In other embodiments, the diluted compositions are applied to the target by applying in the form of a thickened or gelled solution. In still other embodiments, all or part of the target is dipped in the composition. The target and/or the composition can be subject to any suitable movement to help or facilitate the contact between the target and the composition. In some embodiments, the composition can be agitated. In other embodiments, the composition can be sprayed onto a target under suitable pressure and at a suitable temperature.

In further embodiments, the methods of treating a target, such as a water source, can further comprise the step of contacting the target with additional functional ingredients, either formulated into the corrosion inhibitor inhibitor and/or oxidizing or non-oxidizing biocide (or a combined composition thereof) or added to the target in a separate contacting step at any suitable time, including before, simultaneously or after the corrosion inhibitor and oxidizing or non-oxidizing biocide. In some embodiments, the target can be contacted with the additional functional ingredients before the target is contacted with the oxidizing or non-oxidizing biocide. In other embodiments, the target can be contacted with the additional functional ingredients after the target is contacted with the corrosion inhibitor and oxidizing or non-oxidizing biocide (or a combined composition thereof). In still other embodiments, the target can be contacted with the additional functional ingredients concurrently when the target is contacted with the corrosion inhibitor and oxidizing or non-oxidizing biocide (or a combined composition thereof). In such embodiments, the corrosion inhibitor and oxidizing or non-oxidizing biocide (or a combined composition thereof) provide effective corrosion inhibition without deleterious interaction with such additional functional ingredients, including for example scale inhibitors and/or friction reducers.

In an aspect, the methods can further comprise contacting the target with an additional corrosion inhibitor. However, in other embodiments no additional corrosion inhibitors are employed. Any suitable corrosion inhibitor can be used. In some embodiments, the corrosion inhibitor can be a phosphate ester, a derivative of the phosphate ester, a diacid, a derivative of the diacid, a quat amine, a derivative of the quat amine, an imidazoline, a derivative of the imidazoline, an alkyl pyridine, a derivative of the alkyl pyridine, a phosphonium salt, a derivative of the phosphonium salt, or a combination thereof. The corrosion inhibitor can be used at any suitable level. In some embodiments, the corrosion inhibitor can be used at a level from about 1 ppm to about 50,000 ppm, e.g., about 1 to about 10 ppm, 10 to about 20 ppm, 20 to about 30 ppm, 30 to about 40 ppm, 40 to about 50 ppm, 50 to about 60 ppm, 60 to about 70 ppm, 70 to about 80 ppm, 80 to about 90 ppm, 90 to about 100 ppm, 100 to about 150 ppm, 150 to about 200 ppm, 200 to about 250 ppm, 250 to about 300 ppm, 300 to about 350 ppm, 350 to about 400 ppm, 400 to about 450 ppm, 450 to about 500 ppm, 500 to about 550 ppm, 550 to about 600 ppm, 600 to about 650 ppm, 650 to about 700 ppm, 700 to about 750 ppm, 750 to about 800 ppm, 800 to about 850 ppm, 850 to about 900 ppm, 900 to about 950 ppm, 950 to about 1,000 ppm, 1,000 to about 1,500 ppm, 1,500 to about 2,000 ppm, 2,000 to about 2,500 ppm, 2,500 to about 3,000 ppm, 3,000 to about 3,500 ppm, 3,500 to about 4,000 ppm, 4,000 to about 4,500 ppm, or 4,500 to about 5,000 ppm, 5,000 to about 5,500 ppm, 5,500 to about 6,000 ppm, 6,000 to about 6,500 ppm, 6,500 to about 7,000 ppm, 7,000 to about 7,500 ppm, 7,500 to about 8,000, 8,000 to about 8,500 ppm, 8,500 to about 9,000 ppm, 9,000 to about 9,500 ppm, or 9,500 to about 10,000 ppm.

In further embodiments, the methods of the invention can further be employed to reduce microbial population in and/or on the target or the treated target composition in an amount greater than that the magnitude provided as a result of the oxidizing or non-oxidizing biocide, namely a percarboxylic acid employed without the corrosion inhibitor. In some embodiments, the present methods can be used to reduce microbial population in and/or on the target or the treated target composition by at least one log 10, two log 10, three log 10, four log 10, five log 10, or more. In other embodiments, the level of a microorganism, if present in and/or on the target or the treated target composition, can be stabilized or reduced by the present methods. For example, at least 10%, 20%, 30%, 40%, 50%, 60%, 70%, 80%, or 90% or more of the microorganism, if present in and/or on the target or the treated target composition, can be killed, destroyed, removed and/or inactivated by the present methods.

In further embodiments, the methods of treating a target, namely a water source, can further comprise the step of monitoring a concentration(s) of the oxidizing or non-oxidizing biocide, namely a peroxycarboxylic acid. Such monitoring may be conducted in any suitable manner. In some embodiments, the concentrations of the oxidizing biocide such as a peroxycarboxylic acid and/or hydrogen peroxide can be monitored using a kinetic assay procedure, e.g., the exemplary procedure disclosed in U.S. Pat. Nos. 8,017,409 and 8,236,573, which are hereby incorporated by reference in their entirety. The monitoring step may also determine the concentrations of peroxycarboxylic acid and/or hydrogen peroxide in the presence of other additional functional ingredients, such as acidulants, one or more stabilizing agents, surfactants, corrosion inhibitors, or other ingredients which may be present in the use composition or adding to the target in a contacting step.

In further embodiments, the methods of treating a target, namely a water source, can further comprise the step of disposing of the treated water source. The present methods can further comprise directing the treated water source into a subterranean environment, e.g., a subterranean environment that comprises a well.

Additional Beneficial Effects of the Methods of Use in Water Treatment

Beneficially, in some aspects, the methods of using a corrosion inhibitor beneficially provide synergistic increases in biocidal activity of the system.

In a further aspect, the methods of use provide a corrosion inhibitor for use that does not negatively interfere with friction reducers, viscosity enhancers and/or other functional ingredients. In a further aspect, the methods of use do not negatively interfere with any additional functional agents utilized in the water treatment methods, including for example, scale inhibitors, descaling agents and the like. The compositions administered according to the invention provide extremely effective corrosion inhibition without adversely affecting the functional properties of any additive polymers of an aqueous system. Beneficially, the non-deleterious effects of the corrosion inhibitor and oxidizing or non-oxidizing biocide on the various functional ingredients used in water treatment methods are achieved regardless of the make-up of the water source in need of treatment.

In an additional aspect, the methods of use prevent the contamination of systems, such as well or reservoir souring. In further aspects, the methods of use prevent microbiologically-influenced corrosion of the systems upon which it is employed.

In further aspects, the methods of are suitable for anti-corrosion benefits while providing antimicrobial efficacy against a broad spectrum of microorganisms, providing broad spectrum bactericidal and fungistatic activity. For example, the peracid biocides of this invention provide broad spectrum activity against wide range of different types of microorganisms (including both aerobic and anaerobic microorganisms), including bacteria, yeasts, molds, fungi, algae, and other problematic microorganisms associated with oil- and gas-field operations. Exemplary microorganisms susceptible to the peracid compositions of the invention include, gram positive bacteria (e.g., *Staphylococcus aureus, Bacillus* species (sp.) like *Bacillus subtilis, Clostridia* sp.), gram negative bacteria (e.g., *Escherichia coli, Pseudomonas* sp., *Klebsiella pneumoniae, Legionella pneumophila, Enterobacter* sp., *Serratia* sp., *Desulfovibrio* sp., and *Desulfotomaculum* sp.), yeasts (e.g., *Saccharomyces cerevisiae* and *Candida albicans*), molds (e.g., *Aspergillus niger, Cephalosporium acremonium, Penicillium notatum,* and *Aureobasidium pullulans*), filamentous fungi (e.g., *Aspergillus niger* and *Cladosporium resinae*), algae (e.g., *Chlorella vulgaris, Euglena gracilis,* and *Selenastrum capricornutum*), and other analogous microorganisms and unicellular organisms (e.g., phytoplankton and protozoa).

In still further additional aspects, the methods provide oxidant properties. Water sources are often rich in malodorous compounds of reduced sulfur, nitrogen or phosphorous. A strong oxidant such as the compositions disclosed herein converts these compounds efficiently to their odor free derivatives e.g. the sulfates, phosphates and amine oxides. These same properties are very useful in the pulp and paper industry where the property of bleaching is also of great utility.

All publications and patent applications in this specification are indicative of the level of ordinary skill in the art to which this invention pertains. All publications and patent applications are herein incorporated by reference to the same extent as if each individual publication or patent application was specifically and individually indicated as incorporated by reference.

EXAMPLES

Embodiments of the present invention are further defined in the following non-limiting Examples. It should be understood that these Examples, while indicating certain embodiments of the invention, are given by way of illustration only. From the above discussion and these Examples, one skilled in the art can ascertain the essential characteristics of this invention, and without departing from the spirit and scope thereof, can make various changes and modifications of the embodiments of the invention to adapt it to various usages and conditions. Thus, various modifications of the embodiments of the invention, in addition to those shown and described herein, will be apparent to those skilled in the art from the foregoing description. Such modifications are also intended to fall within the scope of the appended claims.

Bubble Cell Test Procedure

The bubble test was designed to evaluate the partitioning properties of new corrosion inhibitor formulations, i.e., how quickly and to what extent in the multiphase system the chemicals will enter the water phase under stagnant conditions where the corrosion reaction takes place. With respect to the field conditions, this test simulates low profile areas, such as dead legs and water traps where no or very limited mixing exists, and the performance of an inhibitor is primarily determined by its capability to partition into the water phase. A synthetic or produced field brine is placed in a specially designed glass kettle where it is stirred at a low speed using a magnetic stir bar. The solution in the kettle is purged with the test gas (such as $CO_2$ when simulating sweet systems) and heated to the test temperature.

The corrosion rate is measured by a Linear Polarization Resistance (LPR) technique. An electrochemical probe accommodating three steel electrodes is used to obtain the values of polarization resistance, $R_p$. The data acquisition software converts the data obtained into the corrosion rate in mils per year (MPY). After the probe has been immersed into the brine, a measured volume of crude oil or synthetic hydrocarbon simulating an oil-phase is carefully introduced on top of the brine and the measurement is started. Typically, the system is allowed to equilibrate for several hours during which time the uninhibited corrosion rate baseline is obtained. Then, an inhibitor is injected into the hydrocarbon phase so that it must migrate through the oil into the aqueous phase. A typical testing time period is 24 hours, however, experiments can be run for up to several days. The typical corrosion profile obtained from bubble cell experiments is shown in FIG. 1. All events are shown as numbered arrows.

The baseline corrosion rate is recorded at arrow #1. After the corrosion inhibitor is added, the corrosion rate for the corrosion protected brine was recorded at the time indicated by the arrow #2. Corrosion rate for biocide addition was recoded at arrow #3; corrosion rates for 2 hrs, 8 hrs, and 17 hrs after biocide addition were recorded at arrow #4, #5 and #6 respectively.

To calculate percentage protection by a corrosion inhibitor, the corrosion rate of corrosion inhibitor+biocide for time points at each event was compared to the corrosion rate for each event with biocide alone. Percentage protection was calculated by using the formula % protection=100*((corrosion rate without CI−corrosion rate with CI)/corrosion rate without CI (1)).

Biocide Efficiency

Biocidal efficiency of the biocide and biocide in conjunction with corrosion inhibitors were analyzed using fluorescence to indirectly detect the amount of ATP in a given sample. ATP provides a direct correlation to live bacteria (1 fg of ATP=1 cell). Through a standard curve, it is the possible to translate the amount of ATP in a given sample to the number of cells/mL in a given sample. Percentage kill was calculated by normalizing the detected bacterial numbers in a biocide or a biocide and corrosion inhibitor treated sample to untreated sample. For evaluation of corrosion protection and biocidal efficiency in the following Examples the corrosion inhibitor molecules listed in Tables 2 and 3 were used.

TABLE 2

(Corrosion inhibitor molecules and the concentration of stock solution (chemicals were used at 120 ppm product dosage))

| Molecule | Active % |
|---|---|
| Cocoamphodiprionate sodium salt COCOAP | 20 |
| Hyperbranched Polyesteramide | 50 |
| Cocoglucoside dimethicone | 17.5 |
| 2-hydroxylethyl-N-methylbutane-1-sulphonamide | 24.25 |
| Dodecenyl succinic anhydride | 50 |
| Cetyl pyridinium bromide | 20 |
| Cetyl pyridinium chloride | 20 |
| Benzyl, didethyl-dodecyl- ammonium chloride (quaternary ammonium compound) (Control 1) | 92 |
| Fatty acids, tall-oil, reaction products with n-(2 - aminoethyl)-1,2-ethanediamine & 2-propenoic acid (Acrylated imidazoline) (Control 2) | 80 |
| Mercaptoethanol (Control 3 - Synergist) | 100 |

TABLE 3

(Biocides and their compositions (biocides were used at 100 ppm product dosage))

| 1 | Biocide 1 | 15% PAA, 10% Peroxide |
| 2 | Biocide 2 | 7.5% PFA, 0.2% peroxide |
| 3 | Biocide 3 | 75% THPS |
| 4 | Biocide 4 | 50% Gluteraldehyde |

Example 1

Evaluation of Cocoamphodiprionate Sodium Salt (COCOAP) Corrosion Inhibitor

A 1 L glass kettle is filled with a given amount of brine mixed with produced water. The produced water brine is then heated using a stir place while de-aerating with Carbon dioxide. Corrosion rate is monitored via LPR probes. Corrosion coupons are cleaned with successive sonication in Xylene and acetone after which they are assembled in to LPR probes. The probes are then attached to the Gamry controller. After a couple of hours of de-aeration with $CO_2$, uninhibited corrosion rate is collected for a couple of hours after which 120 ppm of corrosion inhibitor is added. Corrosion inhibited corrosion rate is monitored for at least 2 hrs after which biocide is added. The test after this is run overnight, typically for 16-20 hrs and data collected every 15 minutes. Corrosion rate for each corrosion inhibitor was monitored for the evaluated biocides.

Corrosion data for produced water brine treated with 120 ppm of Cocoamphodiprionate sodium salt (20% solution) and 100 ppm of biocides is tabulated in Table 4 (Corrosion rate in MPY of COCOAP).

TABLE 4

| | Corrosion rate in MPY | | | | |
|---|---|---|---|---|---|
| Cocoamphodiprionate | Biocide 1 | Biocide 2 | Biocide 3 | Biocide 4 | $CO_2$* |
| Background | 4.06 | 1.097 | 4.7840 | 7.5730 | 99.6400 |
| CI | 4.888 | 0.5222 | 6.9830 | 4.4020 | 98.5400 |
| Biocide | 48.9 | 3.966 | 5.9450 | 3.9920 | |
| Biocide + 2 hrs | 15.8 | 1.436 | 3.2560 | 3.6720 | 23.7300 |
| Biocide + 8 hrs | 1.415 | 0.6276 | 7.3900 | 3.2270 | 6.9350 |
| Biocide + 17 hrs | 0.81 | 0.4382 | 19.2800 | 2.8500 | 5.9230 |

*No biocide was added in the $CO_2$ only tests.

The addition of 120 ppm of Cocoamphodiprionate (Table 4) results in significant protection of the carbon steel coupons compared to biocide treated produced water brine alone results in corrosion of C1018 carbon steel coupons (Table 12). This is apparent in samples treated with Biocide 1 (FIG. 2A and Table 4), Biocide 3 (FIG. 3A and Table 4), Biocide 4 (FIG. 3B and Table 4) and $CO_2$ (FIG. 4A and Table 4), as $CO_2$ in water generated carbonic acid is known to cause generalized corrosion. Corrosion protection by Cocoamphodiprionate is also seen when compared to samples treated with 120 ppm of Control 1 (Table 13) and Control 2 (Table 14).

Figure 2A:
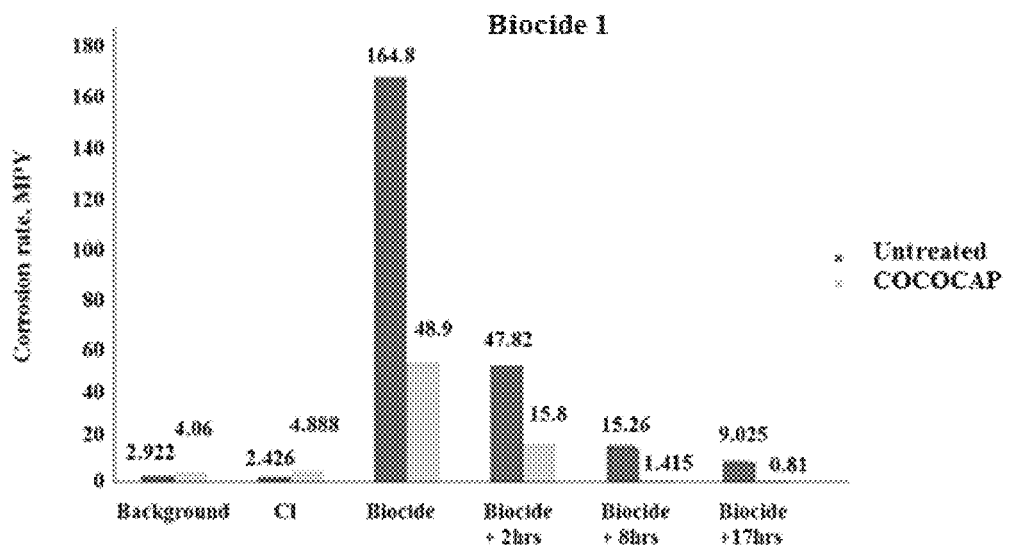
FIGS. 2A-2B show the results from corrosion testing for biocide 1 (FIG. 2A) and biocide 2 (FIG. 2B) in combination with corrosion inhibitor molecule cocoamphodiproprionate sodium salt according to an embodiment of the invention.
Figure 2B:
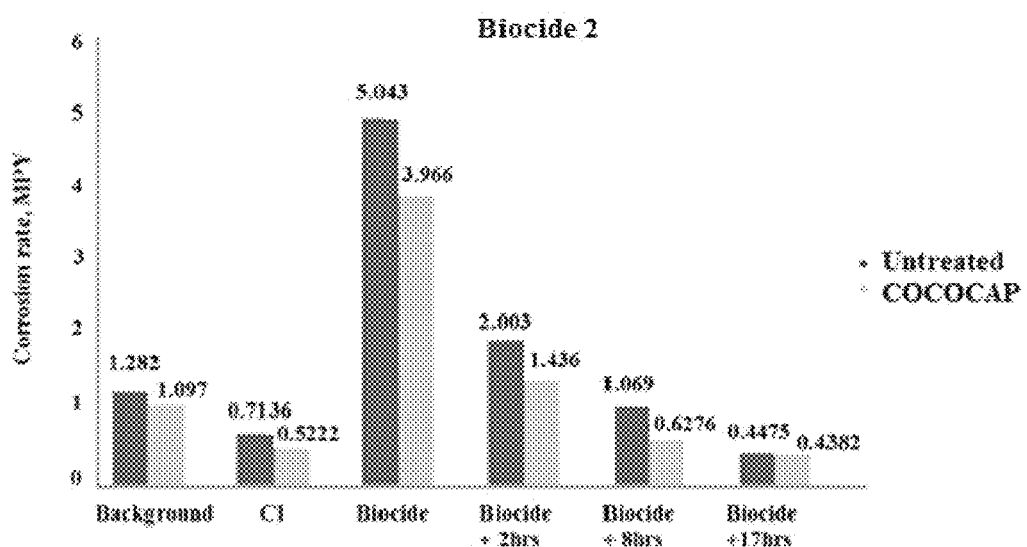

FIG. 2 shows the results from corrosion testing for biocide 1 (FIG. 2A) and biocide 2 (FIG. 2B) in combination with corrosion inhibitor molecule, cocoamphodiprionate sodium salt. As can be seen in FIGS. 2A and 2B, biocide treated produced water brine alone results in corrosion of C1018 carbon steel coupons. However, the addition of 120 ppm of cocoamphodiprionate sodium salt results in protection of the C1018 carbon steel coupons. Furthermore, while the overall corrosion protection of biocide 2 treated carbon steel coupons treated with cocoamphodiprionate (FIG. 2B) is comparable to that of untreated samples, the raw data indicates that the corrosion rate is well within the acceptable range of corrosion protection (<4 MPY) for an effective corrosion inhibitor.

Figure 3A:
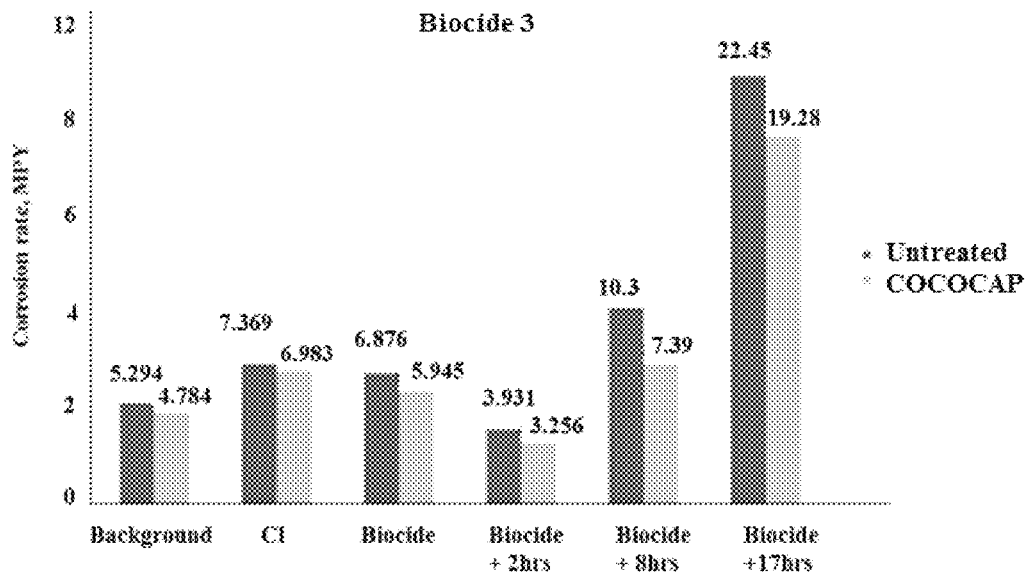
FIGS. 3A-3B show the results from corrosion testing for biocide 3 (FIG. 3A) and biocide 4 (FIG. 3B) in combination with corrosion inhibitor molecule cocoamphodiproprionate sodium salt according to an embodiment of the invention.
Figure 3B:
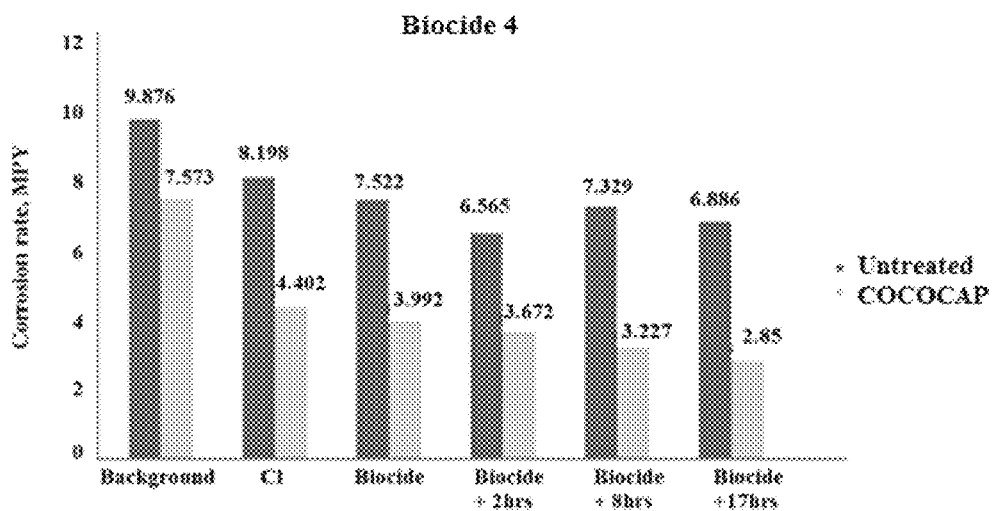

FIG. 3 shows the results from corrosion testing for biocide 3 (FIG. 3A) and biocide 4 (FIG. 3B) in combination with corrosion inhibitor molecule, cocoamphodiprionate sodium salt. The results indicate that cocoamphodiprionate provides corrosion protection compared to untreated samples.

Figure 4A:
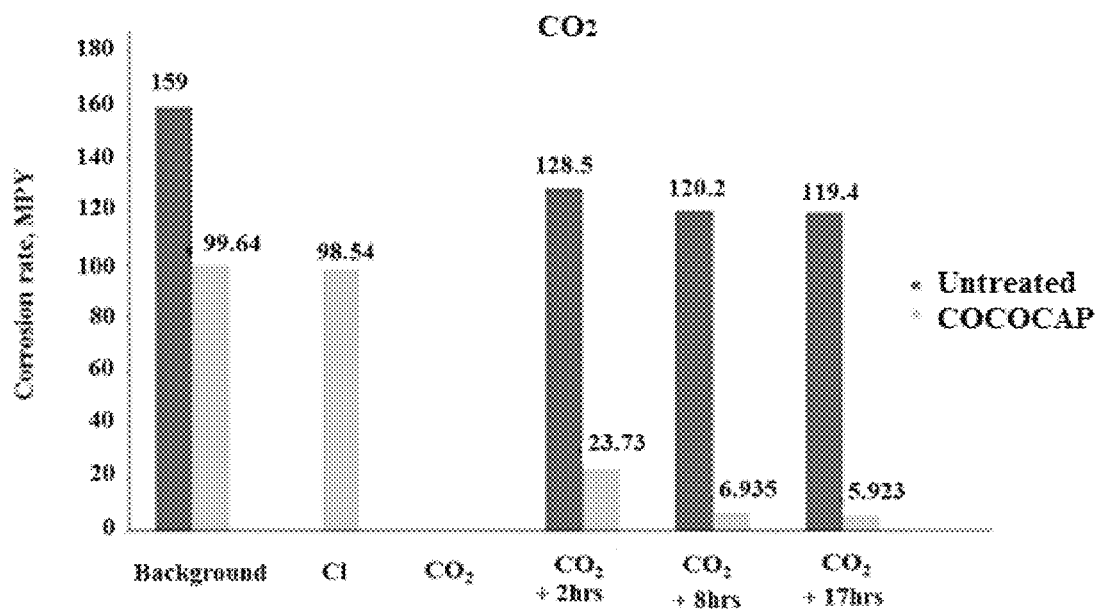
FIG. 4A shows a data plot showing cocoamphodiproprionate sodium salt corrosion protection against $CO_2$ corrosion according to an embodiment of the invention.
Figure 4B:
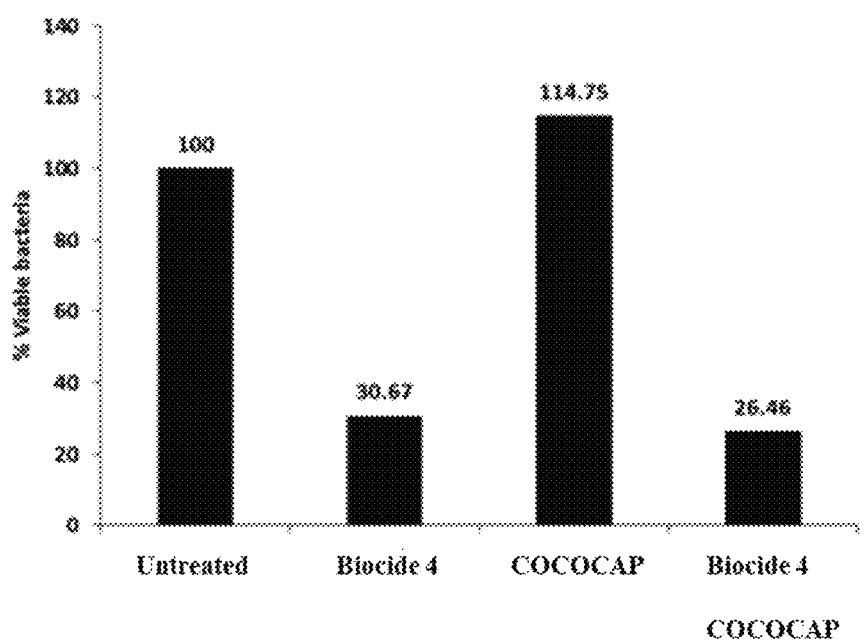
FIG. 4B shows a data plot showing cocoamphodiproprionate sodium salt corrosion protection is capable of an increase in the biocidal properties of biocide 4 according to an embodiment of the invention.

FIG. 4A plots the data showing cocoamphodiprionate sodium salt corrosion protection against $CO_2$ corrosion. $CO_2$ in water generated carbonic acid that is known to cause generalized corrosion. As seen in FIG. 4A, the corrosion rate of C1018 carbon steel coupons are significantly reduced when treated with cocoamphodiproprionate sodium salt. FIG. 4B tests the combinatory effects of biocide 4 and cocoamphodiproprionate sodium salt to produce anti-microbial properties. FIG. 4B provides cocoamphodiproprionate sodium salt is capable of a modest increase in the biocidal properties of biocide 4 but is not efficient in reducing the number of viable microorganisms by itself. Taken together Table 4 and FIGS. 2, 3 and 4 provide evidence for corrosion protection by Cocoamphodiproprionate.

Example 2

Evaluation of Hyperbranched Polyesteramide Corrosion Inhibitor

Experiments used to assess corrosion inhibition properties were performed as described previously in Example 1, using 120 ppm of hyperbranched polyesteramide and 100 ppm of biocides. Corrosion data for hyperbranched polyesteramide added to different biocides is tabulated in Table 5.

TABLE 5

(Corrosion rate of hyperbranched polyesteramide)

| Hyperbranched polyesteramide | Corrosion rate in MPY | | | | |
|---|---|---|---|---|---|
| | Biocide 1 | Biocide 2 | Biocide 3 | Biocide 4 | $CO_2$* |
| Background | 4.123 | 5.063 | 4.5010 | 10.8500 | 104.4000 |
| CI | 3.26 | 1.931 | 4.1100 | 3.3890 | 107.2000 |
| Biocide | 76.13 | 6.512 | 2.9370 | 3.2410 | |
| Biocide + 2 hrs | 14.36 | 1.694 | 2.6390 | 3.0320 | 103.5000 |
| Biocide + 8 hrs | 1.898 | 2.787 | 4.5730 | 2.8150 | 116.8000 |
| Biocide + 17 hrs | 1.494 | 1.349 | 5.9450 | 2.5780 | 127.8000 |

*No biocide was added in the CO2 only tests

Figure 5A:
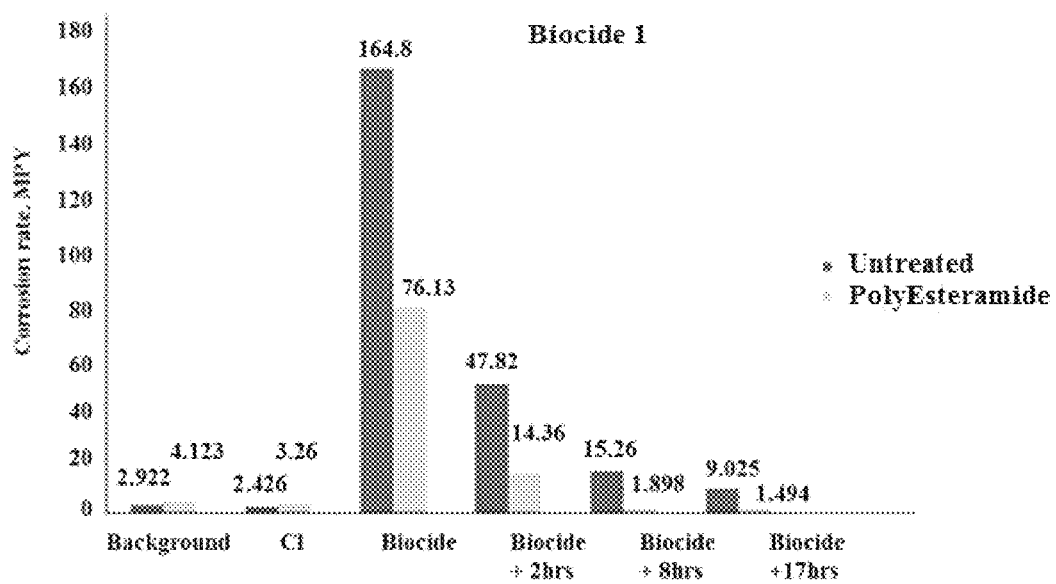
FIGS. 5A-5B show the results from corrosion testing for biocide 1 (FIG. 5A) and biocide 2 (FIG. 5B) in combination with corrosion inhibitor molecule hyperbranched polyesteramide.
Figure 5B:
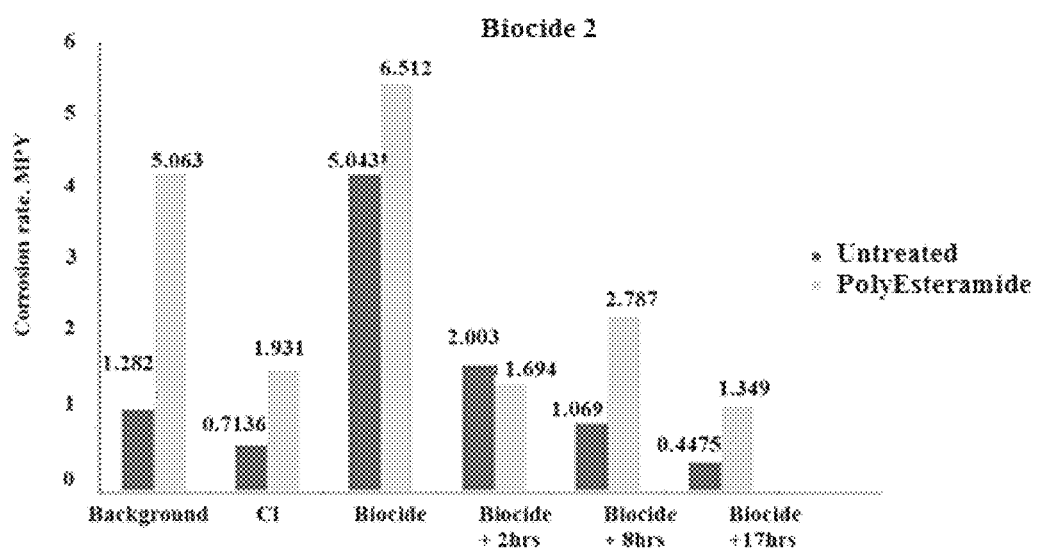
Figure 6A:
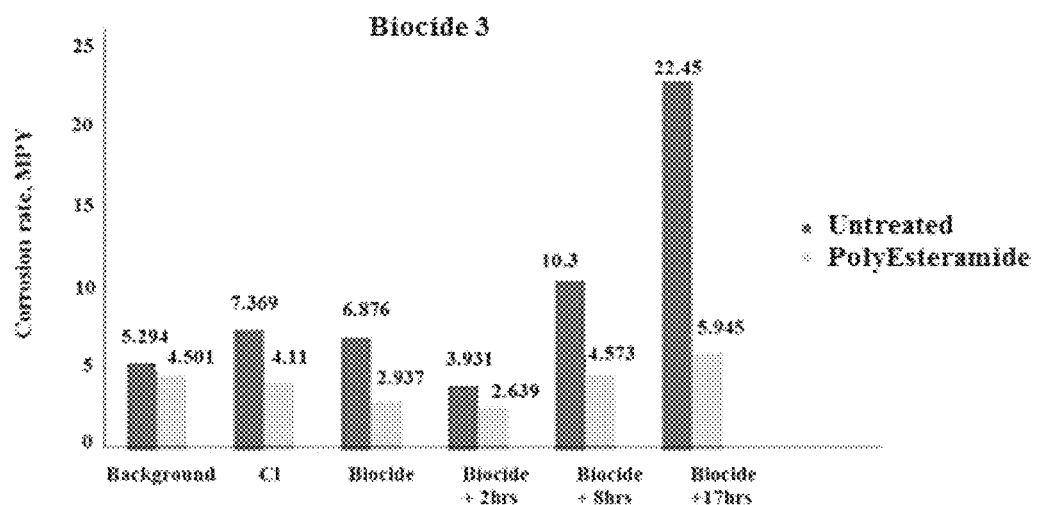
FIGS. 6A-6B shows the corrosion protective properties of hyperbranched polyesteramide when treated with biocide 3 (FIG. 6A) and biocide 4 (FIG. 6B) according to an embodiment of the invention.
Figure 6B:
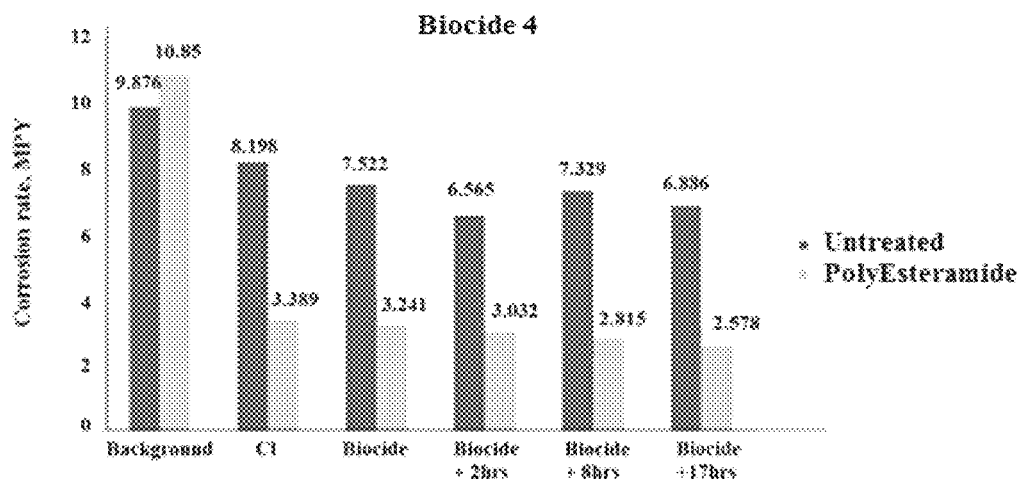

Table 5 and FIGS. 5, 6, and 7 provide evidence for the corrosion protection conferred by the addition of hyperbranched polyesteramide on the corrosion rate of 1018 carbon steel compared to untreated samples (no corrosion inhibitor addition) (Table 12). Biocide treated produced water bine alone results in corrosion of C1018 carbon steel coupons. However, the addition of 120 ppm of hyperbranched polyesteramide results in significant protection of the carbon steel coupons. This is apparent in samples treated with Biocide 1 (FIG. 5A and Table 5), Biocide 3 (FIG. 6A and Table 5), and Biocide 4 (FIG. 6B and Table 5).

FIG. 5 shows the results from corrosion testing for biocide 1 (FIG. 5A) and biocide 2 (FIG. 5B) in combination with corrosion inhibitor molecule, hyperbranched polyeasteramide. FIG. 5A provides evidence for corrosion protection conferred by the addition of hyperbranched polyesteramide on the corrosion rate of 1018 carbon steel compared to untreated samples. However, even though the overall corrosion protection for biocide 2 treated with hyperbranched polyesteramide is lower than the untreated samples (FIG. 5B), the corrosion rate is well within the acceptable range of corrosion protection for an effective corrosion inhibitor (<4 MPY).

FIG. 6 provides further evidence of the corrosion protective properties of hyperbranched polyesteramide when treated with biocide 3 (FIG. 6A) and biocide 4 (FIG. 6B). As can be seen in the graphs of FIG. 6 the overall corrosion protection of the C1018 carbon steel coupons treated hyperbranched polyesteramide is higher than untreated controls.

Figure 7A:
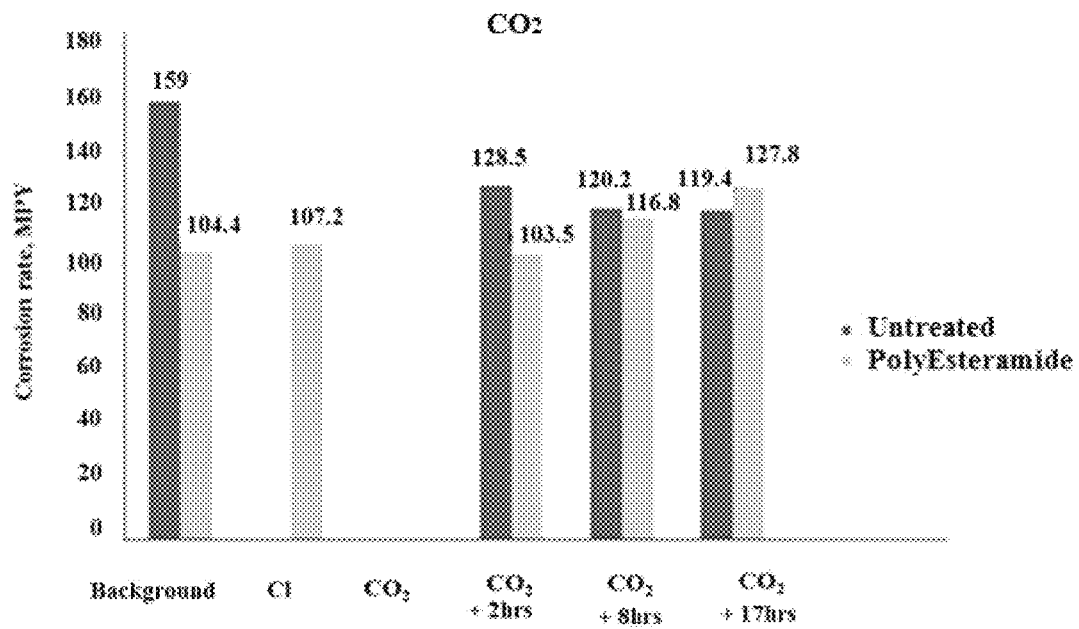
FIG. 7A shows a data plot showing corrosion protective properties of hyperbranched polyesteramide against generalized corrosion produced by $CO_2$.
Figure 7B:
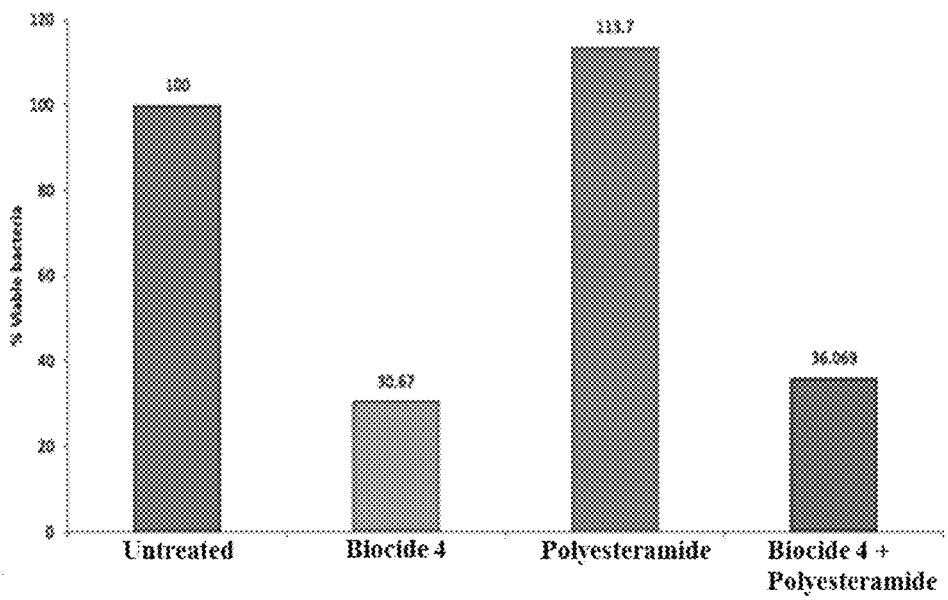
FIG. 7B shows a data plot showing hyperbranched polyesteramide does not provide any biocidal efficiency alone nor when dosed together with biocide 4.

Additionally, corrosion protection of hyperbranched polyesteramide can be seen when compared to samples treated with 120 ppm of CONTROL 1 (Table 13) and CONTROL 2 (Table 14). FIG. 7A tests the corrosion protective properties of hyperbranched polyesteramide against generalized corrosion produced by $CO_2$. The data plotted in FIG. 7A shows that hyperbranched polyesteramide does not produce a lower corrosion rate compared to untreated controls. FIG. 7B shows hyperbranched polyesteramide does not provide any biocidal efficiency alone nor when dosed together with biocide 4. Taken together these data provide evidence for the corrosion protection conferred by hyperbranched polyesteramide.

Example 3

Evaluation of Cocoglucoside Dimethicone (COCOGDM) Corrosion Inhibitor

Experiments used to assess corrosion inhibition properties were performed as described previously in Example 1, using 120 ppm of Cocoglucoside dimethicone and 100 ppm of biocides. Corrosion data for Cocoglucoside dimethicone added to different biocides is tabulated in Table 6.

TABLE 6

(Corrosion rate of Cocoglucoside dimethicone)

| Cocoglucoside dimethicone | Corrosion rate in MPY | | | | |
|---|---|---|---|---|---|
| | Biocide 1 | Biocide 2 | Biocide 3 | Biocide 4 | $CO_2$* |
| Background | 5.493 | 2.002 | 5.54 | 8.93 | 104.0000 |
| CI | 4.271 | 0.8242 | 3.28 | 2.60 | 111.4000 |
| Biocide | 86.9 | 3.055 | 2.53 | 4.23 | |
| Biocide + 2 hrs | 22.74 | 1.255 | 3.37 | 4.01 | 110.6000 |
| Biocide + 8 hrs | 3.729 | 0.8096 | 8.87 | 3.54 | 143.7000 |
| Biocide + 17 hrs | 2.648 | 0.5581 | 20.16 | 3.08 | 167.5000 |

*No biocide was added in the $CO_2$ only tests

Figure 8A:
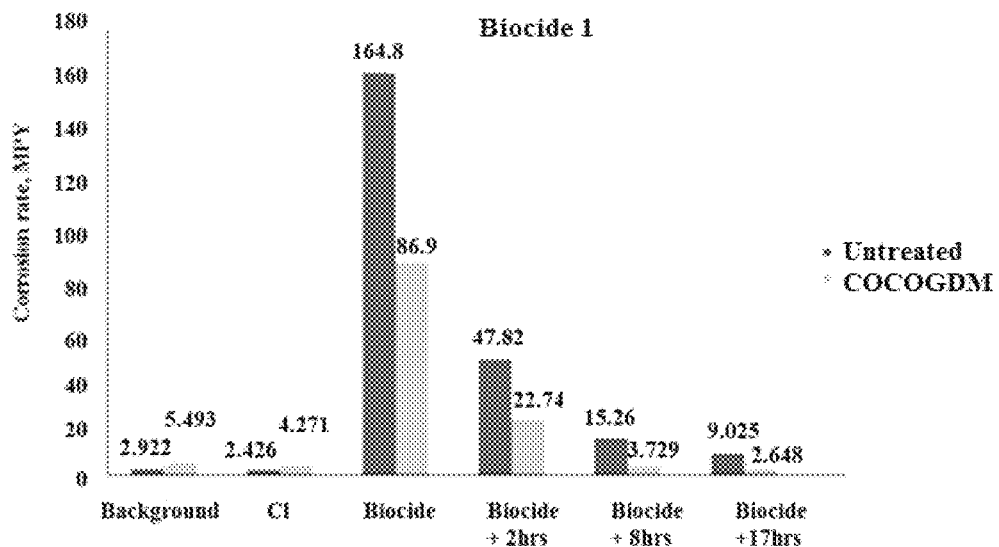
FIGS. 8A-8B show the results from corrosion testing for biocide 1 (FIG. 8A) and biocide 2 (FIG. 8B) in combination with corrosion inhibitor molecule cocoglucoside dimethicone.
Figure 8B:
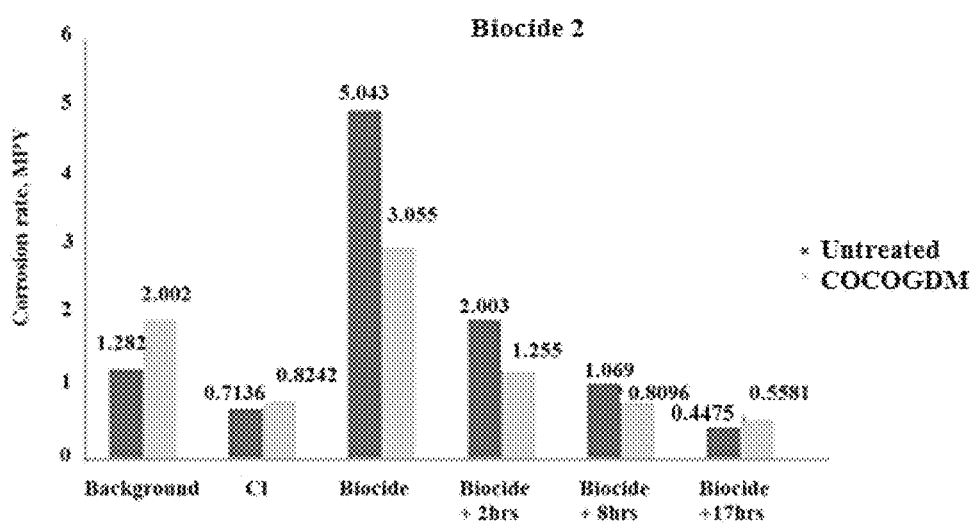
Figure 9A:
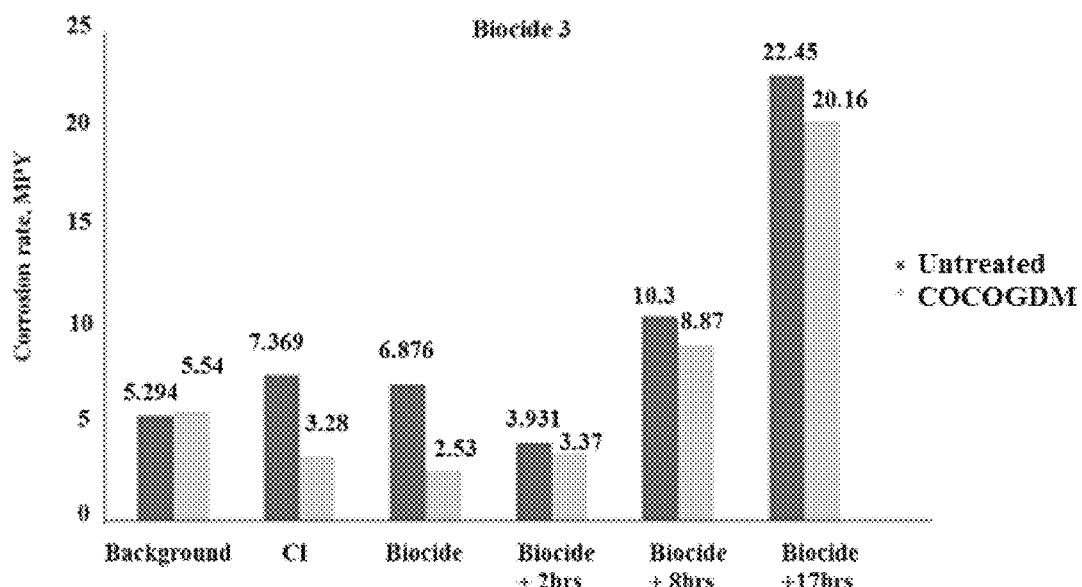
FIGS. 9A-9B show further evidence of the corrosion protective properties of cocoglucoside dimethicone when treated with biocide 3 (FIG. 9A) and biocide 4 (FIG. 9B).
Figure 9B:
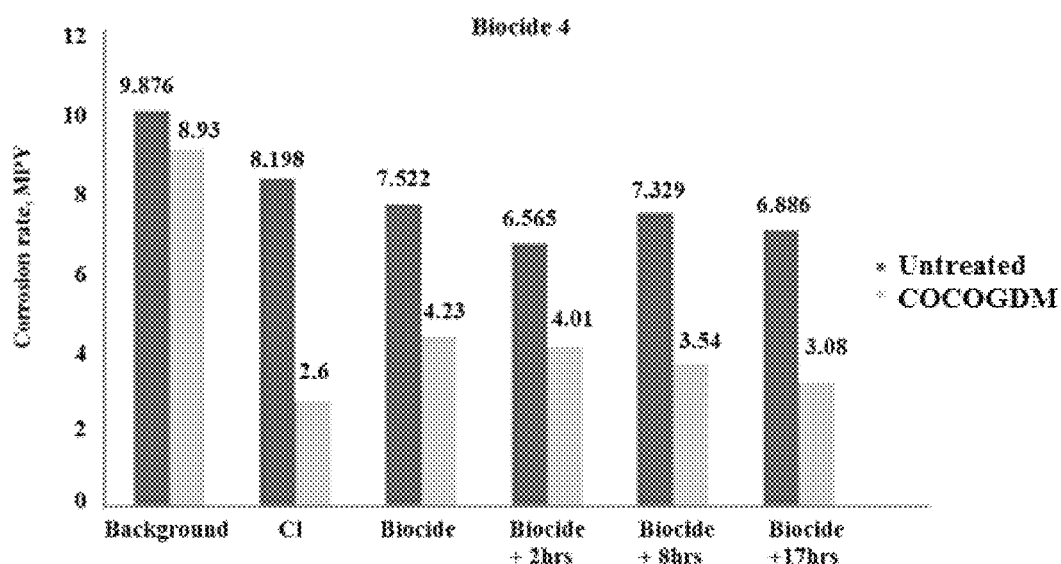

Table 6 and FIGS. 8, 9, and 10 provide evidence for the corrosion protection conferred by Cocoglucoside dimethicone addition on the corrosion rate of 1018 carbon steel compared to untreated samples (Table 12). This is apparent in samples treated with Biocide 1 (FIG. 8A and Table 6), Biocide 2 (FIG. 8B and Table 6), Biocide 3 (FIG. 9A and Table 6), and Biocide 4 (FIG. 9B and Table 6).

FIG. 8 shows the results from corrosion testing for biocide 1 (FIG. 8A) and biocide 2 (FIG. 8B) in combination with corrosion inhibitor molecule, cocoglucoside dimethicone. As can be seen in FIGS. 8A and 8B, biocide treated produced water bine alone results in corrosion of C1018 carbon steel coupons. However, the addition of 120 ppm of cocoglucoside dimethicone results in corrosion protection of the carbon steel coupons.

FIG. 9 shows further evidence of the corrosion protective properties of cocoglucoside dimethicone when treated with biocide 3 (FIG. 9A) and biocide 4 (FIG. 9B). As can be seen in the graphs of FIG. 9 the overall corrosion rate of the C1018 carbon steel coupons treated cocoglucoside dimethicone is lower than the untreated controls.

Figure 10A:
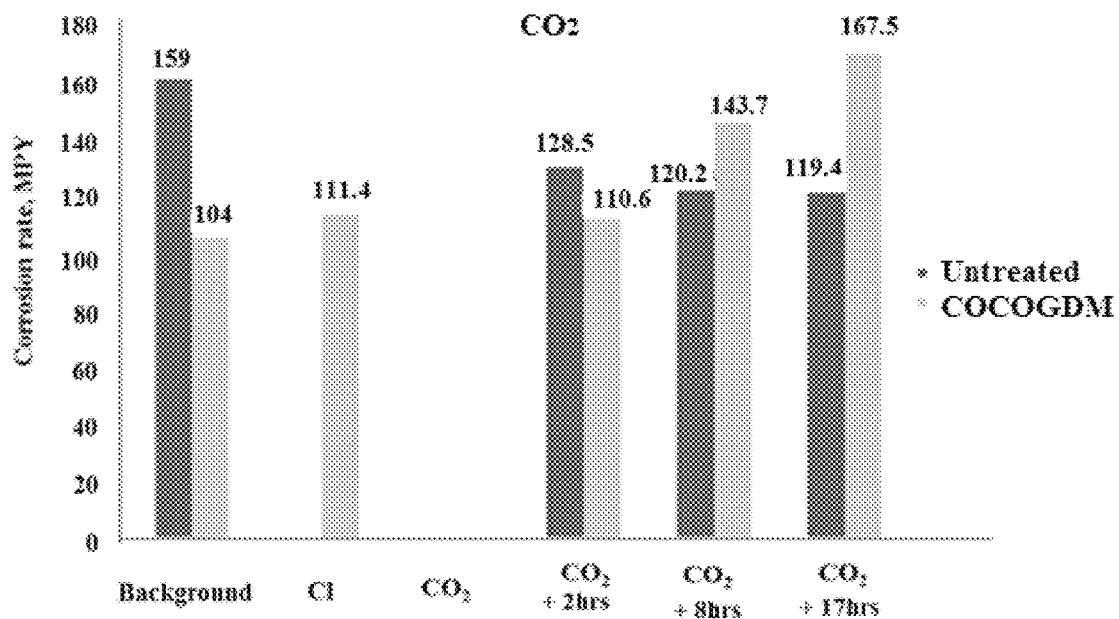
FIG. 10A shows the corrosion protective properties of cocoglucoside dimethicone against corrosion produced by $CO_2$ according to an embodiment of the invention.
Figure 10B:
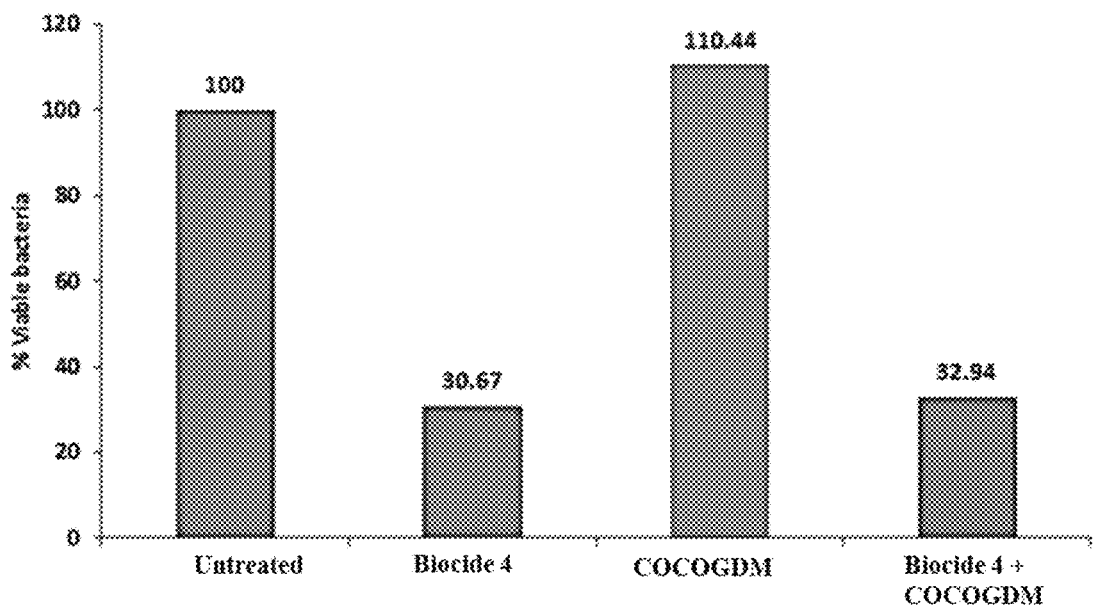
FIG. 10B shows cocoglucoside dimethicone does not provide any biocidal efficiency alone nor when dosed together with biocide 4 according to an embodiment of the invention.

Moreover, corrosion protection by Cocoglucoside dimethicone can be seen when compared to samples treated with 120 ppm of CONTROL 1 (Table 13) and CONTROL 2 (Table 14). FIG. 10A tests the corrosion protective properties of cocoglucoside dimethicone against corrosion produced by $CO_2$. FIG. 10A shows that cocoglucoside dimethicone generally does not produce a lower corrosion rate compared to untreated controls. FIG. 10B shows cocoglucoside dimethicone does not provide any biocidal efficiency alone nor when dosed together with biocide 4.

Example 4

Evaluation of 2-hydroxyethyl-N-methylbutane-1-sulphonamide (2-HNMBSA) Corrosion Inhibitor Experiments used to assess corrosion inhibition properties were performed as described previously in Example 1, using 120 ppm of 2-hydroxyethyl-N-methylbutane-1-sulphonamide and 100 ppm of biocides. Corrosion data for 2-hydroxyethyl-N-methylbutane-1-sulphonamide added to different biocides is tabulated in Table 7.

TABLE 7

(Corrosion rate of 2-hydroxyethyl-N-methylbutane-1-sulphonamide (2-HNMBSA))

| 2-hydroxyethyl-N-methylbutane-1-sulphonamide | Corrosion rate in MPY | | | | |
|---|---|---|---|---|---|
| | Biocide 1 | Biocide 2 | Biocide 3 | Biocide 4 | $CO_2$* |
| Background | 6.273 | 1.769 | 4.2880 | 7.5470 | 113.1000 |
| CI | 5.101 | 0.6859 | 3.8820 | 3.1740 | 111.6000 |
| Biocide | 122.9 | 2.01 | 2.7740 | 2.8890 | |
| Biocide + 2 hrs | 23.91 | 0.7841 | 3.4910 | 2.6270 | 102.5000 |
| Biocide + 8 hrs | 5.312 | 0.6327 | 5.1620 | 2.2090 | 47.4900 |
| Biocide + 17 hrs | 3.712 | 0.3224 | 8.8860 | 2.0730 | 37.5800 |

*No biocide was added in the $CO_2$ only tests

Figure 11A:
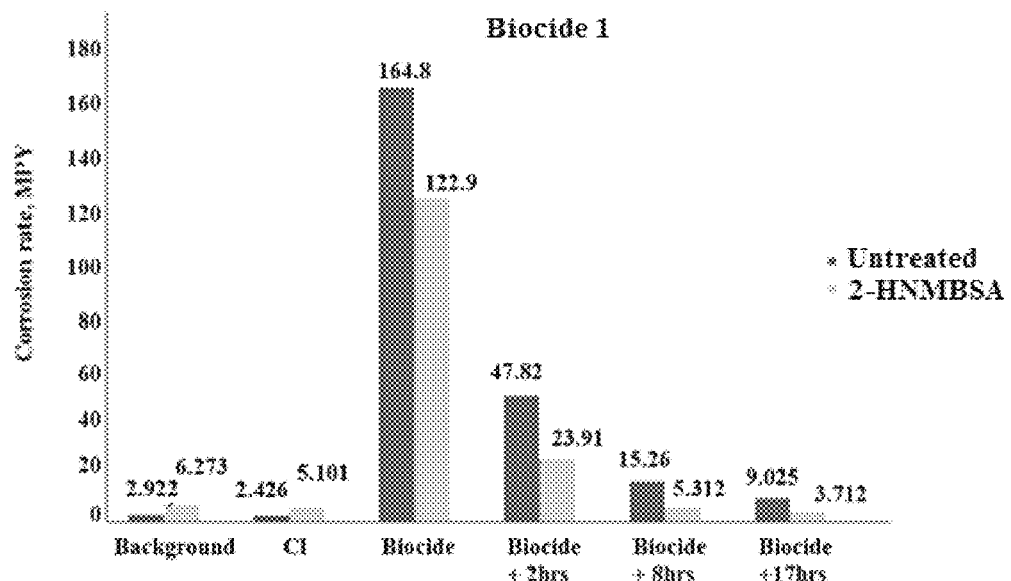
FIGS. 11A-11B show the results from corrosion testing for biocide 1 (FIG. 11A) and biocide 2 (FIG. 11B) in combination with corrosion inhibitor molecule 2-hydroxyl-ethyl-N-methylbutane-1-sulphonamide.
Figure 11B:
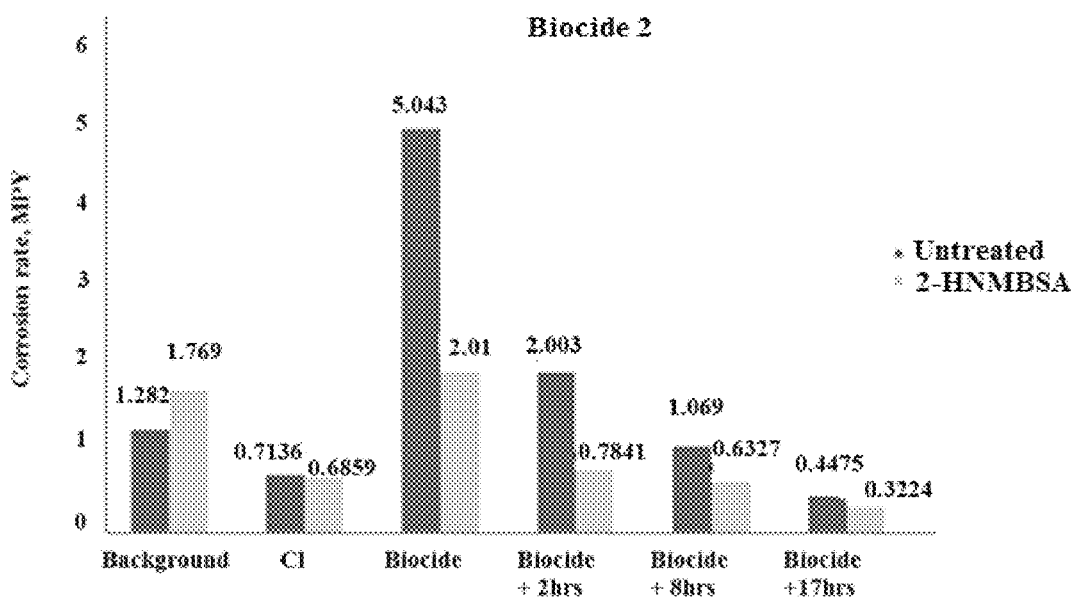
Figure 12A:
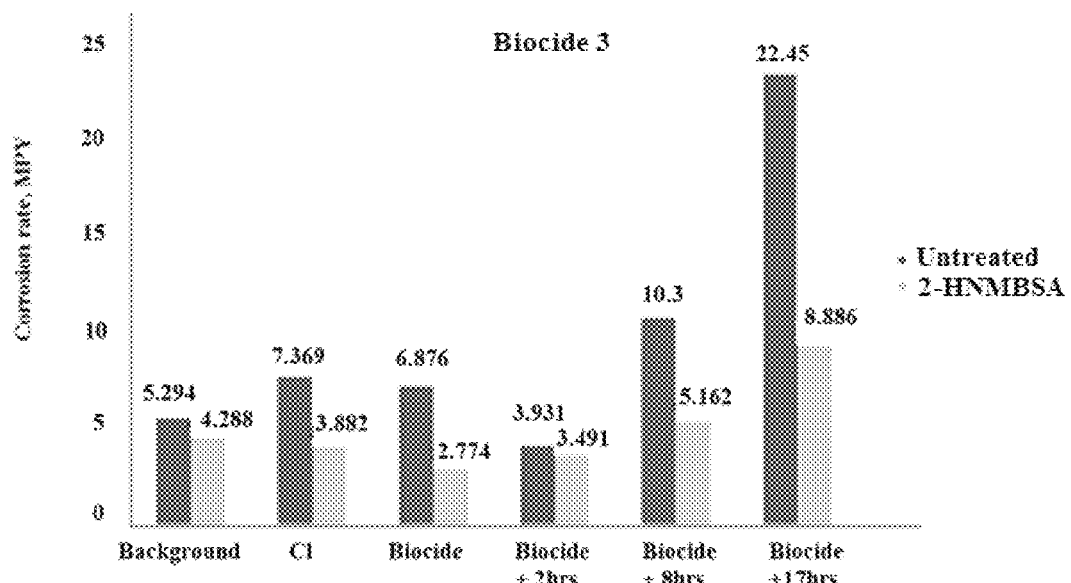
FIGS. 12A-12B show the results from corrosion testing for biocide 3 (FIG. 12A) and biocide 4 (FIG. 12B) in combination with corrosion inhibitor molecule 2-hydroxyl-ethyl-N-methylbutane-1-sulphonamide.
Figure 12B:
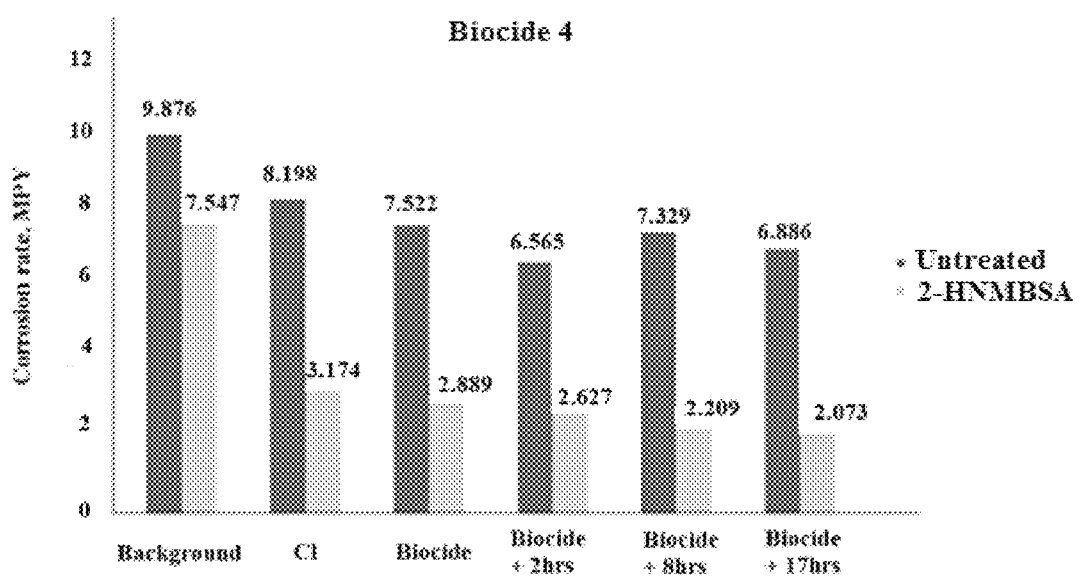
Figure 13A:
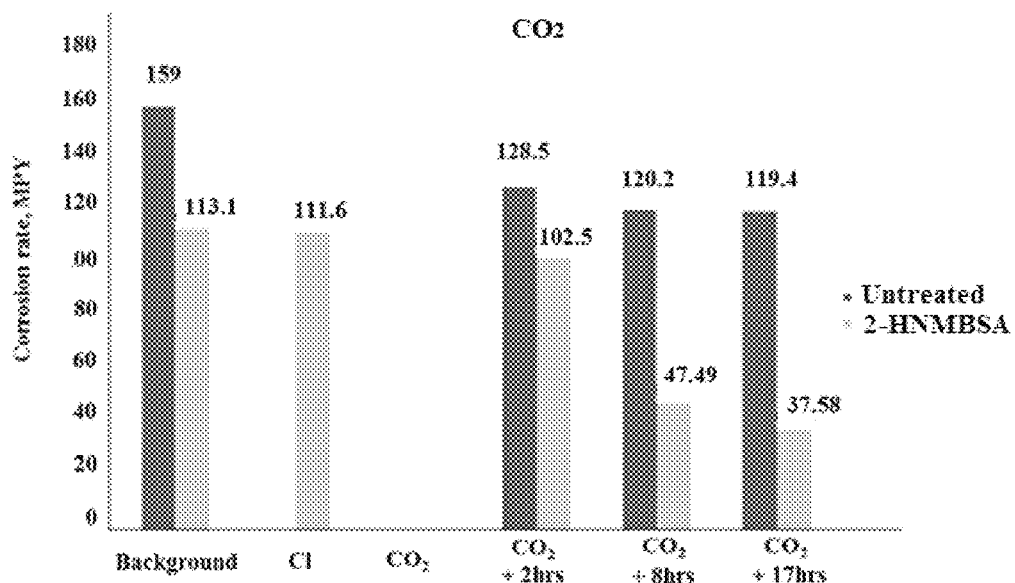
FIG. 13A plots the data showing corrosion protection of 2-hydroxylethyl-N-methylbutane-1-sulphonamide against $CO_2$ corrosion according to an embodiment of the invention.

Table 7 and FIGS. 11, 12, and 13 provide evidence for the protective properties of 2-hydroxyethyl-N-methylbutane-1-sulphonamide on the corrosion rate of 1018 carbon steel compared to untreated samples (Table 11). Specifically, this is apparent in samples treated with Biocide 1 (FIG. 11A and Table 7), Biocide 2 (FIG. 11B and Table 7), Biocide 3 (FIG. 12A and Table 7), Biocide 4 (FIG. 12B and Table 7), or untreated ($CO_2$) (FIG. 13A and Table 7). Furthermore, Silicone 2-hydroxyethyl-N-methylbutane-1-sulphonamide mediated corrosive protection can be seen when compared to samples treated with 100 ppm of CONTROL 1 (Table 12) and CONTROL 2 (Table 13).

FIG. 11 shows the results from corrosion testing for biocide 1 (FIG. 11A) and biocide 2 (FIG. 11B) in combination with corrosion inhibitor molecule, 2-hydroxyethyl-N-methylbutane-1-sulphonamide. Collectively, FIGS. 11A and 11B, provide evidence for the corrosion inhibiting properties of 2-hydroxyethyl-N-methylbutane-1-sulphonamide, as the rate of carbon steel coupon corrosion is significantly lower when treated in combination with 2-hydroxyethyl-N-methylbutane-1-sulphonamide compared to coupons treated with biocide 1 or biocide 2 alone.

FIG. 12 shows the results from corrosion testing for biocide 3 (FIG. 12A) and biocide 4 (FIG. 12B) in combination with corrosion inhibitor molecule, 2-hydroxyethyl-N-methylbutane-1-sulphonamide. Collectively, FIGS. 12A and 12B, provide evidence for the corrosion inhibiting properties of 2-hydroxyethyl-N-methylbutane-1-sulphonamide, as the rate of carbon steel coupon corrosion is significantly lower when treated in combination with 2-hydroxyethyl-N-methylbutane-1-sulphonamide compared to coupons treated with biocide 3 or biocide 4 alone.

Figure 13B:
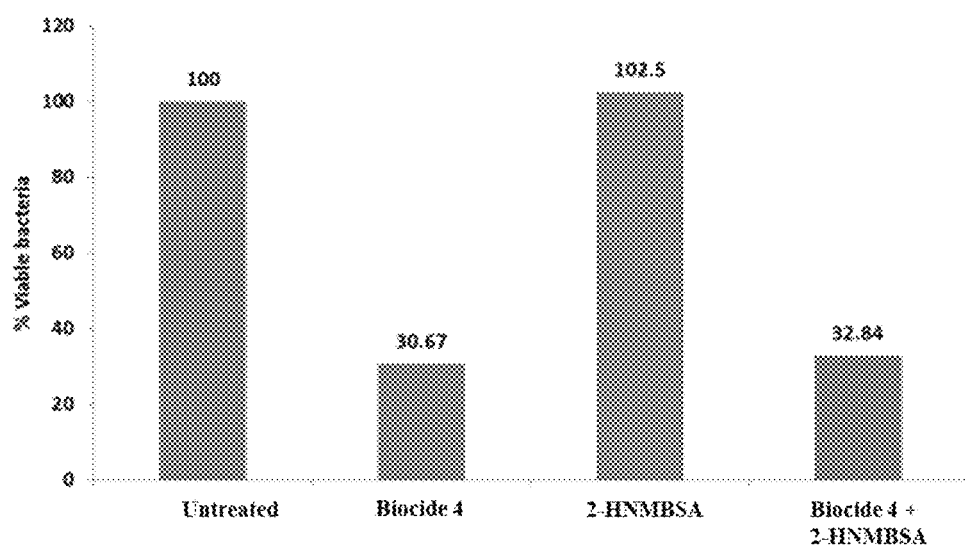
FIG. 13B shows 2-hydroxylethyl-N-methylbutane-1-sulphonamide does not have any biocidal properties either by itself or when used in conjunction with a biocide according to an embodiment of the invention.

FIG. 13A plots the data showing corrosion protection of 2-hydroxyethyl-N-methylbutane-1-sulphonamide against $CO_2$ corrosion. As can be seen by the data presented in FIG. 13A, 2-hydroxyethyl-N-methylbutane-1-sulphonamide is capable of reducing the corrosion rates of carbon steel coupons exposed against generalized corrosion produced by $CO_2$ compared to untreated controls. FIG. 13B shows 2-hydroxyethyl-N-methylbutane-1-sulphonamide does not have any biocidal properties either by itself or when used in conjunction with a biocide. Collectively these data are consistent for the support of the protective properties of 2-hydroxyethyl-N-methylbutane-1-sulphonamide against corrosion.

Example 5

Evaluation of Dodecyl Succinic Anhydride Corrosion Inhibitor

Experiments used to assess corrosion inhibition properties were performed as described previously in Example 1, using 120 ppm of Dodecyl succinic anhydride and 100 ppm of biocides. Corrosion data for Dodecyl succinic anhydride added to different biocides is tabulated in Table 8.

TABLE 8

(Corrosion rate of dodecenyl succinic anhydride)

| Dodecenyl succinic anhydride | Corrosion rate in MPY | | | | |
|---|---|---|---|---|---|
| | Biocide 1 | Biocide 2 | Biocide 3 | Biocide 4 | $CO_2$* |
| Background | 6.094 | 0.6071 | 4.6480 | 9.1110 | 99.3300 |
| CI | 5.961 | 0.5078 | 6.5540 | 5.2240 | 103.5000 |
| Biocide | 120.5 | 4.26 | 5.5460 | 4.6270 | |
| Biocide + 2 hrs | 23.83 | 1.776 | 3.4150 | 4.1640 | 97.1100 |
| Biocide + 8 hrs | 4.828 | 0.9521 | 2.3480 | 3.7450 | 121.8000 |
| Biocide + 17 hrs | 3.864 | 0.5356 | 1.8120 | 3.1680 | 135.9000 |

*No biocide was added in the $CO_2$ only tests

Figure 14A:
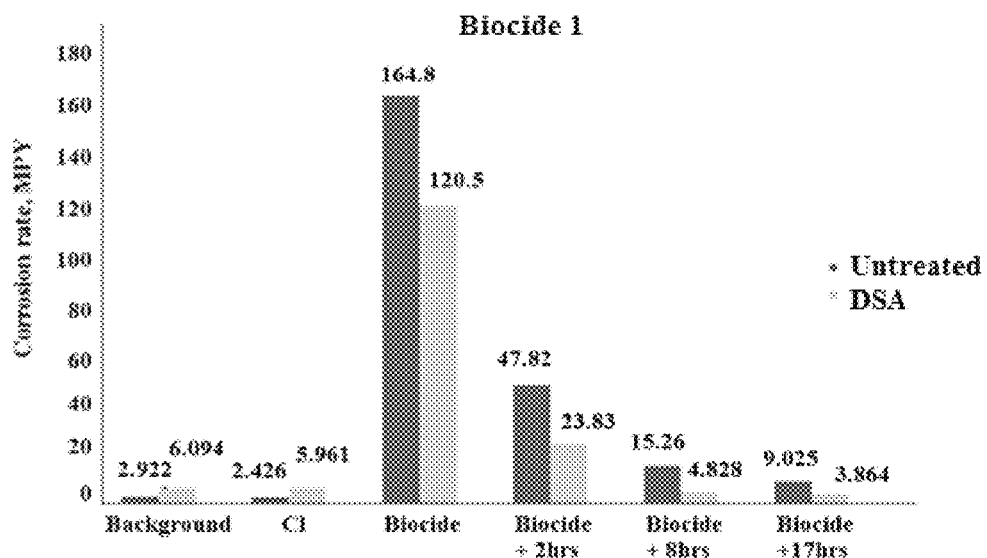
FIGS. 14A-14B shows the results from corrosion testing for biocide 1 (FIG. 14A) and biocide 2 (FIG. 14B) in combination with corrosion inhibitor molecule dodecyl succinic anhydride.
Figure 14B:
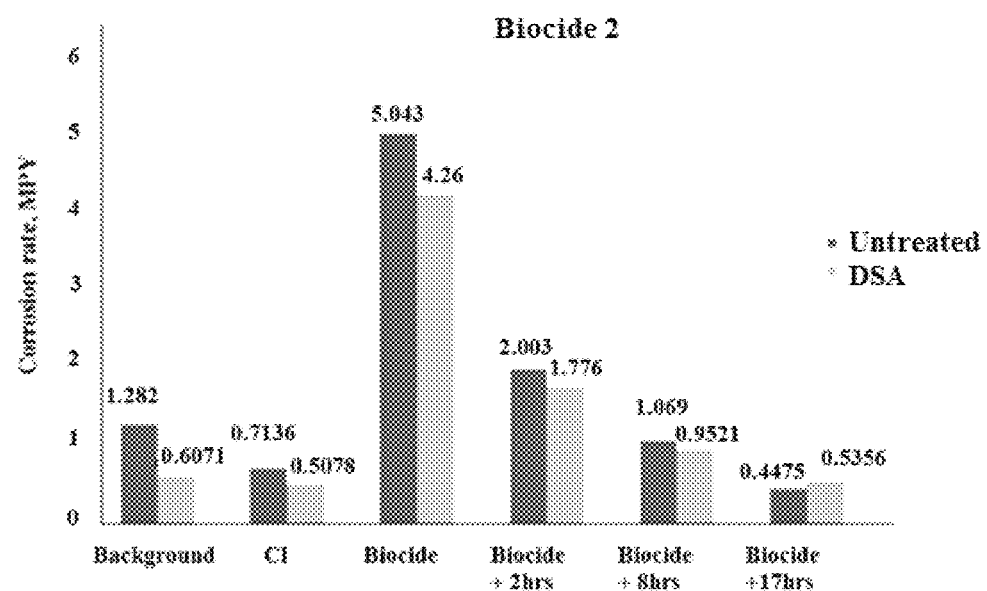
Figure 15A:
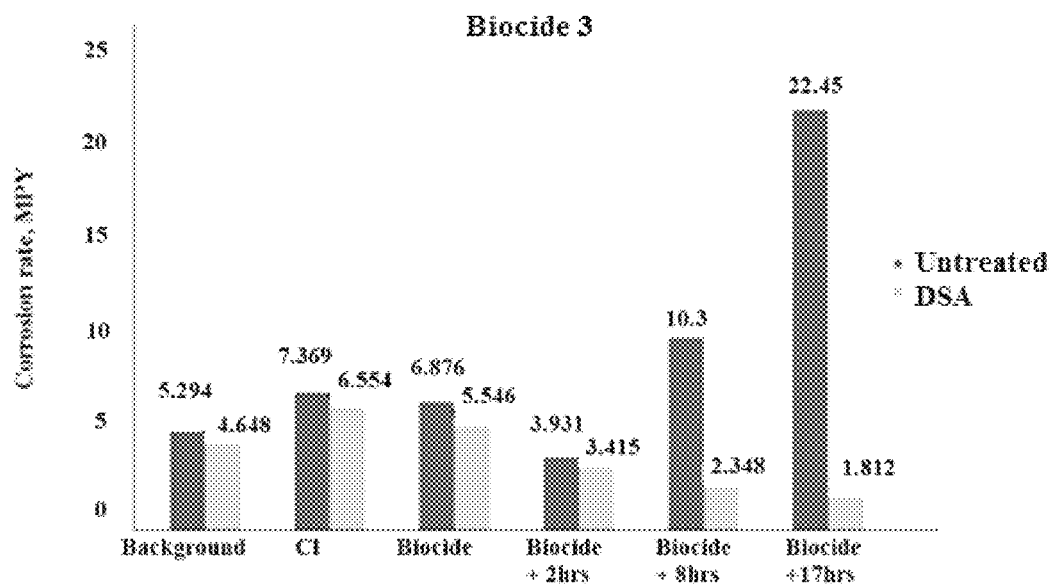
FIGS. 15A-15B show the results from corrosion testing for biocide 3 (FIG. 15A) and biocide 4 (FIG. 15B) in combination with corrosion inhibitor molecule dodecyl succinic anhydride.
Figure 15B:
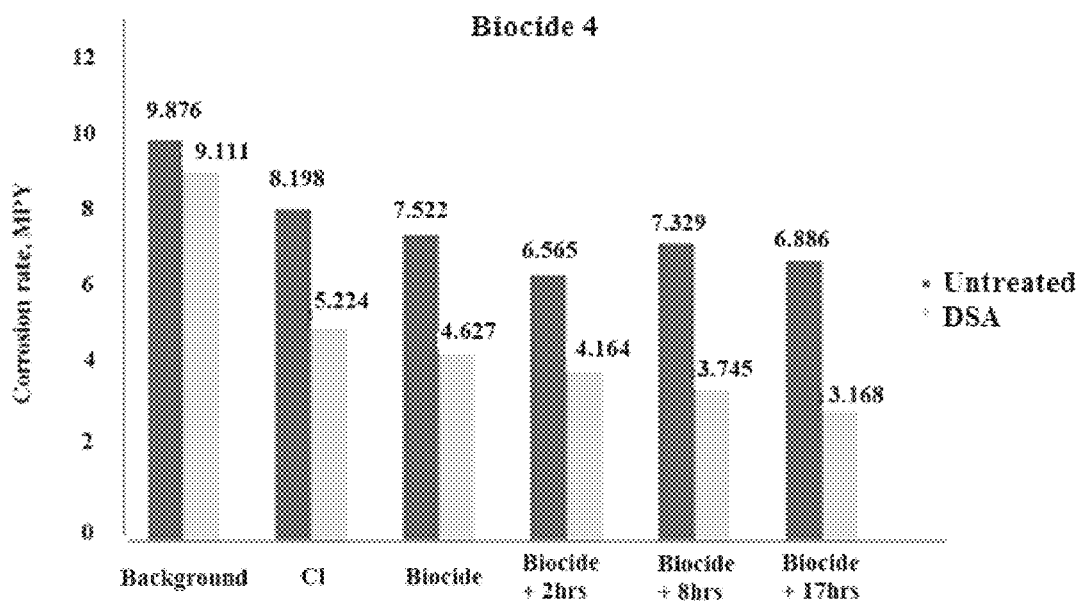
Figure 16A:
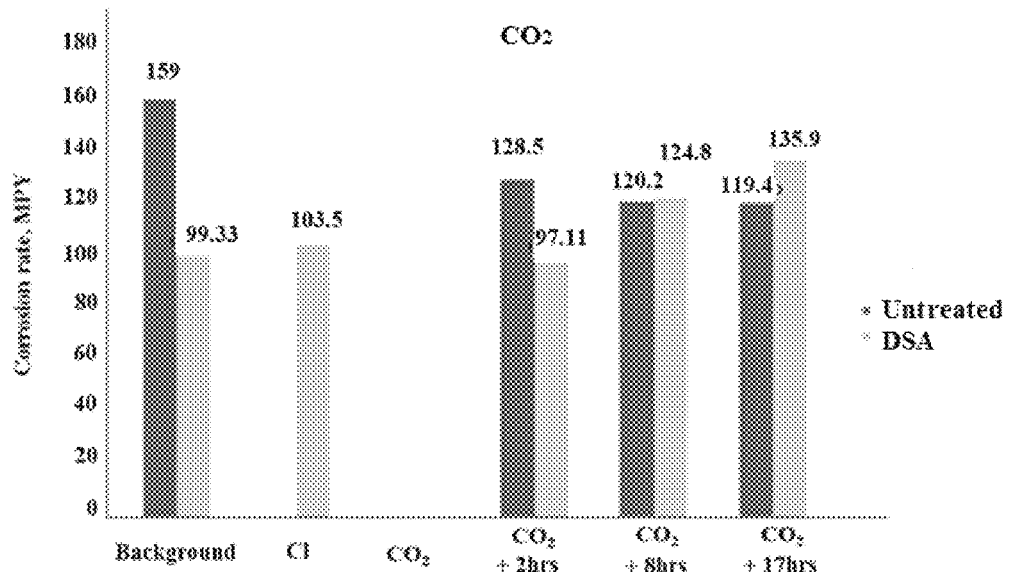
FIG. 16A plots the data testing the corrosion protection of dodecyl succinic anhydride against $CO_2$ corrosion according to an embodiment of the invention.

Table 8 and FIGS. 14, 15, and 16 provide evidence for the protective properties of Dodecyl succinic anhydride on the corrosion rate of 1018 carbon steel compared to untreated samples (Table 11). Specifically, this is apparent in samples treated with Biocide 1 (FIG. 14A and Table 8), Biocide 2 (FIG. 14B and Table 8), Biocide 3 (FIG. 15A and Table 8), Biocide 4 (FIG. 15B and Table 8), or untreated ($CO_2$) (FIG. 16A and Table 8). Likewise, Dodecyl succinic anhydride mediated corrosive protection can be seen when compared to samples treated with 100 ppm of CONTROL 1 (Table 12) and CONTROL 2 (Table 13).

FIG. 14 shows the results from corrosion testing for biocide 1 (FIG. 14A) and biocide 2 (FIG. 14B) in combination with corrosion inhibitor molecule, dodecyl succinic anhydride. FIG. 14A provides evidence for corrosion protection conferred by the addition of dodecyl succinic anhydride on the corrosion rate of 1018 carbon steel compared to untreated samples. However, even though the overall corrosion protection for biocide 2 treated with Dodecyl succinic anhydride is comparable to the untreated samples (FIG. 14B), the corrosion rate is well within the acceptable range of corrosion protection for an effective corrosion inhibitor.

FIG. 15 shows the results from corrosion testing for biocide 3 (FIG. 15A) and biocide 4 (FIG. 15B) in combination with corrosion inhibitor molecule, dodecyl succinic anhydride. Collectively, FIGS. 15A and 15B, provide evidence for the corrosion inhibiting properties of dodecyl succinic anhydride, as the rate of carbon steel coupon corrosion is significantly lower when treated in combination with dodecyl succinic anhydride compared to coupons treated with biocide 3 or biocide 4 alone.

Figure 16B:
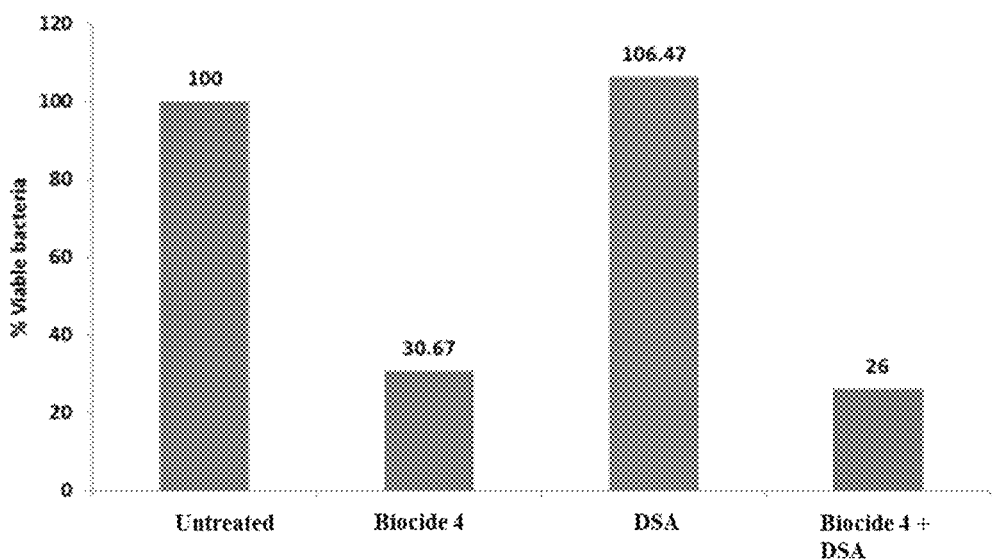
FIG. 16B shows dodecenyl succinic anhydride provides a modest increase in the biocidal properties of gluteraldehyde but is not efficient in reducing the number of viable microorganisms by itself according to an embodiment of the invention.

FIG. 16A plots the data testing the corrosion protection of dodecyl succinic anhydride against $CO_2$ corrosion. As can be seen by the data presented in FIG. 16A, dodecyl succinic anhydride does not confer additional protection against generalized corrosion produced by $CO_2$ compared to untreated controls. FIG. 16B shows dodecenyl succinic anhydride provides a modest increase in the biocidal properties of gluteraldehyde but is not efficient in reducing the number of viable microorganisms by itself. Taken together these data provide evidence for the corrosion protection conferred by Dodecenyl succinic anhydride and in the enhancement of biocide activity.

Example 6

Evaluation of Cetyl Pyridinium Bromide (CPBr) Corrosion Inhibitor

Experiments used to assess corrosion inhibition properties were performed as described previously in Example 1, using 120 ppm of Cetyl pyridinium bromide and 100 ppm of biocides. Corrosion data for Cetyl pyridinium bromide added to different biocides is tabulated in Table 9.

TABLE 9

(Corrosion rate of Cetyl pyridinium bromide (CPBr))

| Cetyl pyridinium bromide | Corrosion rate in MPY | | | | |
|---|---|---|---|---|---|
| | Biocide 1 | Biocide 2 | Biocide 3 | Biocide 4 | $CO_2$* |
| Background | 7.31 | 7.869 | 7.2380 | 7.8640 | 193.2000 |
| CI | 0.77 | 0.104 | 0.9756 | 0.5679 | 85.2200 |
| Biocide | 20.9 | 0.4069 | 0.6910 | 0.4975 | |
| Biocide + 2 hrs | 2.07 | 0.2664 | 0.4639 | 0.4701 | 37.0800 |
| Biocide + 8 hrs | 0.79 | 0.06566 | 0.3904 | 0.4857 | 17.1100 |
| Biocide + 17 hrs | 0.768 | 0.04248 | 0.3708 | 0.4578 | 11.4700 |

*No biocide was added in the $CO_2$ only tests

Figure 17A:
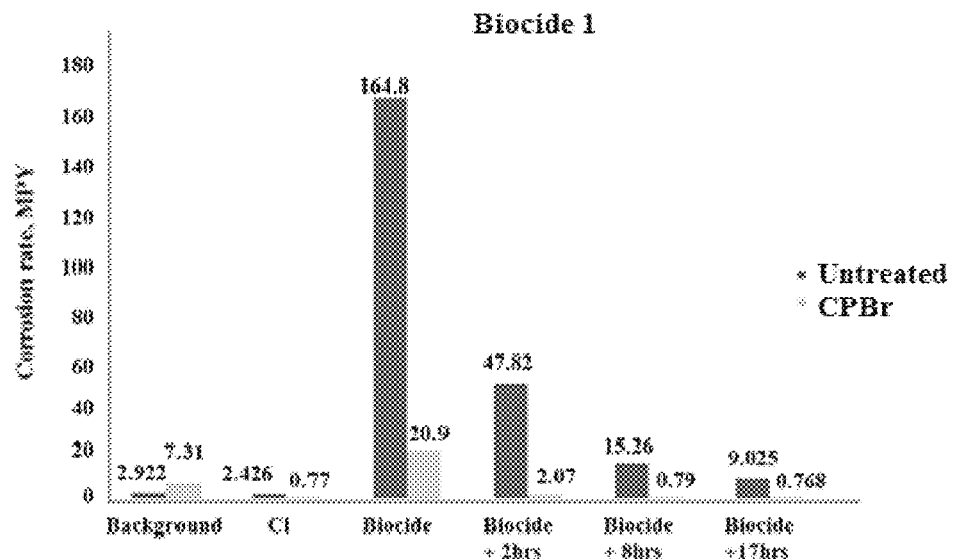
FIGS. 17A-17B show the results from corrosion testing for biocide 1 (FIG. 17A) and biocide 2 (FIG. 17B) in combination with corrosion inhibitor molecule cetyl pyridinium bromide.
Figure 17B:
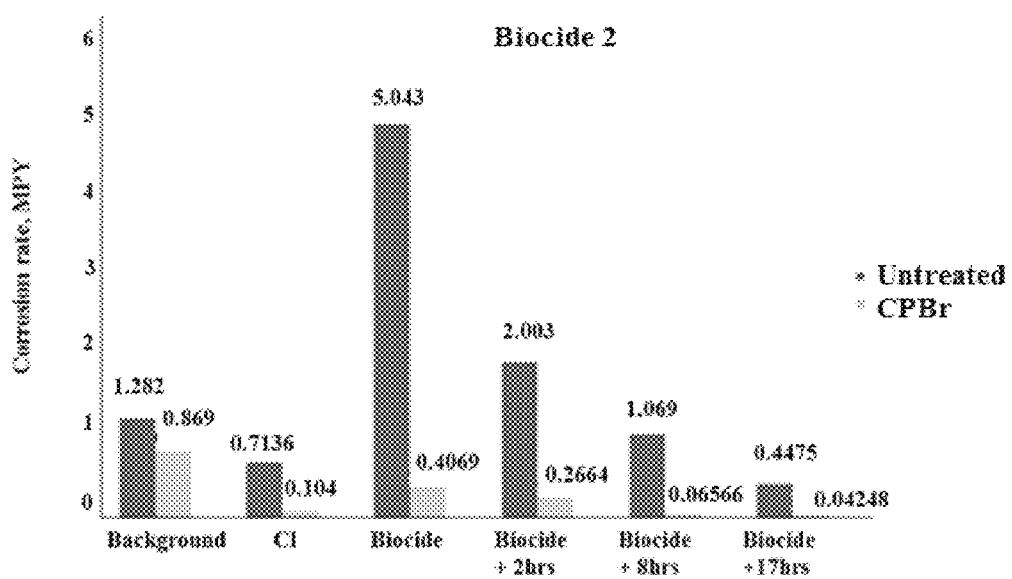
Figure 18A:
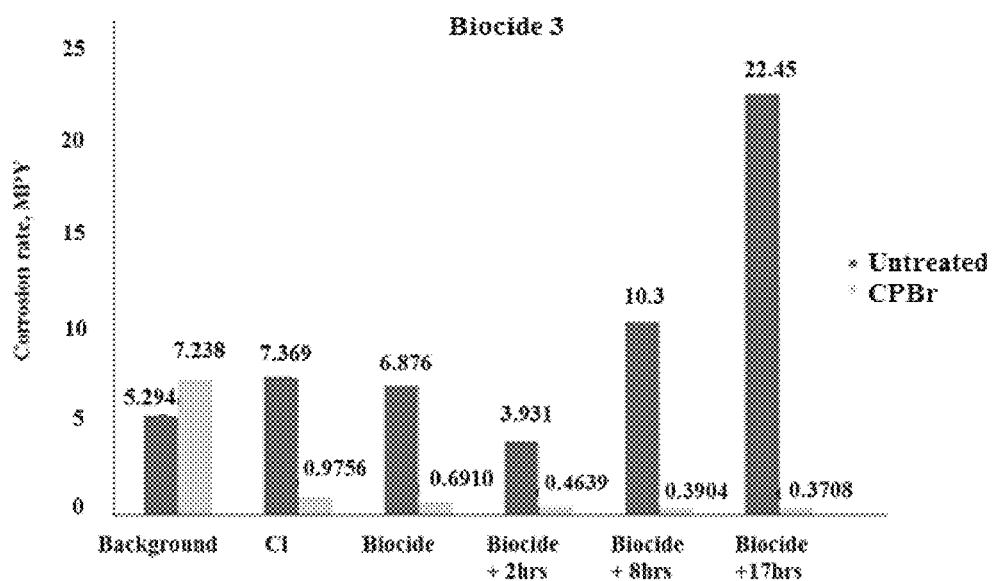
FIGS. 18A-18B show the results from corrosion testing for biocide 3 (FIG. 18A) and biocide 4 (FIG. 18B) in combination with corrosion inhibitor molecule cetyl pyridinium bromide.
Figure 18B:
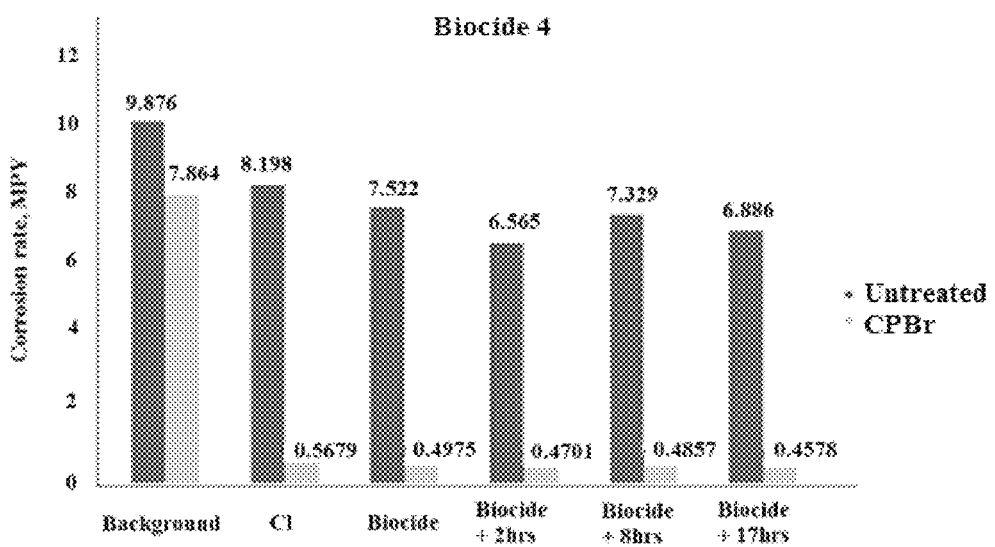
Figure 19A:
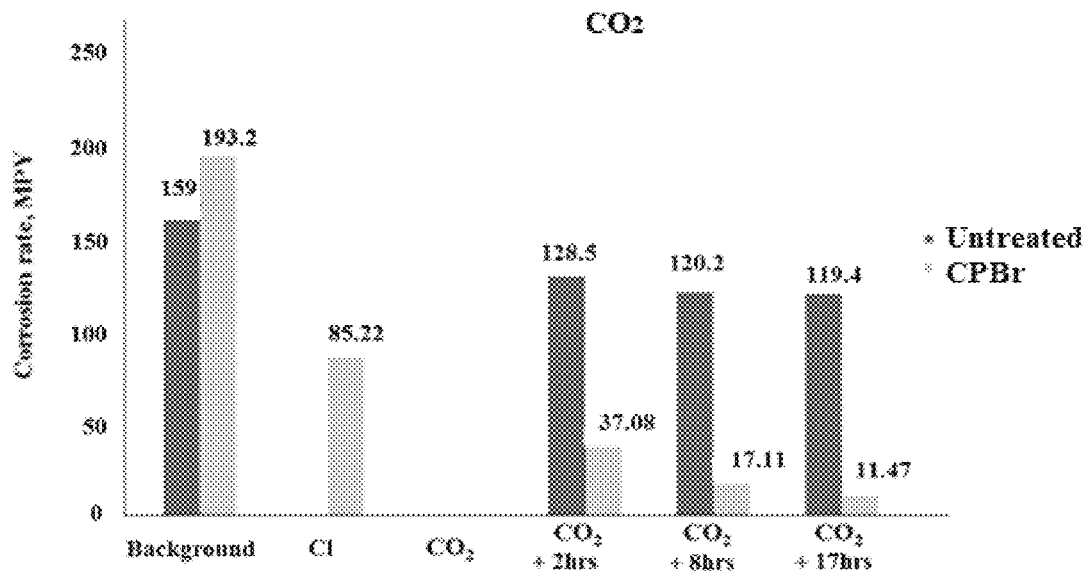
FIG. 19A tests the corrosion protective properties of cetyl pyridinium bromide against generalized corrosion produced by $CO_2$ according to an embodiment of the invention.

Table 9 and FIGS. 17, 18, and 19 provide evidence for the protective properties of Cetyl pyridinium bromide on the corrosion rate of 1018 carbon steel compared to untreated samples (Table 11). Specifically, this is apparent in samples treated with Biocide 1 (FIG. 17A and Table 9), Biocide 2 (FIG. 17B and Table 9), Biocide 3 (FIG. 18A and Table 9), Biocide 4 (FIG. 18B and Table 9), or untreated ($CO_2$) (FIG. 19A and Table 9). Likewise, Cetyl pyridinium bromide mediated corrosive protection can be seen when compared to samples treated with 100 ppm of CONTROL 1 (Table 12) and CONTROL 2 (Table 13).

FIG. 17 shows the results from corrosion testing for biocide 1 (FIG. 17A) and biocide 2 (FIG. 17B) in combination with corrosion inhibitor molecule, cetyl pyridinium bromide. Collectively, FIGS. 17A and 17B, provide evidence for the corrosion inhibiting properties of cetyl pyridinium bromide, as the rate of corrosion of 1018 carbon steel coupons is significantly lower when treated in combination with cetyl pyridinium bromide compared to coupons treated with biocide 1 or biocide 2 alone.

FIG. 18 shows the results from corrosion testing for biocide 3 (FIG. 18A) and biocide 4 (FIG. 18B) in combination with corrosion inhibitor molecule, cetyl pyridinium bromide. Collectively, FIGS. 18A and 18B, provide evidence for the corrosion inhibiting properties of cetyl pyridinium bromide, as the rate of corrosion of 1018 carbon steel coupons is significantly lower when treated in combination with cetyl pyridinium bromide compared to coupons treated with biocide 3 or biocide 4 alone.

Figure 19B:
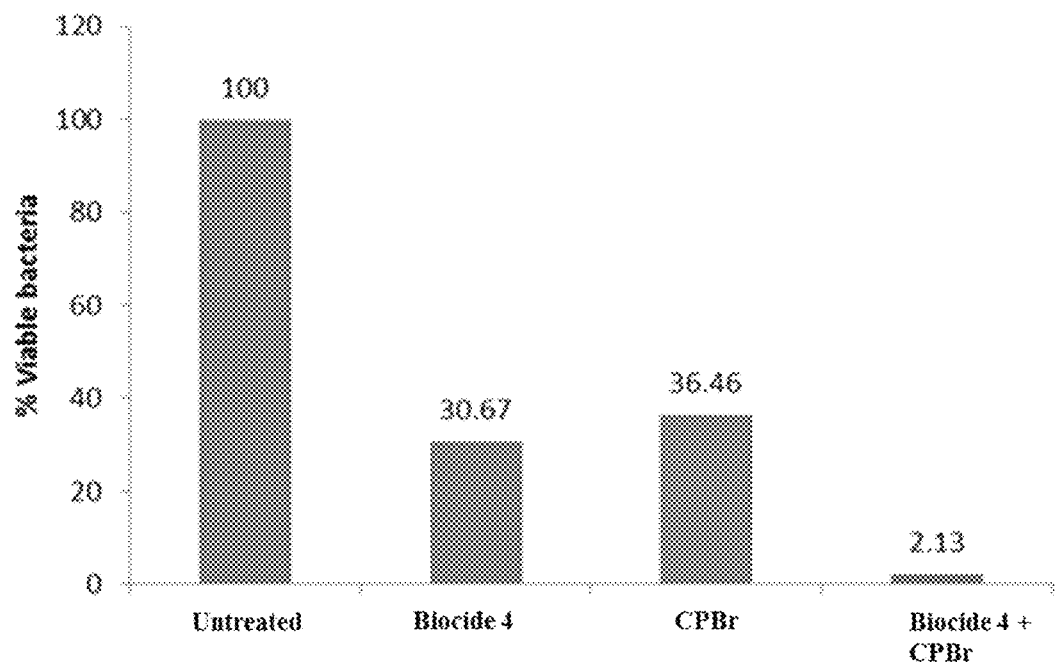
FIG. 19B shows cetyl pyridinium bromide provides excellent biocidal enhancement when used in conjunction with biocide 4, in addition to efficiently reducing the number of viable microorganisms by itself according to an embodiment of the invention.

FIG. 19A tests the corrosion protective properties of cetyl pyridinium bromide against generalized corrosion produced by $CO_2$. The data plotted in FIG. 19A shows that cetyl pyridinium bromide is sufficient to produce a lower corrosion rate compared to untreated controls. FIG. 19B shows cetyl pyridinium bromide provides excellent biocidal enhancement when used in conjunction with biocide 4, in addition to efficiently reducing the number of viable microorganisms by itself. Collectively these data are consistent for the support of the protective properties of Cetyl pyridinium bromide against corrosion and in the enhancement of biocide activity.

Example 7

Evaluation of Cetyl Pyridinium Chloride (CPCl) Corrosion Inhibitor

Experiments used to assess corrosion inhibition properties were performed as described previously in Example 1, using 120 ppm of Cetyl Pyridinium chloride and 100 ppm of biocides. Corrosion data for Cetyl Pyridinium chloride added to different biocides is tabulated in Table 10.

TABLE 10

(Corrosion rate of cetyl pyridinium chloride (CPCl))

| Cetyl pyridinium chloride | Corrosion rate in MPY | | | | |
|---|---|---|---|---|---|
| | Biocide 1 | Biocide 2 | Biocide 3 | Biocide 4 | $CO_2$* |
| Background | 8.14 | 10.49 | 1.0650 | 10.6200 | 130.2000 |
| CI | 0.77 | 0.7982 | 0.7489 | 0.4899 | 100.0000 |
| Biocide | 20.9 | 0.8032 | 0.2082 | 0.5195 | |
| Biocide + 2 hrs | 2.05 | 0.6038 | 0.1168 | 0.4446 | 43.7400 |
| Biocide + 8 hrs | 0.776 | 0.6764 | 0.1096 | 0.3826 | 22.7800 |
| Biocide + 17 hrs | 0.746 | 0.4709 | 0.1401 | 0.3189 | 17.1800 |

*No biocide was added in the $CO_2$ only tests

Figure 20A:
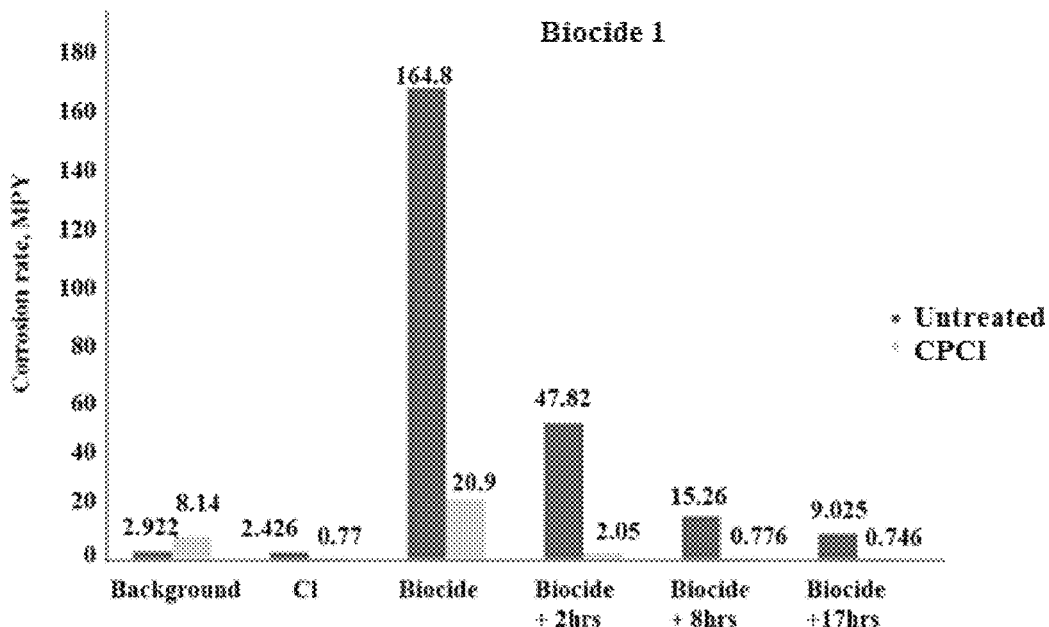
FIGS. 20A-20B show the results from corrosion testing for biocide 1 (FIG. 20A) and biocide 2 (FIG. 20B) in combination with corrosion inhibitor molecule cetyl pyridinium chloride.
Figure 20B:
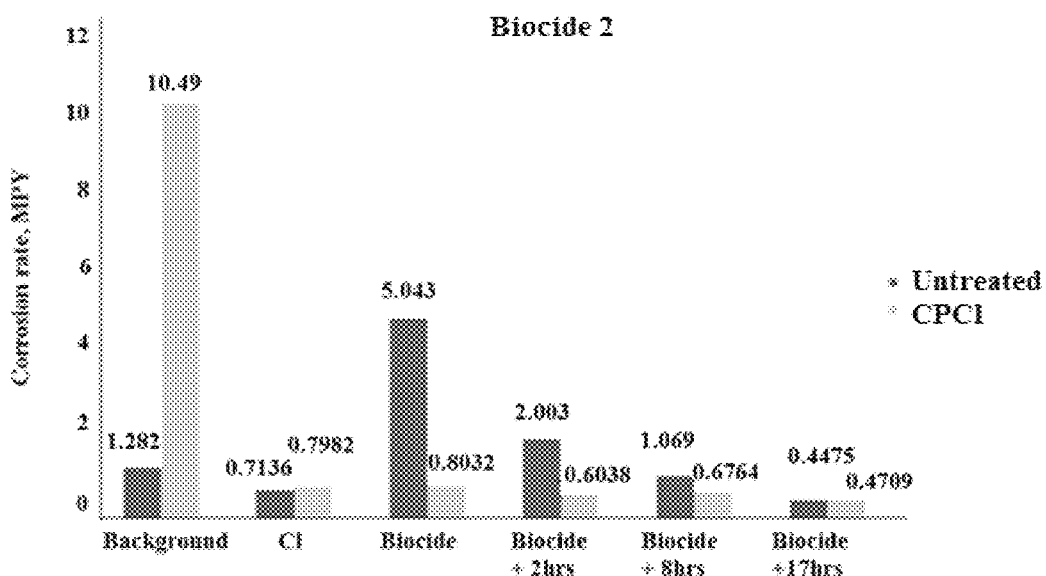
Figure 21A:
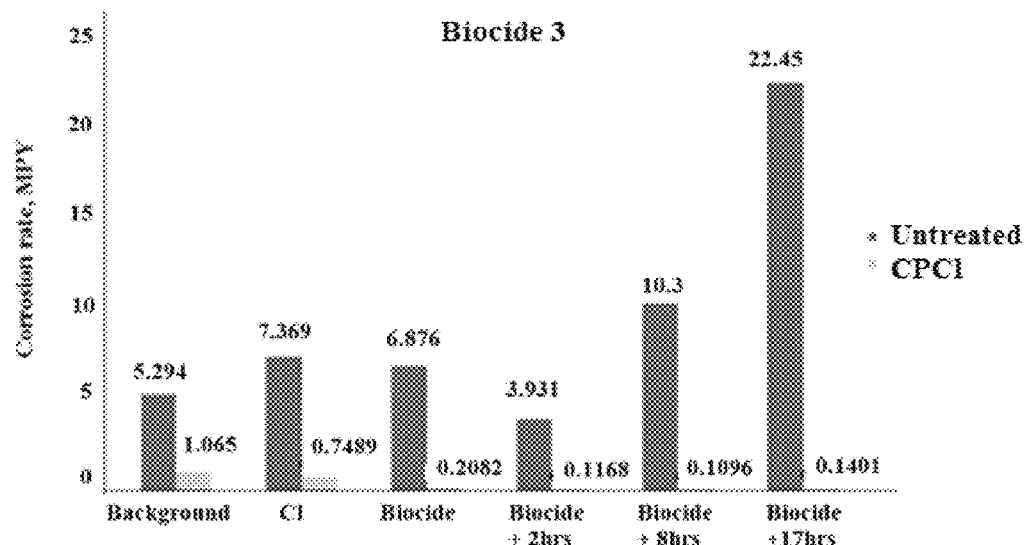
FIGS. 21A-21B provide further evidence of corrosion protective properties testing for biocide 3 (FIG. 21A) and biocide 4 (FIG. 21B) in combination with corrosion inhibitor molecule cetyl pyridinium chloride.
Figure 21B:
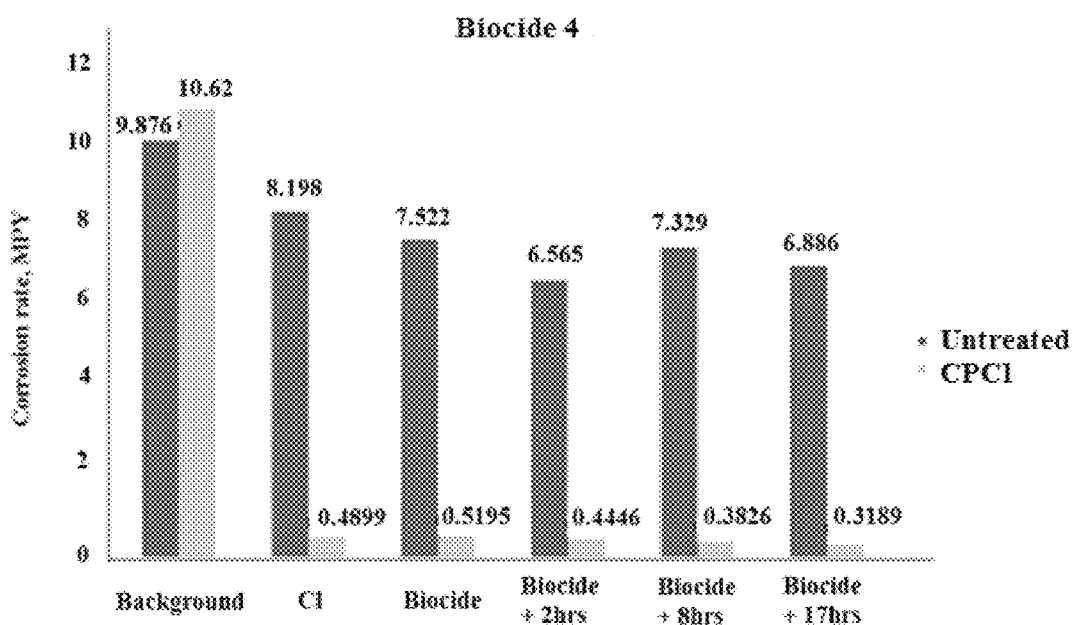
Figure 22A:
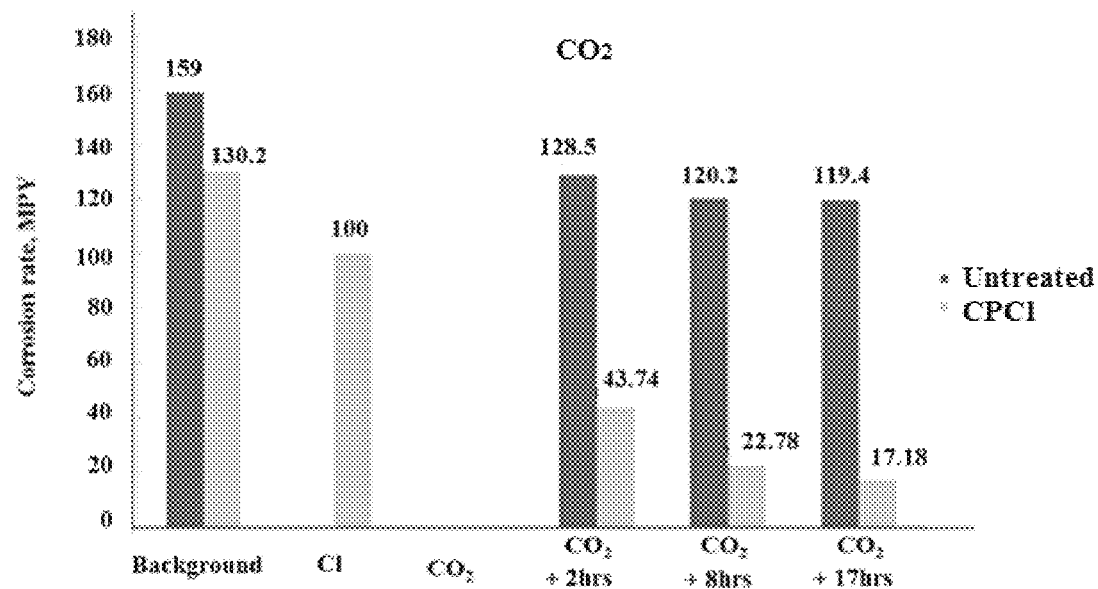
FIG. 22A shows the corrosion protective properties of cetyl pyridinium chloride against generalized corrosion produced by $CO_2$ according to an embodiment of the invention.

Table 10 and FIGS. 20, 21, and 22 provide evidence for the protective properties of Cetyl pyridinium chloride on the corrosion rate of 1018 carbon steel compared to untreated samples (Table 11). Specifically, this is apparent in samples treated with Biocide 1 (FIG. 20A and Table 10), Biocide 2 (FIG. 20B and Table 10), Biocide 3 (FIG. 21A and Table 10), Biocide 4 (FIG. 21B and Table 10), or untreated ($CO_2$) (FIG. 22A and Table 10). Likewise, Cetyl pyridinium chloride mediated corrosive protection can be seen when compared to samples treated with 100 ppm of CONTROL 1 (Table 12) and CONTROL 2 (Table 13).

FIG. 20 shows the results from corrosion testing for biocide 1 (FIG. 20A) and biocide 2 (FIG. 20B) in combination with corrosion inhibitor molecule, cetyl pyridinium chloride. Collectively, FIGS. 20A and 20B, provide evidence for the corrosion inhibiting properties of cetyl pyridinium chloride, as the rate of corrosion of 1018 carbon steel coupons is significantly lower when treated in combination with cetyl pyridinium chloride compared to coupons treated with biocide 1 or biocide 2 alone.

FIG. 21 provides further evidence of corrosion protective properties testing for biocide 3 (FIG. 21A) and biocide 4 (FIG. 21B) in combination with corrosion inhibitor molecule, cetyl pyridinium chloride. Collectively, FIGS. 21A and 21B, provide evidence for the corrosion inhibiting properties of cetyl pyridinium chloride, as the rate of corrosion of 1018 carbon steel coupons is significantly lower when treated in combination with cetyl pyridinium chloride compared to coupons treated with biocide 3 or biocide 4 alone.

Figure 22B:
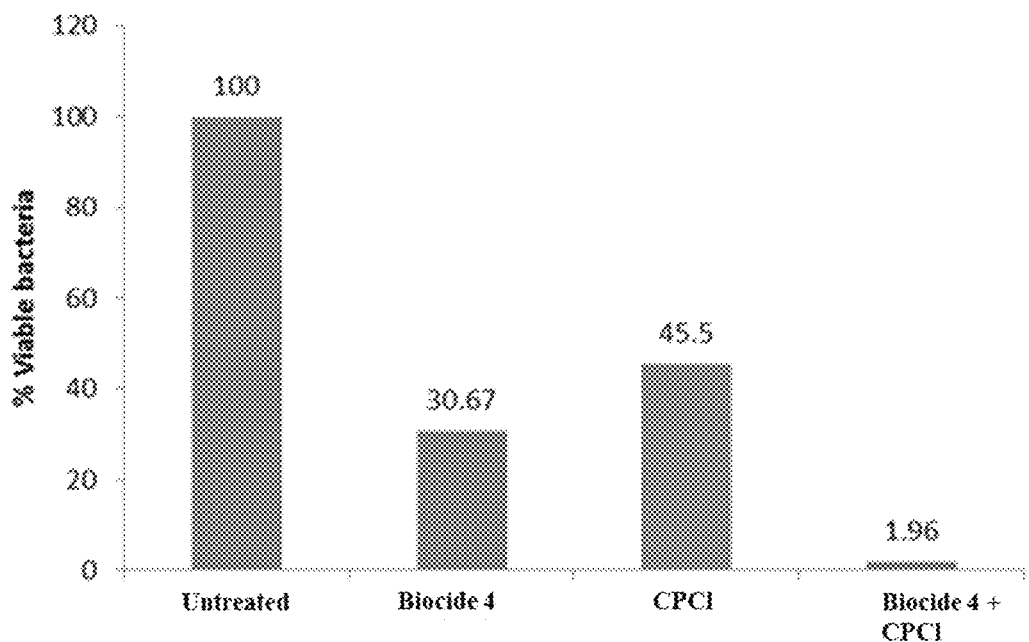
FIG. 22B shows cetyl pyridinium chloride provides excellent biocidal enhancement when used in conjunction with biocide 4, in addition to efficiently reducing the number of viable microorganisms by itself according to an embodiment of the invention.

FIG. 22A tests the corrosion protective properties of cetyl pyridinium chloride against generalized corrosion produced by $CO_2$. The data plotted in FIG. 22A shows that cetyl pyridinium chloride is sufficient to produce a lower corrosion rate compared to untreated controls. FIG. 22B shows cetyl pyridinium chloride provides excellent biocidal enhancement when used in conjunction with biocide 4, in addition to efficiently reducing the number of viable microorganisms by itself. Collectively these data are consistent for the support of the protective properties of Cetyl pyridinium chloride against corrosion and in the enhancement of biocide activity.

Example 8

Evaluation of CONTROL 1, CONTROL 2, and No Corrosion Inhibitor

Experiments used to assess corrosion inhibition properties were performed as described previously in Example 1, using 120 ppm of CONTROL 1 (Table 12) or 120 ppm of CONTROL 2 (Table 13) or no corrosion inhibitor (Table 11) and 100 ppm of biocides.

TABLE 11

(Corrosion rate in MPY of produced water brine treated with 100 ppm of biocide)

| No corrosion inhibitor | Biocide 1 | Biocide 2 | Biocide 3 | Biocide 4 | $CO_2$* |
|---|---|---|---|---|---|
| Background | 2.922 | 1.282 | 5.2940 | 9.8760 | 159.0000 |
| Biocide | 164.8 | 5.043 | 6.8760 | 7.5220 | |
| Biocide + 2 hrs | 47.82 | 2.003 | 3.9310 | 6.5650 | 128.5000 |
| Biocide + 8 hrs | 15.26 | 1.069 | 10.3000 | 7.3290 | 120.2000 |
| Biocide + 17 hrs | 9.025 | 0.4475 | 22.4500 | 6.8860 | 119.4000 |

*No biocide was added in the $CO_2$ only tests.

TABLE 12

(Corrosion rate in MPY of produced water brine treated with 120 ppm of CONTROL 1 (Quat) and 100 ppm of the biocide)
CONTROL 1

| | Biocide 1 | Biocide 2 | Biocide 3 | Biocide 4 | $CO_2$* |
|---|---|---|---|---|---|
| Background | 2.956 | 10.6 | 1.13 | 9.49 | 73.4000 |
| CI | 0.6718 | 0.6933 | 0.64 | 0.64 | 60.3400 |
| Biocide | 100 | 0.6607 | 0.25 | 0.60 | |
| Biocide + 2 hrs | 47.6 | 0.6369 | 0.17 | 0.47 | 76.5700 |
| Biocide + 8 hrs | 22.2 | 0.5407 | 0.16 | 0.38 | 112.9000 |
| Biocide + 17 hrs | 14.82 | 0.4188 | 0.16 | 0.44 | 125.2000 |

*No biocide was added in the $CO_2$ only tests

TABLE 13

(Corrosion rate in MPY of produced water brine treated with 120 ppm of CONTROL 2 (Imidazoline) and 100 ppm of the biocide)
CONTROL 2

| | Biocide 1 | Biocide 2 | Biocide 3 | Biocide 4 | $CO_2$* |
|---|---|---|---|---|---|
| Background | 6.494 | 10.75 | 6.61 | 9.28 | 111.1000 |
| CI | 1.034 | 0.5612 | 2.36 | 0.96 | 115.2000 |
| Biocide | 166.1 | 0.7421 | 1.53 | 0.80 | |
| Biocide + 2 hrs | 53.73 | 0.5246 | 1.31 | 0.63 | 17.0600 |
| Biocide + 8 hrs | 29.6 | 0.3357 | 0.89 | 0.41 | 2.5910 |
| Biocide + 17 hrs | 34.49 | 0.2842 | 1.09 | 0.33 | 1.7490 |

*No biocide was added in the $CO_2$ only tests

TABLE 14

(Corrosion rate in MPY of produced water brine treated with 120 ppm of CONTROL 3 (2-mercaptoethanol) and 100 ppm of the biocide)
CONTROL 3

| | Biocide 1 | Biocide 2 | Biocide 3 | Biocide 4 | $CO_2$* |
|---|---|---|---|---|---|
| Background | 3.8 | 11.6 | 8.37 | 8.36 | 105.5000 |
| CI | 6.1 | 15.96 | 10.74 | 10.57 | 9.1810 |
| Biocide | 28.1 | 26.89 | 9.62 | 10.12 | |
| Biocide + 2 hrs | 27.7 | 22.43 | 3.57 | 10.20 | 4.0350 |
| Biocide + 8 hrs | 20.5 | 17.78 | 1.36 | 8.91 | 3.0320 |
| Biocide + 17 hrs | 18.1 | 13.44 | 1.25 | 7.39 | 2.7150 |

In embodiments of the invention a synergist is often added to the corrosion inhibitor formulations to enhance performance. However, synergist alone does not provide any corrosion protection in the presence of a biocide in produced water, as shown in Table 14 with the control testing. When tested in brine, under $CO_2$ saturated conditions, the synergist provides excellent corrosion protection.

Collectively, the known corrosion inhibitors CONTROL 1 and CONTROL 2 provide similar corrosion inhibitory properties when compared to cocoamphodiproprionate sodium salt, hyperbranched polyeasteramide (shown as 55N), cocoglucoside dimethicone, 2-hydroxylethyl-N-methylbutane-1-sulphonamide, or dodecyl succinic anhydride demonstrating the corrosion inhibitors provide at least substantially similar performance or improved corrosion inhibition performance as commercially-available controls. Whereas cetyl pyridinium bromide and cetyl pyridinium chloride provide the most resistance to corrosion against the biocides tested, in addition to providing the most biocidal enhancing effects in combination with Biocide 4.

Figure 23:
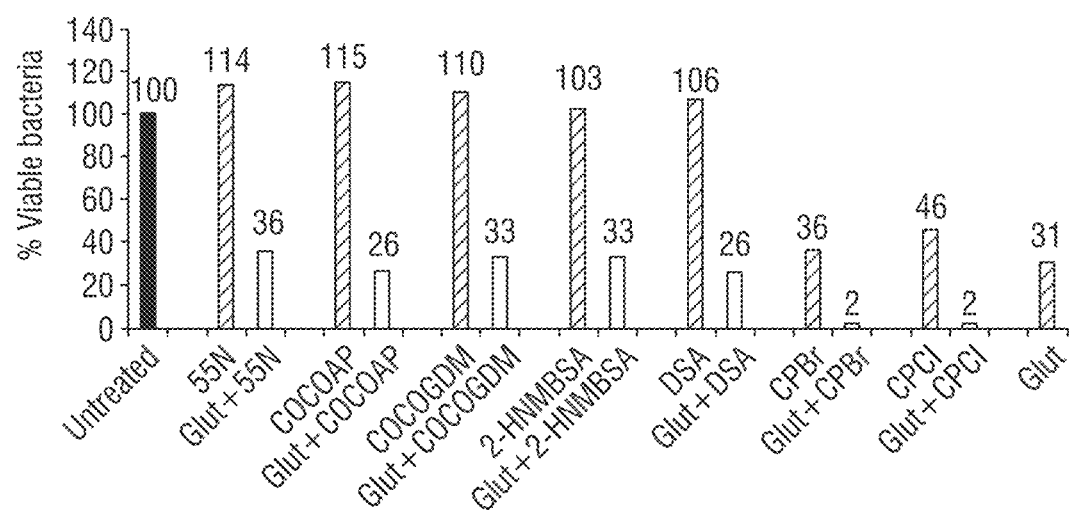
FIG. 23 shows the percentage viable bacterial for untreated versus corrosion inhibitor treated systems wherein corrosion inhibitor molecules cetyl pyridinium bromide and cetyl pyridinium chloride show enhancement in biocide activity when used in conjunction with a biocide according to an embodiment of the invention.

FIG. 23 shows the percentage viable bacterial for untreated, 120 ppm corrosion inhibitor treated and 120 ppm corrosion inhibitor+100 ppm biocide 4 treated. Cetyl pyridinium bromide and cetyl pyridinium chloride show enhancement in biocide activity when used in conjunction with a biocide.

The inventions being thus described, it will be obvious that the same may be varied in many ways. Such variations are not to be regarded as a departure from the spirit and scope of the inventions and all such modifications are intended to be included within the scope of the following claims. The above specification provides a description of the manufacture and use of the disclosed compositions and methods. Since many embodiments can be made without departing from the spirit and scope of the invention, the invention resides in the claims.

What is claimed is:

1. A peroxyformic acid corrosion inhibited composition comprising:
   from about 0.5 ppm to about 50,000 ppm of an oxidizing biocide comprising a peroxyformic acid forming composition; and
   from about 1 ppm to about 1,000 ppm of a corrosion inhibitor, wherein the corrosion inhibitor is alkyl pyridinium salts, cetyl pyridinium salts, polyesteramides, dimethicones, imidazole derivatives, sulphonamides or a combination thereof,
   wherein the composition has a pH below 12.0, and wherein the corrosion inhibited
   aqueous composition provides a treated surface or system with a corrosion rate of less than about 4 mils per year (MPY).

2. The composition of claim 1, wherein the oxidizing biocide further comprises one or more C1-C22 peroxycarboxylic acid compositions or C1-C22 peroxycarboxylic acid forming compositions.

3. The composition of claim 2, wherein the peroxyformic acid is formed from a two part composition, wherein the first part is a premix comprising formic acid and/or an ester of a polyhydric alcohol and formic acid and the corrosion inhibitor, and wherein the second part is a source of hydrogen peroxide.

4. The composition of claim 3, wherein the first part of the premix is shelf-stable for a period of at least 1 month.

5. The composition of claim 3, wherein the first part of the premix is shelf-stable for a period of at least 6 months.

6. The composition of claim 3, wherein the two part composition is combined to generate the peroxyformic c acid in situ and wherein the two part composition is shelf-stable for a period of at least 1 month.

7. The composition of claim 3, wherein the premix comprises formic acid and a corrosion inhibitor.

8. The composition of claim 3, wherein the premix comprises from about 1 to about 99 wt-% formic acid and/or an ester of a polyhydric alcohol and formic acid and from about 1 to about 99 wt-% corrosion inhibitor.

9. The composition of claim 8, wherein the premix comprises from about 20 to about 80 wt-% formic acid and/or an ester of a polyhydric alcohol and formic acid and from about 20 to about 80 wt-% corrosion inhibitor.

10. The composition of claim 3, wherein the first premix and/or the second part comprise one or more additional functional ingredients.

11. The composition of claim 10, wherein the one or more additional functional ingredients are a catalyst, stabilizing agent, pH buffering agent, acidulant, friction reducer, viscosity enhancer, defoaming agent, anti-redeposition agent, bleaching agent, solubility modifier, dispersant, metal protecting agent, additional corrosion inhibitor, additional biocide, scale inhibitor, sequestrant and/or chelating agent, peracid stabilizer, surfactant and/or antimicrobial agent, additional carboxylic acid, emulsion breaker, emulsion stabilizer, fragrance and/or dye, rheology modifier or thickener, hydrotrope or coupler, buffer, solvent and/or combinations thereof.

12. The composition of claim 1, wherein the composition is shelf-stable for a period of at least 1 month.

* * * * *

UNITED STATES PATENT AND TRADEMARK OFFICE
CERTIFICATE OF CORRECTION

PATENT NO. : 10,590,282 B2  
APPLICATION NO. : 15/349536  
DATED : March 17, 2020  
INVENTOR(S) : Ramakrishnan Balasubramanian et al.

Page 1 of 1

It is certified that error appears in the above-identified patent and that said Letters Patent is hereby corrected as shown below:

In the Claims

<u>In Column 51, Claim 6, Line 17:</u>
DELETE "c acid" before the word "in"

Signed and Sealed this
Twenty-third Day of June, 2020

Andrei Iancu
*Director of the United States Patent and Trademark Office*